(12) United States Patent
Lee et al.

(10) Patent No.: US 11,271,170 B2
(45) Date of Patent: Mar. 8, 2022

(54) HETEROCYCLIC COMPOUND AND ORGANIC LIGHT-EMITTING DEVICE INCLUDING THE SAME

(71) Applicant: Samsung Display Co., Ltd., Yongin-si (KR)

(72) Inventors: Yeseul Lee, Yongin-si (KR); Hyeongmin Kim, Yongin-si (KR); Heechoon Ahn, Yongin-si (KR); Hyunah Um, Yongin-si (KR); Yirang Im, Yongin-si (KR); Soobyung Ko, Yongin-si (KR); Jongwoo Kim, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 367 days.

(21) Appl. No.: 16/556,852

(22) Filed: Aug. 30, 2019

(65) Prior Publication Data
US 2020/0295266 A1 Sep. 17, 2020

(30) Foreign Application Priority Data
Mar. 13, 2019 (KR) .......................... 10-2019-0028857

(51) Int. Cl.
*H01L 51/00* (2006.01)
*C07D 519/00* (2006.01)
(Continued)

(52) U.S. Cl.
CPC ........ *H01L 51/0071* (2013.01); *C07D 519/00* (2013.01); *C09K 11/025* (2013.01);
(Continued)

(58) Field of Classification Search
None
See application file for complete search history.

(56) References Cited

U.S. PATENT DOCUMENTS

| 2016/0133844 | A1* | 5/2016 | Kim | .................... | H01L 51/0054 |
| | | | | | 257/40 |
| 2016/0163999 | A1* | 6/2016 | Kim | .................... | H01L 51/0071 |
| | | | | | 257/40 |

(Continued)

FOREIGN PATENT DOCUMENTS

| CN | 10704611 A | * 8/2017 | ............. H01L 51/50 |
| JP | 2016-9824 A | 1/2016 | |

(Continued)

OTHER PUBLICATIONS

SciFinder reference detail for Osman et al. "Synthesis of new 5-substituted phnoxyacetyl—and alpha-naphthoxyacetyl-2-aryloxazolo[4,5-b]phenoxazines" Indian Journal of Chemistry Section B: Organic Chemistry Including Medicinal Chemistry, 15B, 488-490, 1977, 2 pages. (Year: 1977).*

*Primary Examiner* — Robert S Loewe
(74) *Attorney, Agent, or Firm* — Lewis Roca Rothgerber Christie LLP

(57) ABSTRACT

Provided are a heterocyclic compound and an organic light-emitting device including the same. The heterocyclic compound is represented by Formula 1. The organic light-emitting device includes: a first electrode; a second electrode facing the first electrode; and an organic layer between the first electrode and the second electrode and including an emission layer, wherein the organic layer includes at least one of the heterocyclic compound represented by Formula 1.

20 Claims, 4 Drawing Sheets

10

| 190 |
| 150 |
| 110 |

(51) Int. Cl.
*C09K 11/02* (2006.01)
*H01L 51/50* (2006.01)

(52) U.S. Cl.
CPC ...... *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2018/0123049 A1* 5/2018 Lee .................. C07D 403/10
2018/0138429 A1* 5/2018 Fuchiwaki .......... H01L 51/0073

FOREIGN PATENT DOCUMENTS

| KR | 10-2013-0115161 A | 10/2013 | |
|---|---|---|---|
| KR | 10-2014-0038060 A | 3/2014 | |
| WO | WO-2013122364 A2 * | 8/2013 | ......... H01L 51/0071 |

* cited by examiner

| |
|---|
| 190 |
| 150 |
| 110 |

| |
|---|
| 190 |
| 150 |
| 110 |
| 210 |

| 220 |
|---|
| 190 |
| 150 |
| 110 |

| 220 |
|---|
| 190 |
| 150 |
| 110 |
| 210 |

HETEROCYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0028857, filed on Mar. 13, 2019, in the Korean Intellectual Property Office, the entire content of which is incorporated herein by reference.

BACKGROUND

1. Field

One or more embodiments relate to a heterocyclic compound and an organic light-emitting device including the same.

2. Description of the Related Art

Organic light-emitting devices are self-emission devices that produce full-color images, and also have wide viewing angles, high contrast ratios, short response times, and excellent characteristics in terms of brightness, driving voltage, and response speed, as compared to other devices in the art.

An example of such organic light-emitting devices may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

Aspects of embodiments of the present disclosure provide a heterocyclic compound having a novel structure and an organic light-emitting device including the same.

Additional aspects of embodiments will be set forth in part in the description which follows and, in part, will be apparent from the description, or may be learned by practice of the presented embodiments.

An aspect of an embodiment of the present disclosure provides a heterocyclic compound represented by Formula 1:

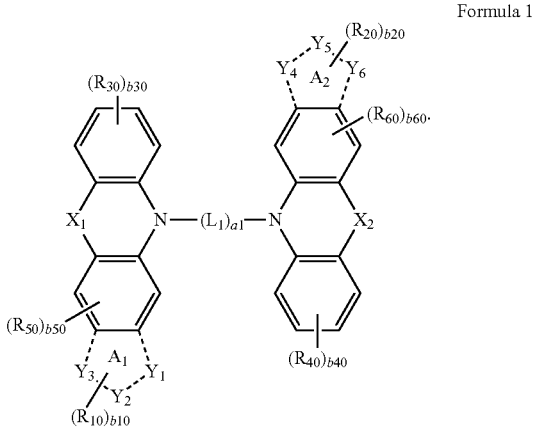

Formula 1

In Formula 1, $X_1$ may be a single bond O, S, $N(R_3)$, $C(R_4)(R_5)$, or $Si(R_4)(R_5)$, $X_2$ may be a single bond O, S, $N(R_6)$, $C(R_7)(R_8)$, or $Si(R_7)(R_8)$, each of $X_1$ and $X_2$ may be not both a single bond, $A_1$ and $A_2$ may each independently be a 5-membered $C_2$-$C_4$ heterocyclic group, $Y_1$, $Y_2$, $Y_3$, $Y_4$, $Y_5$, and $Y_6$ may each independently be selected from N, C, O, and S, $L_1$ may be selected from a substituted or unsubstituted $C_5$-$C_{60}$ carbocyclic group and a substituted or unsubstituted $C_1$-$C_{60}$ heterocyclic group, a1 may be an integer from 1 to 3, $R_3$, $R_4$, $R_5$, $R_6$, $R_7$, $R_8$, $R_{10}$, $R_{20}$, $R_{30}$, $R_{40}$, $R_{50}$, and $R_{60}$ may each independently be selected from hydrogen, deuterium, —F, —Cl, —Br, —I, a hydroxyl group, a cyano group, a nitro group, an am idino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$C(=O)(Q_1)$, —$N(Q_1)(Q_2)$, $P(=O)(Q_1)(Q_2)$, and —$S(=O)_2(Q_1)(Q_2)$, b10 and b20 may each independently be an integer from 0 to 3, b30 and b40 may each independently be an integer from 0 to 4, b50 and b60 may each independently be an integer from 0 to 2, at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Another aspect of an embodiment of the present disclosure provides an organic light-emitting device including: a first electrode; a second electrode facing the first electrode; and an organic layer between the first electrode and the second electrode and including an emission layer, wherein the organic layer includes at least one of the heterocyclic compound represented by Formula 1.

BRIEF DESCRIPTION OF THE DRAWINGS

These and/or other aspects of embodiments will become apparent and more readily appreciated from the following description of the embodiments, taken in conjunction with the accompanying drawings in which:

FIG. 1 is a schematic view of an organic light-emitting device according to an embodiment;

FIG. 2 is a schematic view of an organic light-emitting device according to another embodiment;

FIG. 3 is a schematic view of an organic light-emitting device according to another embodiment; and FIG. 4 is a schematic view of an organic light-emitting device according to another embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list.

A heterocyclic compound according to an embodiment is represented by Formula 1:

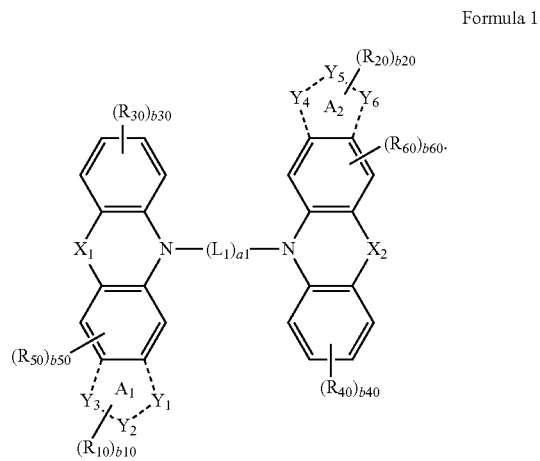

Formula 1

Formula 1 will be described below in more detail.

$X_1$ may be a single bond O, S, N($R_3$), C($R_4$)($R_5$), or Si($R_4$)($R_5$), and $X_2$ may be a single bond O, S, N($R_6$), C($R_7$)($R_8$), or Si($R_7$)($R_8$). When one selected from $X_1$ and $X_2$ is a single bond, the other thereof is not a single bond. For example, each of $X_1$ and $X_2$ is not a single bond at the same time (e.g., $X_1$ and $X_2$ are not both a single bond).

$A_1$ and $A_2$ may each independently be a 5-membered $C_2$-$C_4$ heterocyclic group, and $Y_1$, $Y_2$, $Y_3$, $Y_4$, $Y_5$, and $Y_6$ may each independently be selected from N, C, O, and S. Because $A_1$ and $A_2$ are a heterocyclic group, at least one selected from $Y_1$, $Y_2$, and $Y_3$ and at least one selected from $Y_4$, $Y_5$, and $Y_6$ may be N, O, or S.

$L_1$ may be selected from a substituted or unsubstituted $C_5$-$C_{60}$ carbocyclic group and a substituted or unsubstituted $C_1$-$C_{60}$ heterocyclic group.

a1 may be an integer from 1 to 3.

$R_3$, $R_4$, $R_5$, $R_6$, $R_7$, $R_8$, $R_{10}$, $R_{20}$, $R_{30}$, $R_{40}$, $R_{50}$, and $R_{60}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), P(=O)($Q_1$)($Q_2$), and —S(=O)$_2$($Q_1$)($Q_2$), wherein $Q_1$ to $Q_3$ will be described in more detail herein below.

b10 and b20 may each independently be an integer from 0 to 3, b30 and b40 may each independently be an integer from 0 to 4, and b50 and b60 may each independently be an integer from 0 to 2.

In one embodiment, at least one substituent selected from the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one embodiment, $X_1$ and $X_2$ may be identical to or different from each other.

In one embodiment, $A_1$ and $A_2$ may each independently be a 5-membered $C_2$-$C_4$ heterocyclic group including nitrogen, oxygen, sulfur, or any combination thereof.

In one or more embodiments, $A_1$ and $A_2$ may each independently be a pyrrole group, a thiophene group, a furan group, a pyrazole group, an imidazole group, an oxazole group, an isoxazole group, a thiazole group, or an isothiazole group.

In one embodiment, $L_1$ may be selected from:

a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a phenylcarbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a phenylcarbazole group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a phenylcarbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

In one embodiment, $L_1$ may be selected from groups represented by Formulae 3-1 to 3-46:

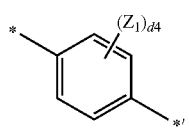

Formula 3-1

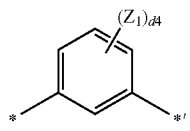

Formula 3-2

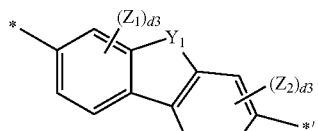

Formula 3-3

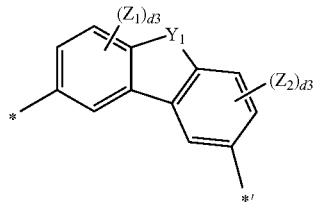

Formula 3-4

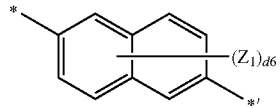

Formula 3-5

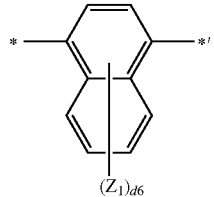

Formula 3-6

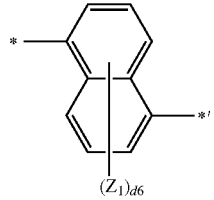

Formula 3-7

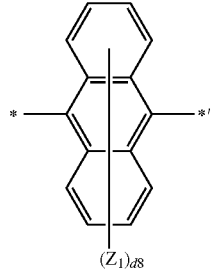

Formula 3-8

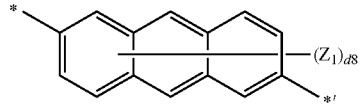

Formula 3-9

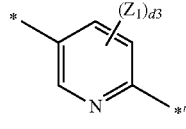

Formula 3-10

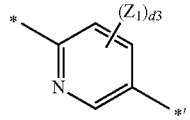

Formula 3-11

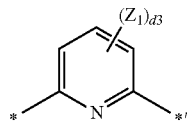

Formula 3-12

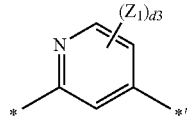

Formula 3-13

-continued
Formula 3-14
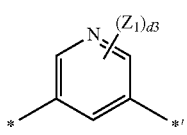
Formula 3-15
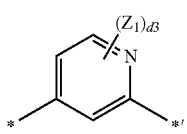
Formula 3-16
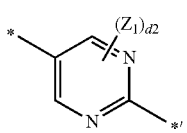
Formula 3-17
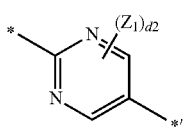
Formula 3-18
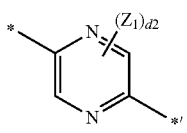
Formula 3-19
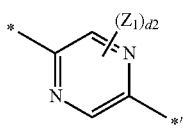
Formula 3-20
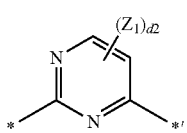
Formula 3-21
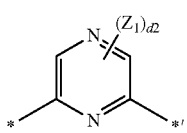
Formula 3-22
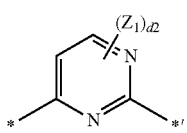
Formula 3-23
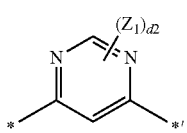
Formula 3-24
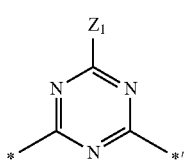
-continued
Formula 3-25
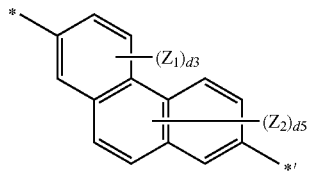
Formula 3-26
Formula 3-27
Formula 3-28
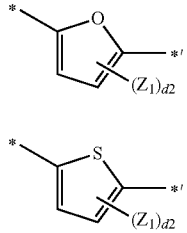
Formula 3-29
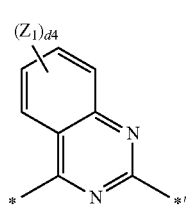
Formula 3-30
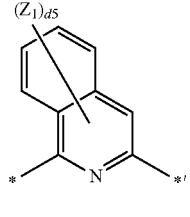
Formula 3-31
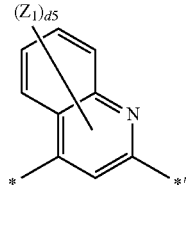
Formula 3-32
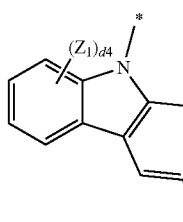
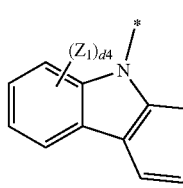

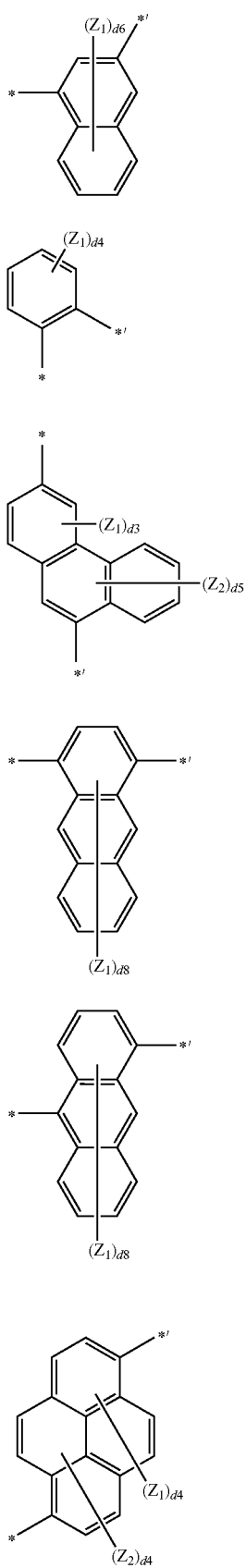
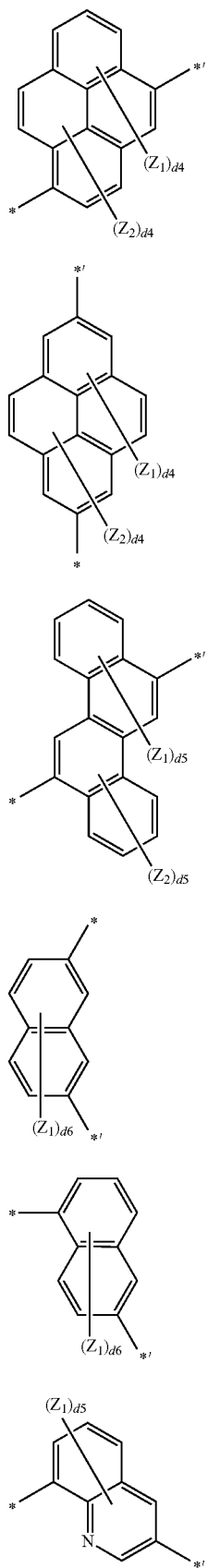

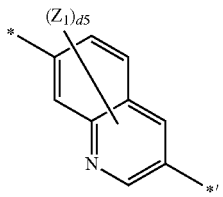

Formula 3-45

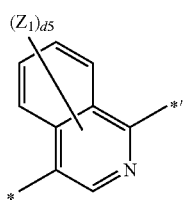

Formula 3-46

In Formulae 3-1 to 3-46, $Y_1$ may be O, S, $C(Z_3)(Z_4)$, $N(Z_5)$, or $Si(Z_6)(Z_7)$, $Z_1$ to $Z_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenylcarbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$ d2 may be an integer from 0 to 2,
d3 may be an integer from 0 to 3,
d4 may be an integer from 0 to 4,
d5 may be an integer from 0 to 5,
d6 may be an integer from 0 to 6,
d8 may be an integer from 0 to 8, when d2 is 2, two $Z_1$(s) may be identical to or different from each other, when d3 is 2 or more, two or more $Z_1$(s) and two or more $Z_2$(s) may be identical to or different from each other, when d4 is 2 or more, two or more $Z_1$(s) and two or more $Z_2$(s) may be identical to or different from each other, when d5 is 2 or more, two or more $Z_1$(s) and two or more $Z_2$(s) may be identical to or different from each other, when d6 is 2 or more, two or more $Z_1$(s) and two or more $Z_2$(s) may be identical to or different from each other, when d8 is 2 or more, two or more $Z_1$(s) may be identical to or different from each other, $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

* and *' each indicate a binding site to a neighboring atom.

In one embodiment, $R_3$, $R_4$, $R_5$, $R_6$, $R_7$, $R_8$, $R_{10}$, $R_{20}$, $R_{30}$, $R_{40}$, $R_{50}$, and $R_{60}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group:

cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, a pyridoindolyl group, an indazolyl group, a purinyl group, a quinolinyl group, an isoquinolinyl group, a benzoquholinyl group, a phthalazinyl group, a naphthyndinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, a pyridoindolyl group, an indazolyl group, a purinyl group, a quinolinyl group, an isoquinolinyl group, a benzoquholinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group a cyclohexenyl group, a phenyl group, a biphenyl group, a terphenyl group, a pentalenyl group, an indenyl group, a naphthyl group, an azulenyl group, a heptalenyl group an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), and $Q_1$ to $Q_3$ and $Q_{31}$ to $Q_{33}$ may each independently be selected from:

a $C_1$-$C_{20}$ alkyl group, a $C_1$-$C_{20}$ alkoxy group, a phenyl group, a biphenyl group, and a terphenyl group; and a phenyl group substituted with at least one selected from —F, —Cl, —Br, —I, a cyano group, a $C_1$-$C_{20}$ alkyl group, and a $C_1$-$C_{20}$ alkoxy group.

In one embodiment, $R_4$, $R_5$, $R_7$, $R_8$, $R_{30}$, $R_{40}$, $R_{50}$, and $R_{60}$ may each independently be selected from:

hydrogen, deuterium, —F, —Cl, —Br, —I, a methyl group, an ethyl group, an n-propyl group, an isopropyl group, an n-butyl group, a sec-butyl group, an isobutyl group, a tert-butyl group, an ethenyl group, a propenyl group, a butenyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group; and a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group, each substituted with at least one selected from deuterium, —F, —Cl, —Br, —I, a cyano group, a phenyl group, and a biphenyl group, and $R_3$, $R_6$, $R_{10}$, and $R_{20}$ may each independently be selected from groups represented by Formulae 5-1 to 5-32:

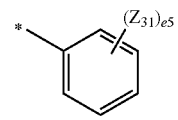

Formula 5-1

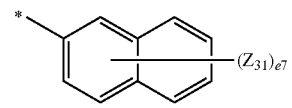

Formula 5-2

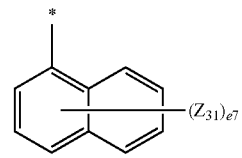

Formula 5-3

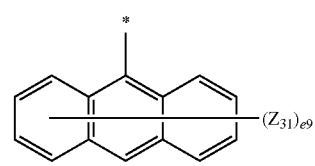

Formula 5-4

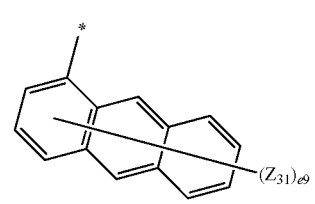

Formula 5-5

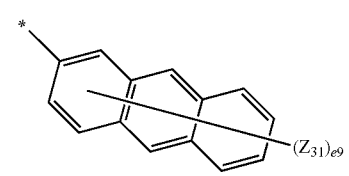

Formula 5-6

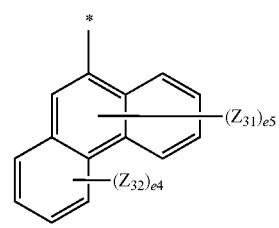

Formula 5-7

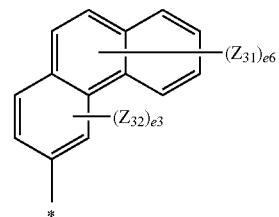

Formula 5-8

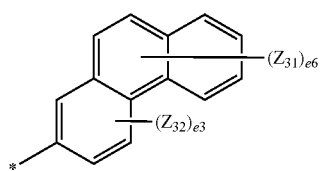
Formula 5-9
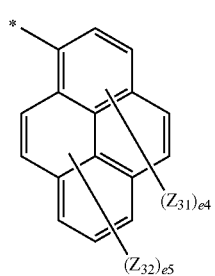
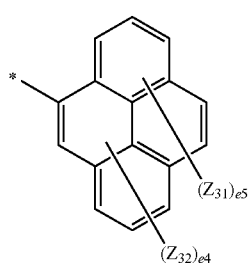
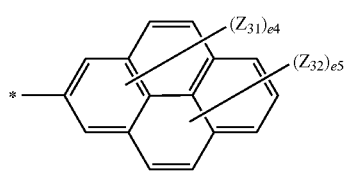
Formula 5-12
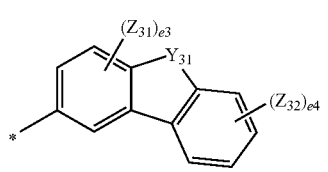
Formula 5-13
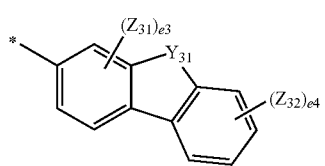
Formula 5-14
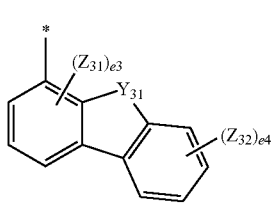
Formula 5-15
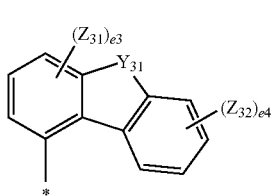
Formula 5-16
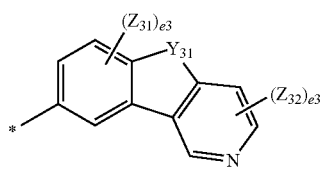
Formula 5-17
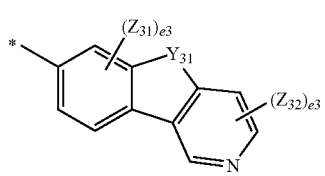
Formula 5-18
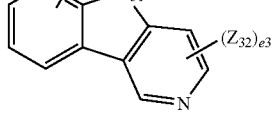
Formula 5-19
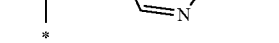
Formula 5-20
Formula 5-21
Formula 5-22
Formula 5-23
Formula 5-24
Formula 5-25

-continued

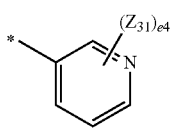
Formula 5-26

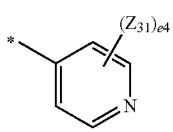
Formula 5-27

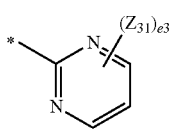
Formula 5-28

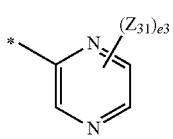
Formula 5-29

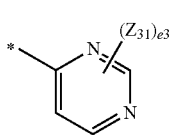
Formula 5-30

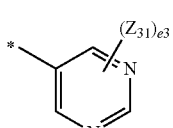
Formula 5-31

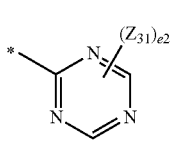
Formula 5-32

In Formulae 5-1 to 5-32, $Y_{31}$ may be O, S, $C(Z_{33})(Z_{34})$, $N(Z_{35})$, $Si(Z_{36})(Z_{37})$, or $P(=O)(Z_{38})$, $Z_{31}$ to $Z_{38}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spirofluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$Si(Q_{31})(Q_{32})(Q_{33})$, and $P(=O)(Q_{31})(Q_{32})$, and $Q_1$ to $Q_3$ and $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group.

In Formulae 5-1 to 5-32, e2 may be an integer from 0 to 2,
e3 may be an integer from 0 to 3,
e4 may be an integer from 0 to 4,
e5 may be an integer from 0 to 5,
e6 may be an integer from 0 to 6,
e7 may be an integer from 0 to 7,
e9 may be an integer from 0 to 9, when e2 is two, two or more $Z_{31}(S)$ may be identical to or different from each other, when e3 is two or more, two or more $Z_{31}(S)$ and two or more $Z_{32}(s)$ may be identical to or different from each other, when e4 is two or more, two or more $Z_{31}(S)$ and two or more $Z_{32}(s)$ may be identical to or different from each other, when e5 is two or more, two or more $Z_{31}(S)$ and two or more $Z_{32}(s)$ may be identical to or different from each other, when e6 is two or more, two or more $Z_{31}(S)$ and two or more $Z_{32}(s)$ may be identical to or different from each other, when e7 is two or more, two or more $Z_{31}(S)$ may be identical to or different from each other, when e9 is two or more, two or more $Z_{31}(S)$ may be identical to or different from each other, and

* indicates a binding site to a neighboring atom.

For example, $R_4$, $R_5$, $R_7$, $R_8$, $R_{30}$, $R_{40}$, $R_{50}$, and $R_{60}$ may each independently be selected from:

hydrogen, a methyl group, an ethyl group, an n-propyl group, an isopropyl group, a methoxy group, an ethoxy group, an n-propoxy group, an isopropoxy group, a phenyl group, a biphenyl group, and a naphthyl group; and a methyl group, an ethyl group, an n-propyl group, an isopropyl group, a methoxy group, an ethoxy group, an n-propoxy group, an isopropoxy group, a phenyl group, a biphenyl group, and a naphthyl group, each substituted with at least one selected from a phenyl group and a biphenyl group.

For example, $R_3$, $R_6$, $R_{10}$, and $R_{20}$ may each independently be selected from groups represented by Formulae 6-1 to 6-50:

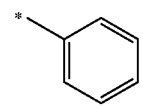
Formula 6-1

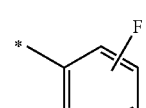
Formula 6-2

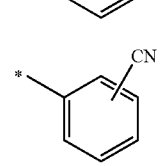
Formula 6-3

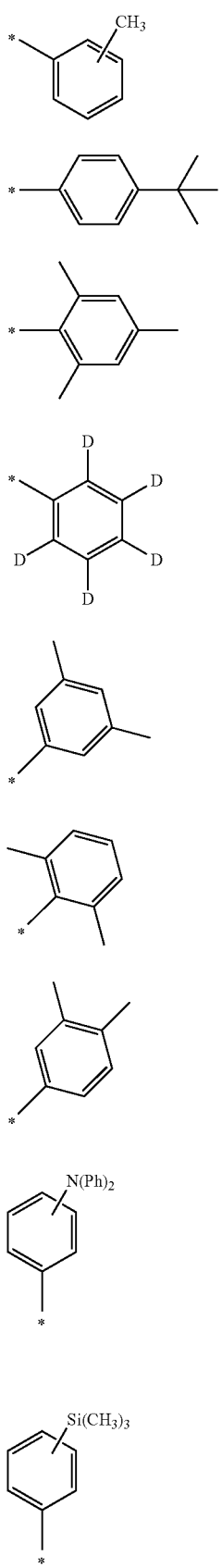
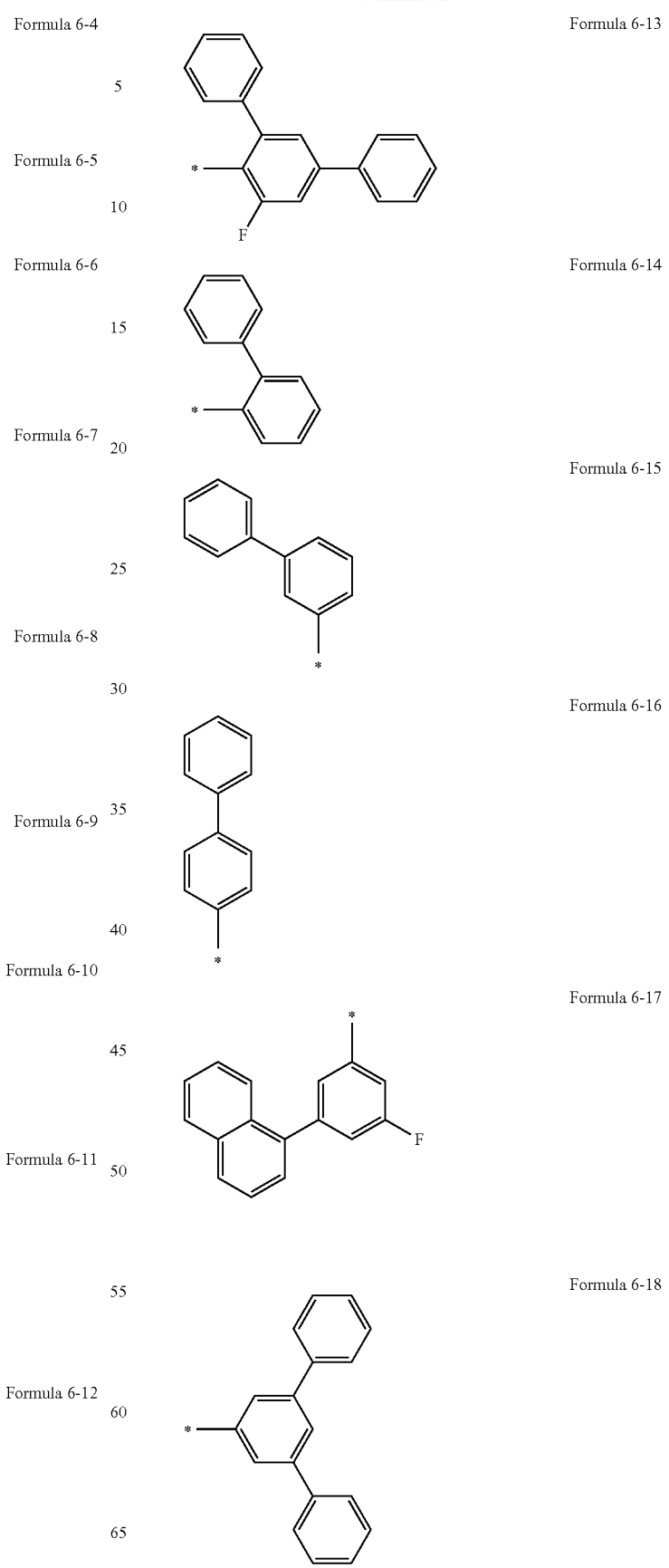

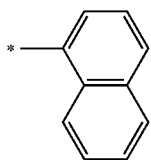
Formula 6-19
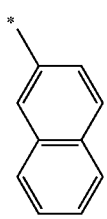
Formula 6-20
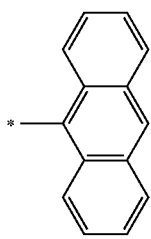
Formula 6-21
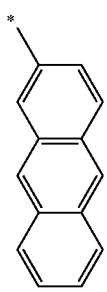
Formula 6-22
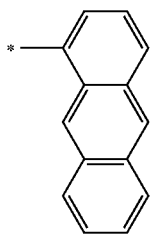
Formula 6-23
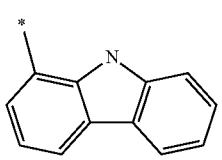
Formula 6-23
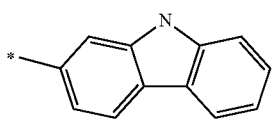
Formula 6-24
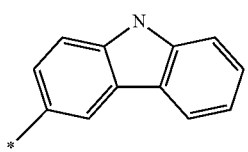
Formula 6-25
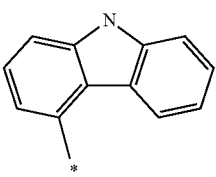
Formula 6-26
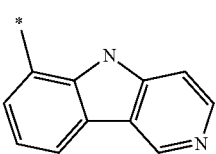
Formula 6-27
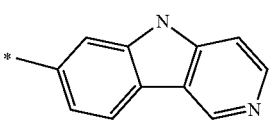
Formula 6-28
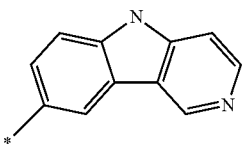
Formula 6-29
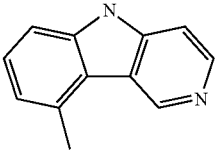
Formula 6-30
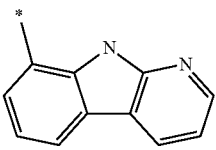
Formula 6-31
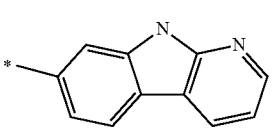
Formula 6-32
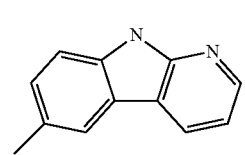
Formula 6-33
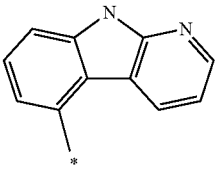
Formula 6-34

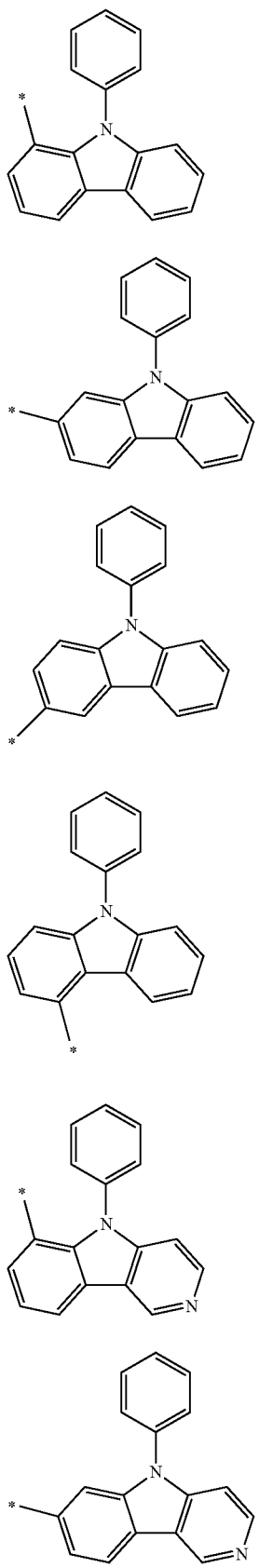
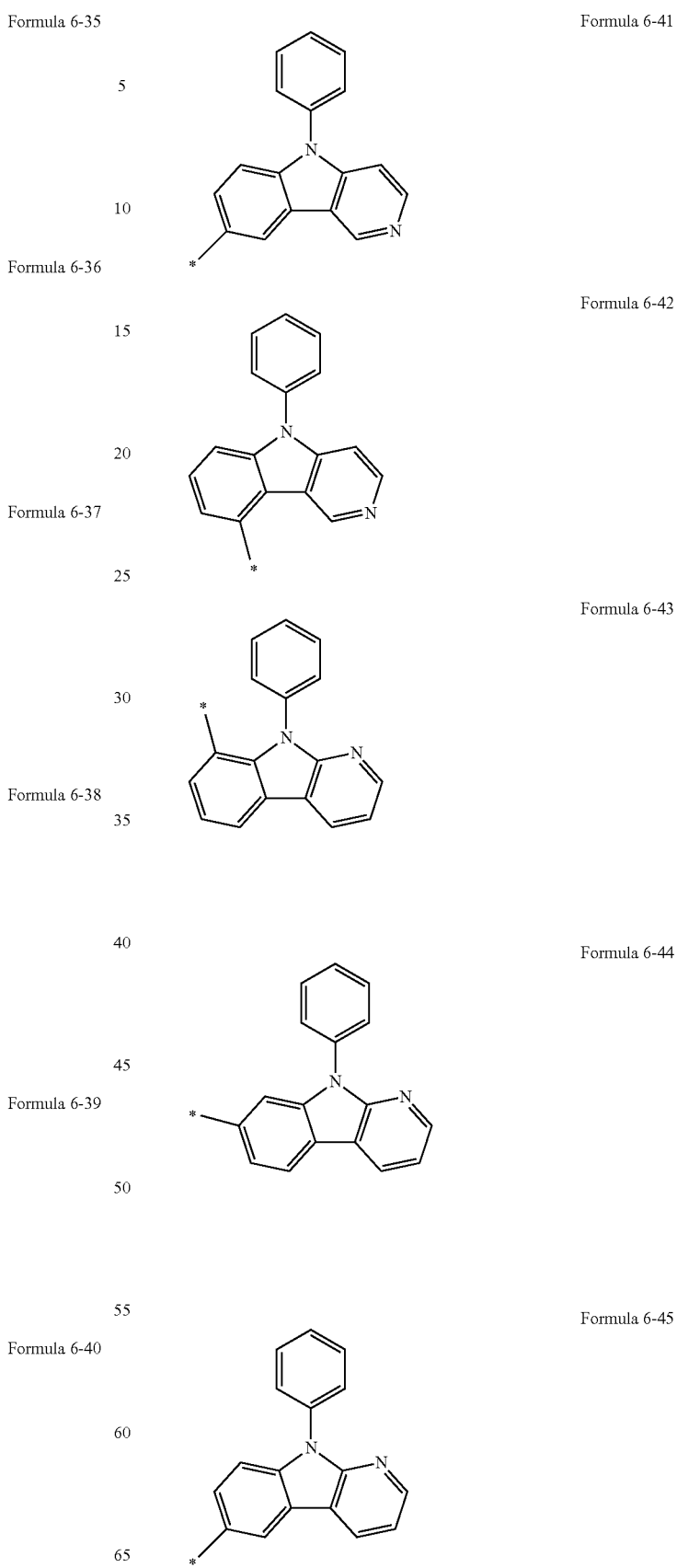
Formula 6-35
Formula 6-36
Formula 6-37
Formula 6-38
Formula 6-39
Formula 6-40
Formula 6-41
Formula 6-42
Formula 6-43
Formula 6-44
Formula 6-45

-continued

Formula 6-46

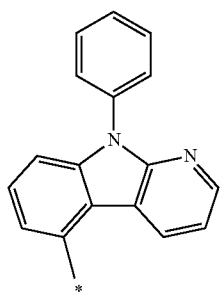

Formula 6-47

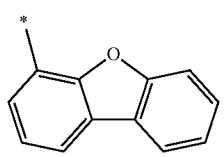

Formula 6-48

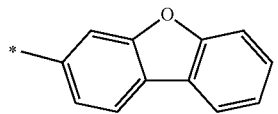

Formula 6-49

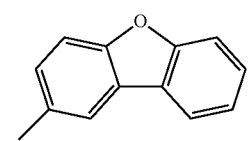

Formula 6-50

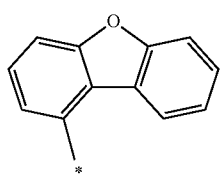

In Formulae 6-1 to 6-50, * indicates a binding site to a neighboring atom.

In one embodiment, the compound of Formula 1 may be represented by one selected from Formulae 1-1 to 1-3:

Formula 1-1

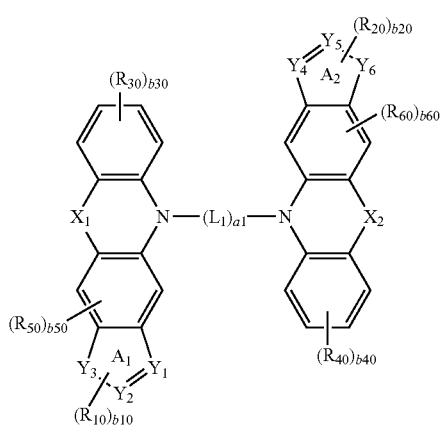

Formula 1-2

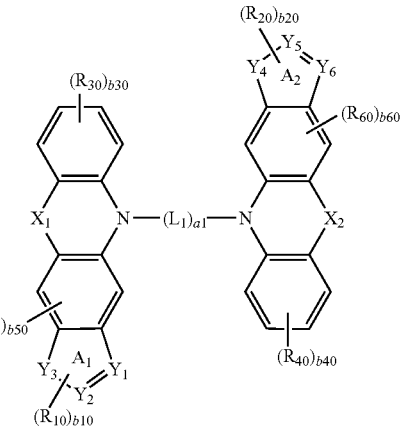

Formula 1-3

In Formulae 1-1 to 1-3, $X_1$, $X_2$, $A_1$, $A_2$, $R_{10}$, $R_{20}$, $R_{30}$, $R_{40}$, $R_{50}$, a1, b10, b20, b30, b40, b50, and b60 may each independently be the same as defined in connection with Formula 1.

In one embodiment, $Y_1$, $Y_2$, $Y_3$, $Y_4$, $Y_5$, and $Y_6$ may each independently be N, O or S when connected to a single bond only, and/or may each independently be N or C when connected to a double bond. For example, ($Y_1$, $Y_2$, $Y_3$) in Formula 1-1 may be (C,C,N), (N,C,N), (C,C,O), (C,C,S), (N,C,O), or (N,C,S). In some embodiments of Formula 1-1, ($Y_4$, $Y_5$, $Y_6$) may be (C,C,N) or (N,C,N), for example, $Y_3$ and $Y_6$ may be N. In some embodiments of Formula 1-2, ($Y_1$, $Y_2$, $Y_3$) may be (C,C,N), (C,C,O) or (N,C,N) and ($Y_4$, $Y_5$, $Y_6$) may be (N,C,C) or (N,C,N), for example, $Y_3$ is N or O and $Y_4$ is N. In some embodiments of Formula 1-3, ($Y_1$, $Y_2$, $Y_3$) may be (N,C,C) or (N,C,N) and ($Y_4$, $Y_5$, $Y_6$) may be (N,C,C) or (N,C,N), for example, $Y_1$ and $Y_4$ are N.

In one embodiment, $L_1$ may be selected from:

a phenylene group, a naphthylene group, a fluorenylene group, an anthracenylene group, a pyridinylene group, a carbazolylene group, a dibenzofuranylene group, a dibenzothiophenylene group, a dibenzosilolylene group, and a pyridoindolylene group; and a phenylene group, a naphthylene group, a fluorenylene group, an anthracenylene group, a pyridinylene group, a carbazolylene group, a dibenzofuranylene group, a dibenzothiophenylene group, a dibenzosilolylene group, and a pyridoindolylene group, each substituted with at least one selected from deuterium, —F, —Cl, —Br, —I, a $C_1$-$C_{20}$ alkyl group, a $C_1$-$C_{20}$ alkoxy group, a phenyl group, a biphenyl group, a naphthyl group, a carbazolyl group, and a phenylcarbazolyl group.

In one embodiment, $R_4$, $R_5$, $R_7$, $R_8$, $R_{30}$, $R_{40}$, $R_{50}$, and $R_{60}$ may each independently be selected from hydrogen, deuterium, —F, —Cl, —Br, —I, a methyl group, an ethyl group, an n-propyl group, an isopropyl group, an n-butyl group, a sec-butyl group, an isobutyl group, a tert-butyl group, an ethenyl group, a propenyl group, a butenyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group, and $R_3$, $R_6$, $R_{10}$, and $R_{20}$ may each independently be selected from:

a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group; and a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group.

In one or more embodiments, $(L_1)_{a1}$ may be selected from groups represented by Formulae 4-1 to 4-14:

4-1

4-2
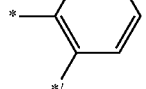

4-3
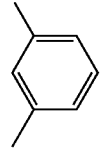

4-4
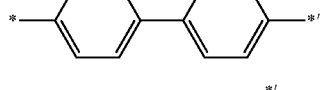

4-5
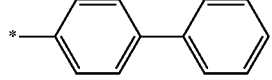

4-6
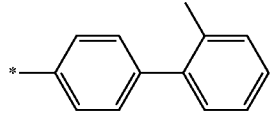

-continued 4-7
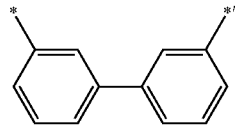

4-8
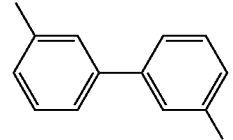

4-9
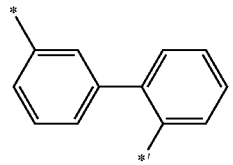

4-10
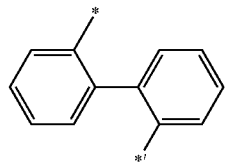

4-11
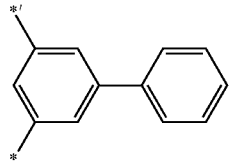

4-12
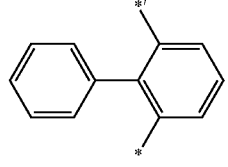

4-13
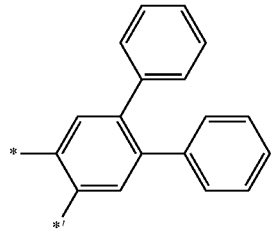

4-14
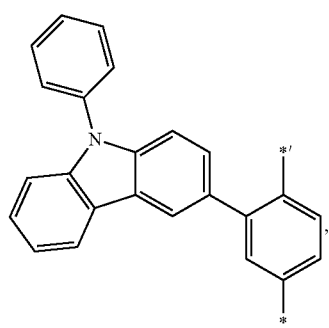

$R_4$, $R_5$, $R_7$, $R_8$, $R_{30}$, $R_{40}$, $R_{50}$, and $R_{60}$ may each independently be selected from hydrogen, a methyl group, an ethyl group, an n-propyl group, an isopropyl group, a methoxy group, an ethoxy group, an n-propoxy group, an isopropoxy group, a phenyl group, a biphenyl group, and a naphthyl group, and $R_3$, $R_6$, $R_{10}$, and $R_{20}$ may each independently be selected from:

a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group; and a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group, each substituted with at least one selected from a phenyl group, a biphenyl group, and a naphthyl group.

For example, the heterocyclic compound may be selected from Compounds 1 to 33:

1

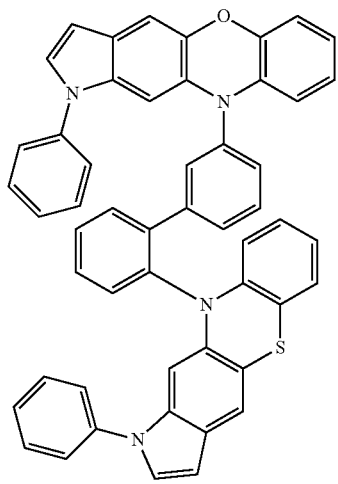

2

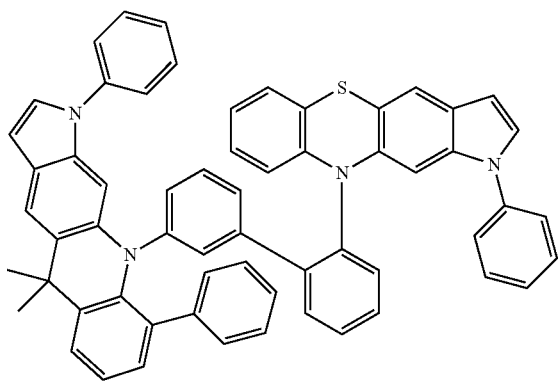

3

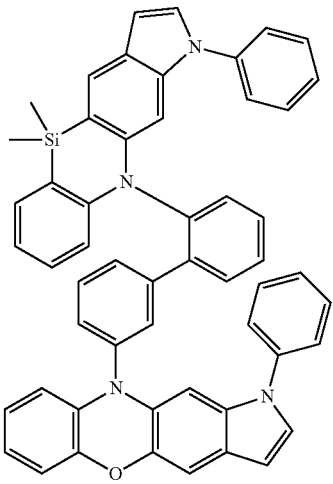

4

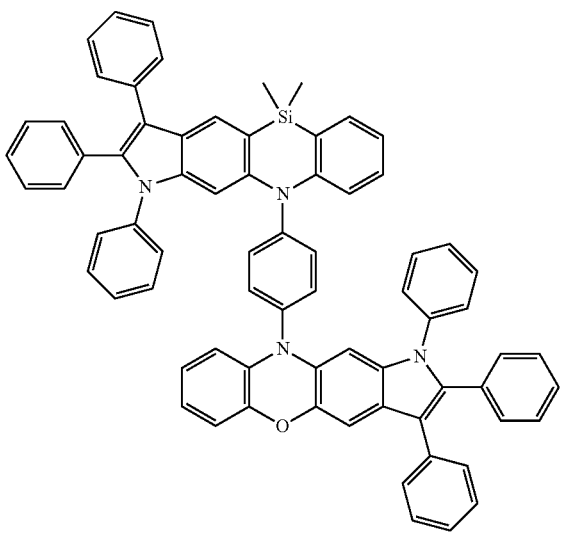

5

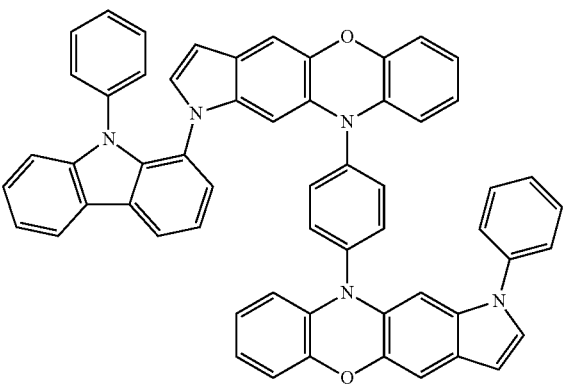

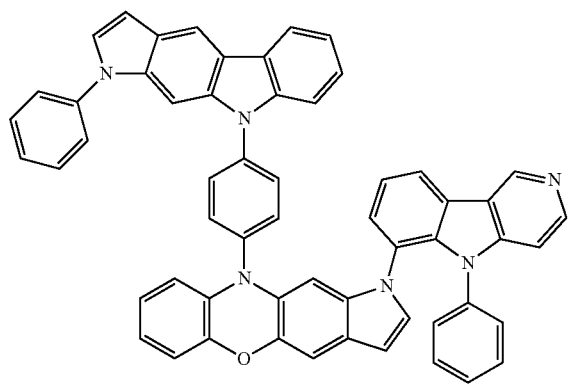
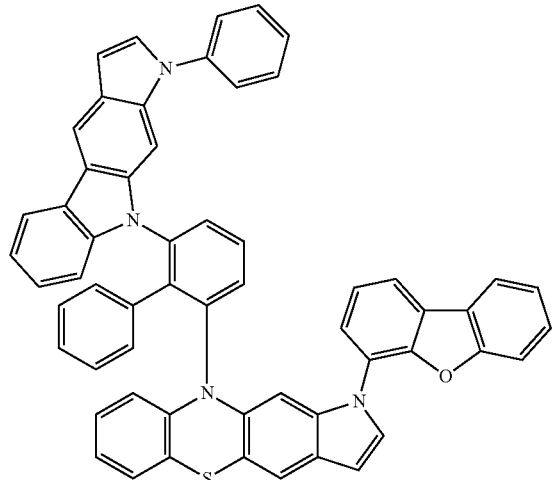
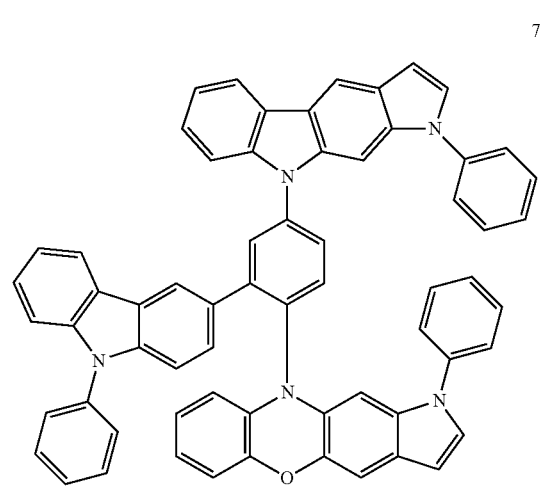
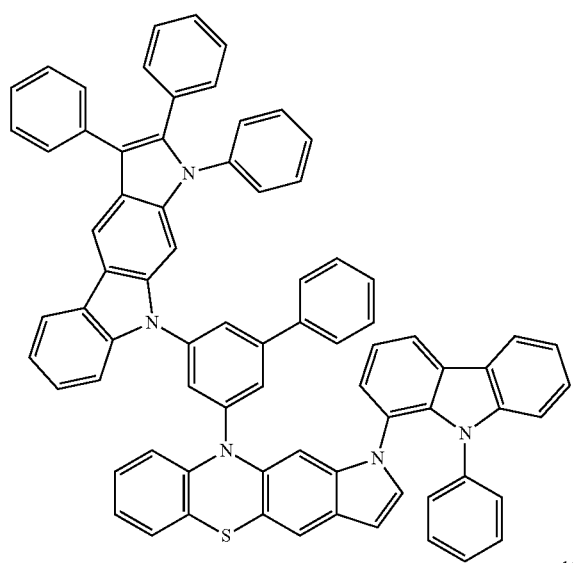
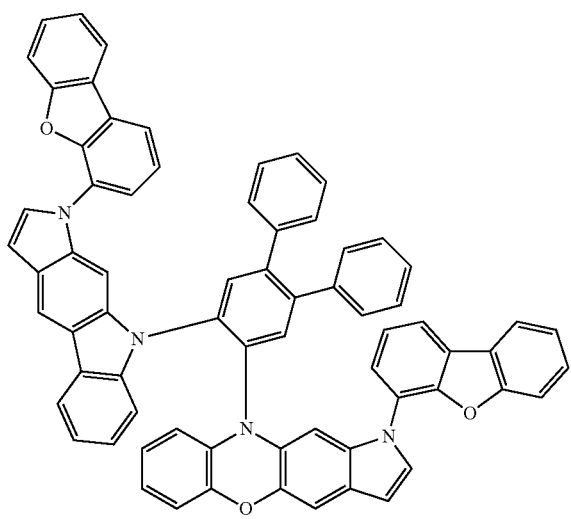
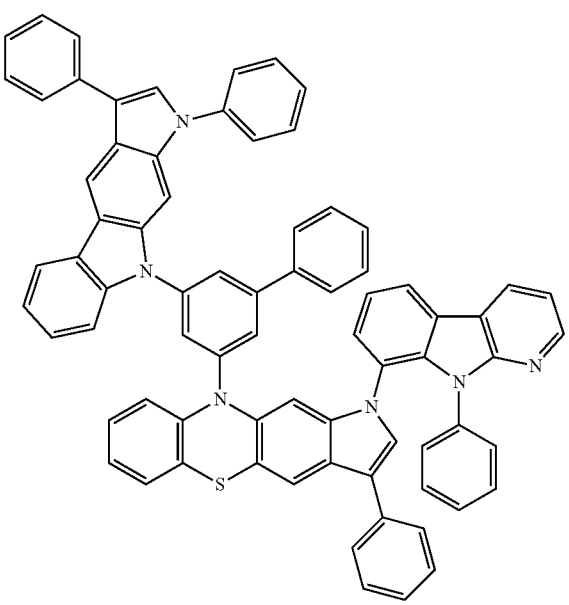

12
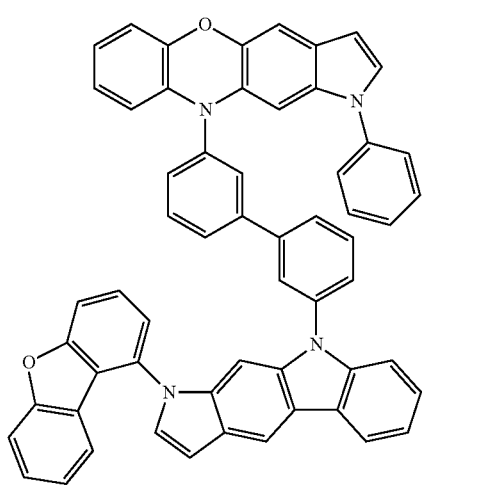
13
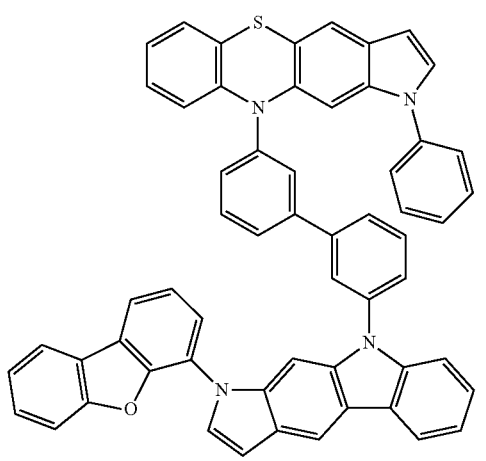
14
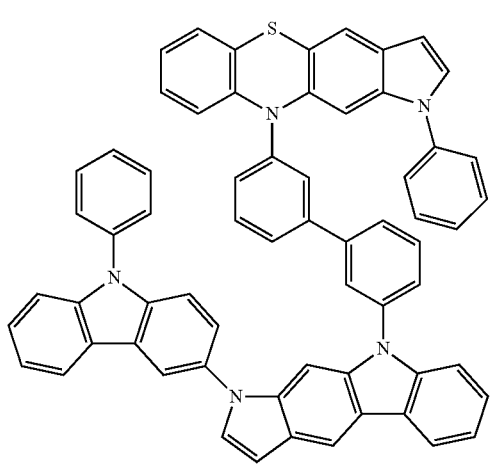
15
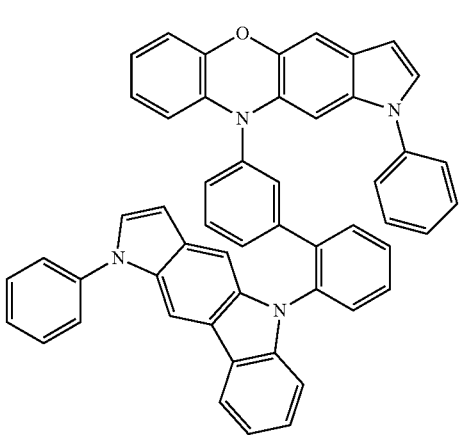
16
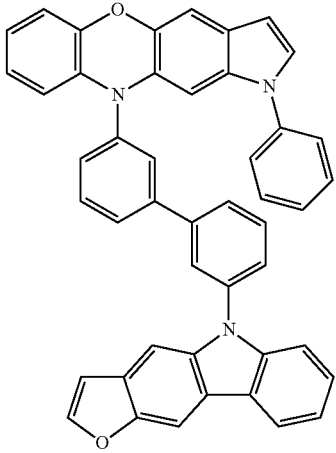
17
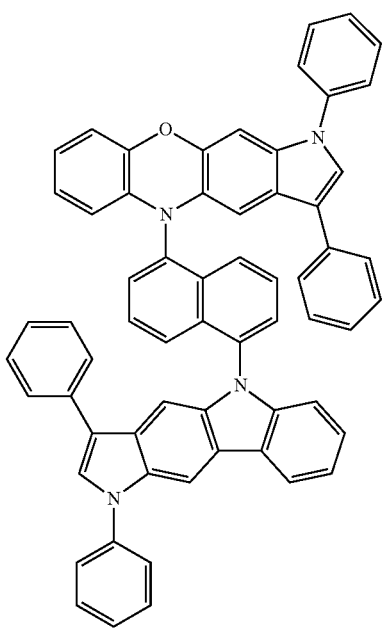

18
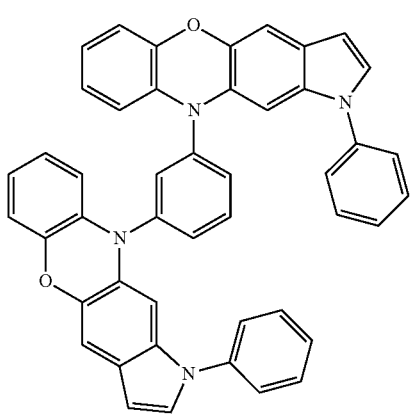
19
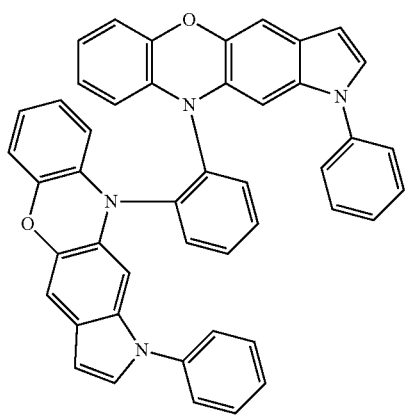
20
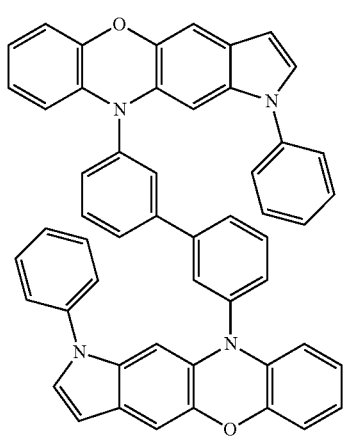
21
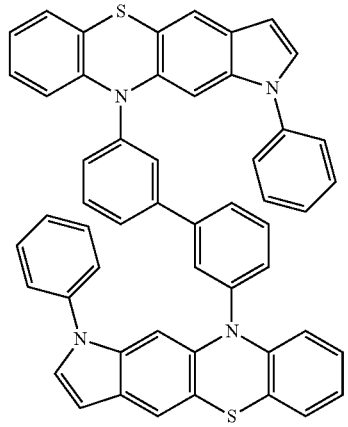
22
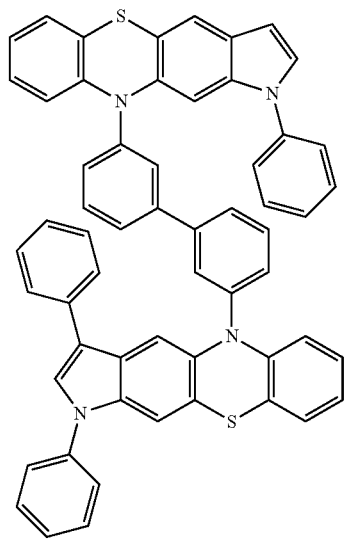
23
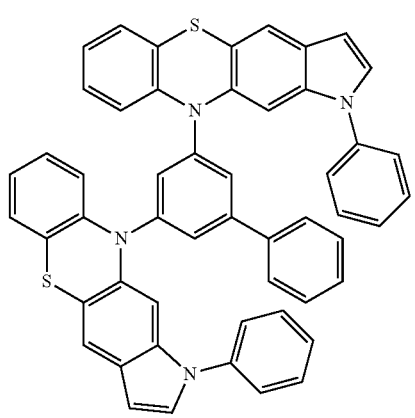

-continued
24
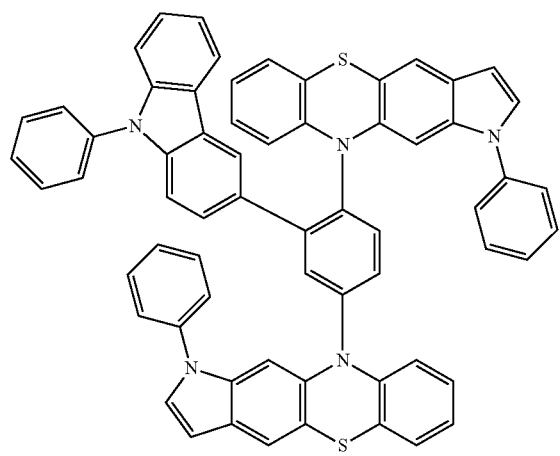
25
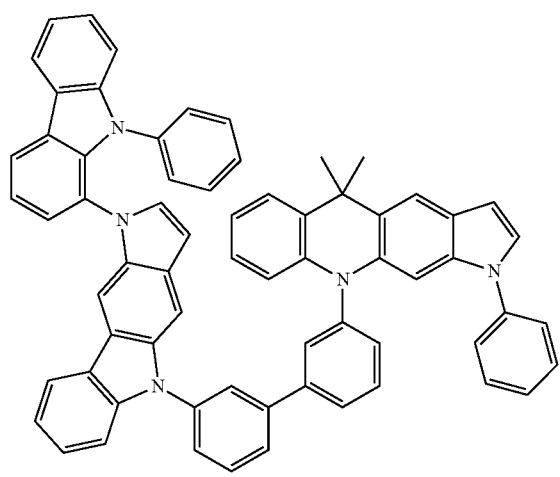
26
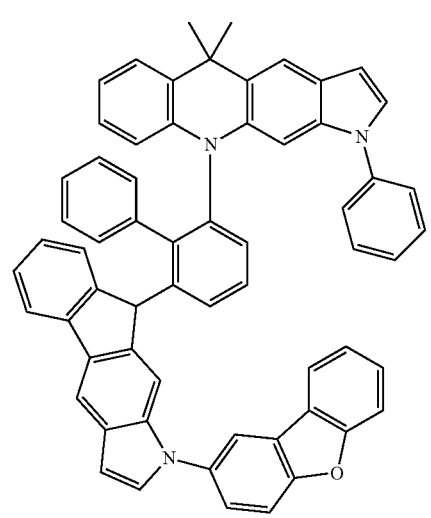
-continued
27
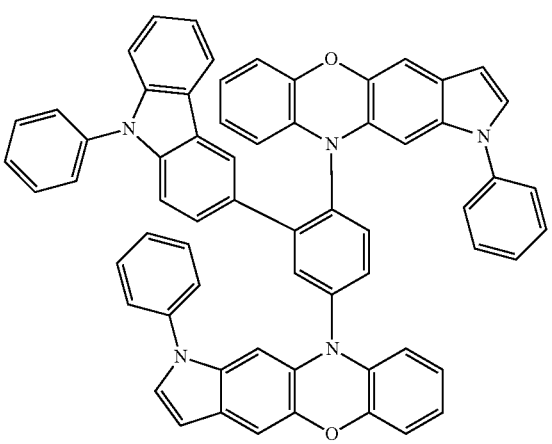
28
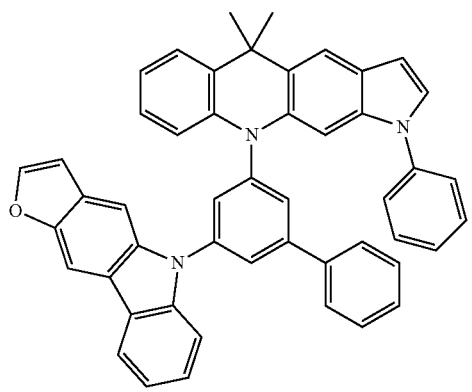
29

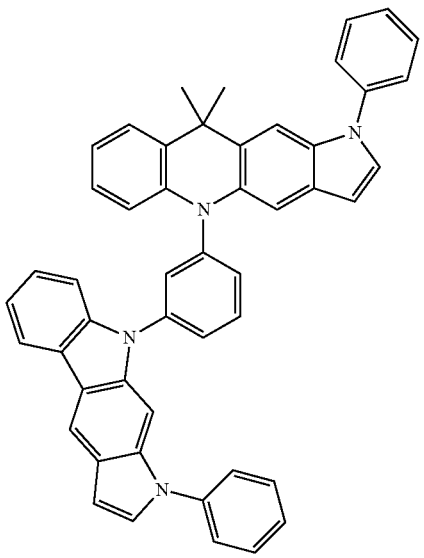

30

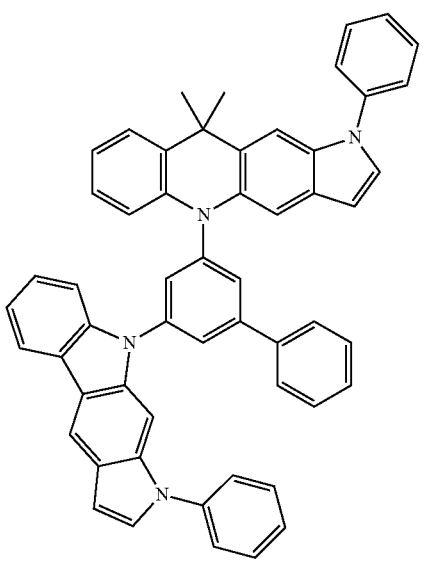

31

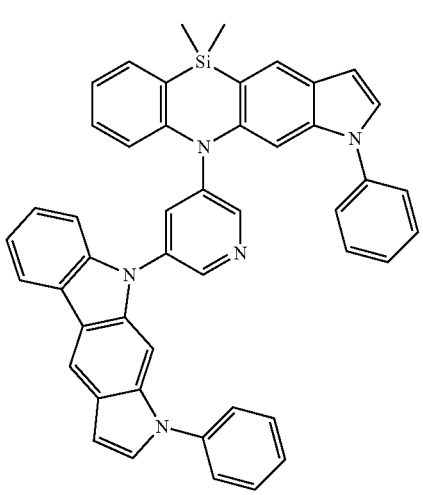

32

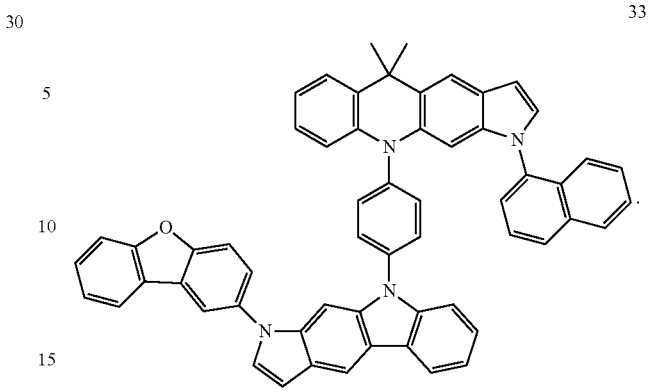

33

The heterocyclic compound has a structure having a strong electron-donating property and has an effect of improving hole injection capability. When the heterocyclic compound is used as a material for forming an organic light-emitting device, the luminescence efficiency and quantum efficiency may be improved. In addition, the heterocyclic compound has a high triplet energy level and prevents or reduces diffusion of triplet excitons produced in the emission layer into other layers, thereby improving the luminescence efficiency. Therefore, the heterocyclic compound may be used as blue phosphorescence host and a thermally activated delayed fluorescence (TADF) host.

At least one of the heterocyclic compound of Formula 1 may be used between a pair of electrodes of an organic light-emitting device. For example, the heterocyclic compound may be included in at least one layer selected from a hole transport region, an electron transport region, and an emission layer. In one or more embodiments, the heterocyclic compound of Formula 1 may be used as a material for a capping layer located outside a pair of electrodes of an organic light-emitting device.

Accordingly, another aspect of an embodiment of the present disclosure provides an organic light-emitting device including: a first electrode; a second electrode facing the first electrode, and an organic layer between the first electrode and the second electrode, the organic layer including an emission layer and at least one of the heterocyclic compound represented by Formula 1.

The expression "(an organic layer) includes at least one of the heterocyclic compounds," as used herein, may include a case in which "(an organic layer) includes identical heterocyclic compounds represented by Formula 1" and/or a case in which "(an organic layer) includes two or more different heterocyclic compounds represented by Formula 1".

For example, the organic layer may include, as the heterocyclic compound, only Compound 1. In this regard, Compound 1 may exist (e.g., be present) only in the emission layer of the organic light-emitting device. In one or more embodiments, the organic layer may include, as the heterocyclic compound, Compound 1 and Compound 2. In this regard, Compound 1 and Compound 2 may exist (e.g., be present) in an identical layer (for example, Compound 1 and Compound 2 may all exist in an emission layer), or different layers (for example, Compound 1 may exist in an emission layer and Compound 2 may exist (e.g., be present) in a hole transport layer).

In one embodiment, the first electrode may be an anode, the second electrode may be a cathode, and the organic layer may further include a hole transport region between the first electrode and the emission layer and an electron transport region between the emission layer and the second electrode, wherein the hole transport region may include a hole injection layer, a hole transport layer, an emission auxiliary layer, an electron blocking layer, or any combination thereof, and the electron transport region may include a hole blocking layer, an electron transport layer, an electron injection layer, or any combination thereof.

In one or more embodiments, the emission layer of the organic light-emitting device may include the heterocyclic compound.

In one or more embodiments, the heterocyclic compound included in the emission layer of the organic light-emitting device may be a thermally activated delayed fluorescence (TADF) emitter, and in this regard, the emission layer may emit TADF.

In one or more embodiments, the emission layer of the organic light-emitting device may include a host and a dopant, and the host may include the heterocyclic compound. The dopant may include a phosphorous dopant or a fluorescent dopant.

In one or more embodiments, the emission layer of the organic light-emitting device may include (e.g., consist of) the heterocyclic compound, or may further include a host, wherein an amount of the host is in a range of about 0.1 parts by weight to about 50 parts by weight based on 100 parts by weight of the emission layer.

The host included in the emission layer may include at least one selected from an anthracene-based compound, a pyrene-based compound, and a spiro-bifluorene-based compound, but embodiments of the present disclosure are not limited thereto.

In one embodiment, the hole transport region of the organic light-emitting device may include a p-dopant having a lowest unoccupied molecular orbital (LUMO) energy level of −3.5 eV or less.

In one embodiment, the electron transport region of the organic light-emitting device may include at least one selected from a phosphine oxide-based compound and benzimidazole-based compound, and may further include an alkali metal, alkaline earth metal, a rare earth metal, an alkali metal compound, alkaline earth metal compound, a rare earth metal compound, an alkali metal complex, alkaline earth metal complex, a rare earth metal complex, or any combination thereof.

The term "organic layer," as used herein, refers to a single layer and/or a plurality of layers between the first electrode and the second electrode of the organic light-emitting device. A material included in the "organic layer" is not limited to an organic material. For example, the organic layer may include an inorganic material.

Description of FIG. 1

Figure 1:
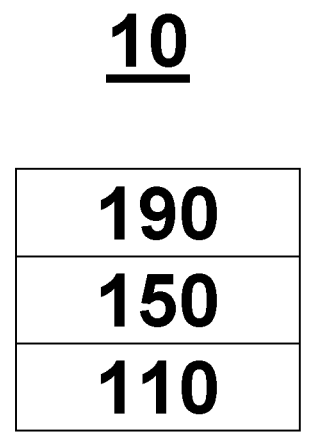

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

In FIG. 1, a substrate may be additionally under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-reflective electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 may be on the first electrode 110. The organic layer 150 may include an emission layer.

The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrene-sulfonate) (PANI/PSS), a compound represented by Formula 201, and a compound represented by Formula 202:

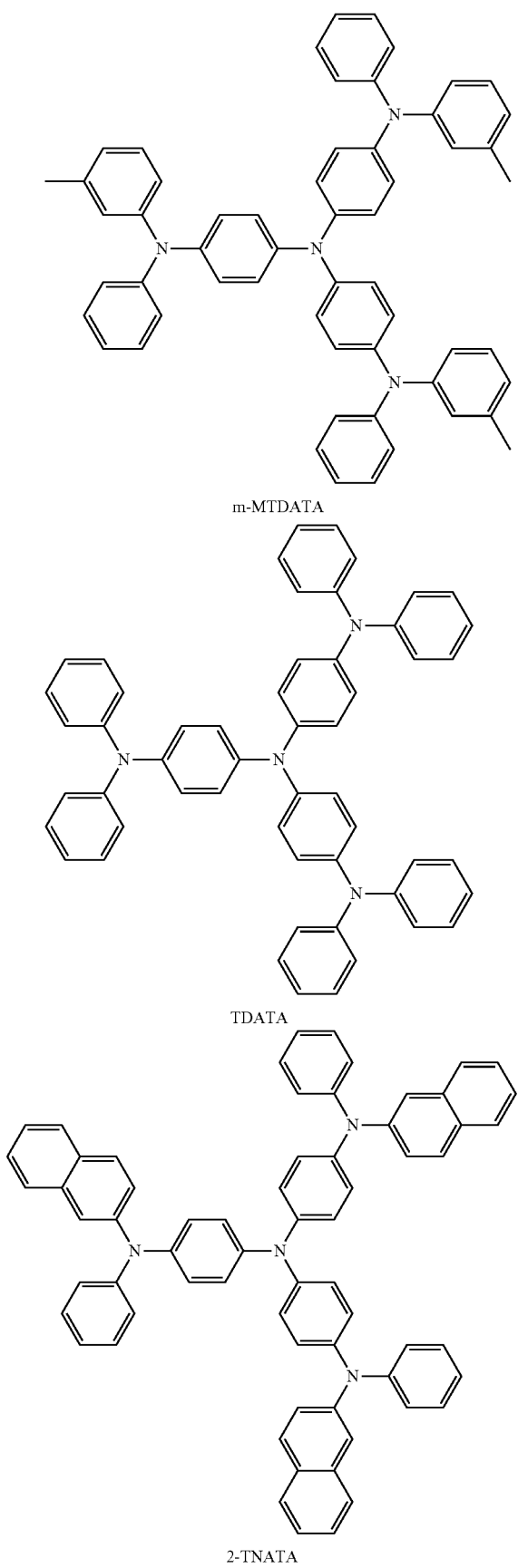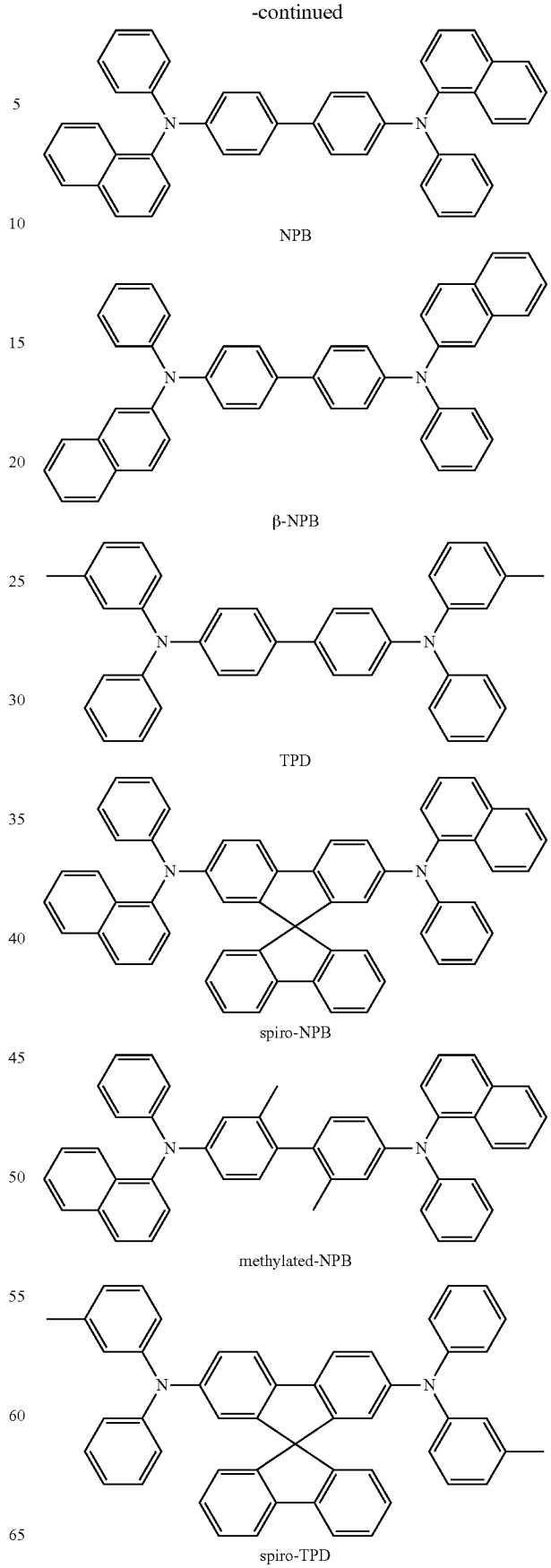

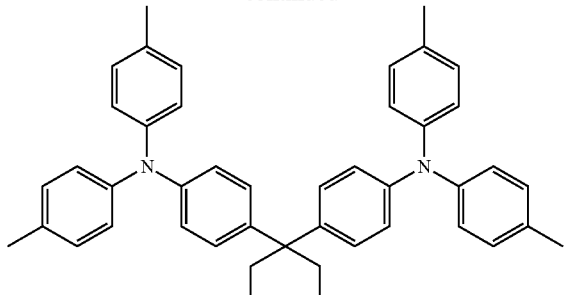

TAPC

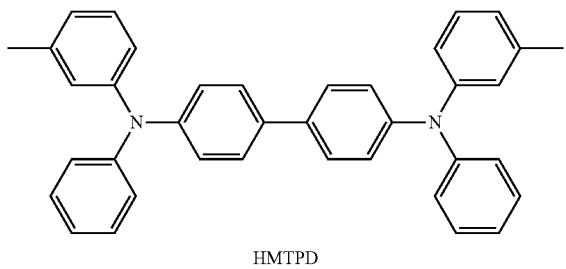

HMTPD

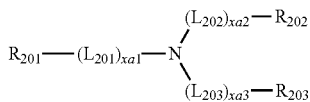

Formula 201

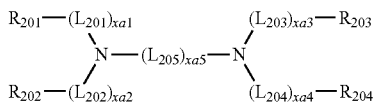

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $R_{201}$ and $R_{202}$ in Formula 202 may optionally be linked via a single bond, a dimethyl-methylene group, or a diphenyl-methylene group, $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from;

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may each independently be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

Formula 201A

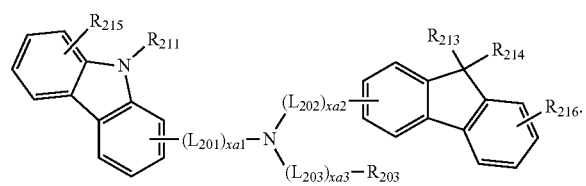

In one embodiment, the compound represented by Formula 201 may be represented by Formula 201A(1), but embodiments of the present disclosure are not limited thereto:

Formula 201A(1)

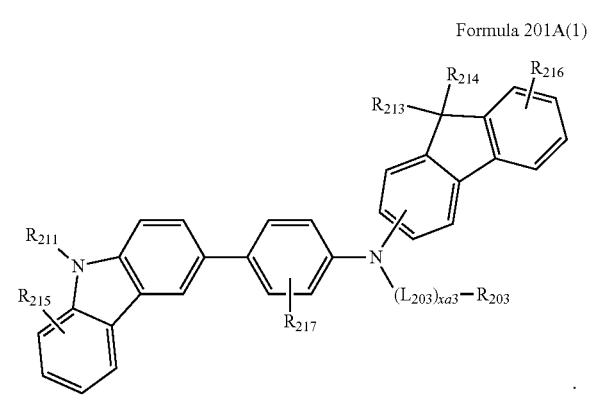

In one or more embodiments, the compound represented by Formula 201 may be represented by Formula 201A-1, but embodiments of the present disclosure are not limited thereto:

Formula 201A-1

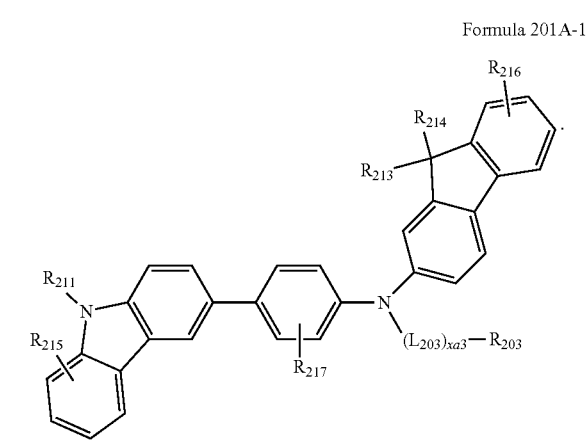

In one embodiment, the compound represented by Formula 202 may be represented by Formula 202A:

Formula 202A

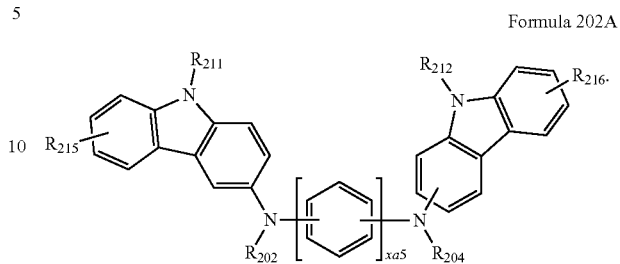

In one or more embodiments, the compound represented by Formula 202 may be represented by Formula 202A-1:

Formula 202A-1

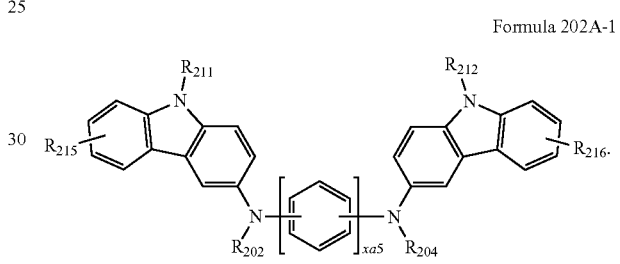

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may each independently be the same as defined in connection with $R_{203}$, and $R_{213}$ to $R_{217}$ may each independently be selected from hydrogen, deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.
The hole transport region may include at least one compound selected from Compounds HT1 to HT39, but embodiments of the present disclosure are not limited thereto:
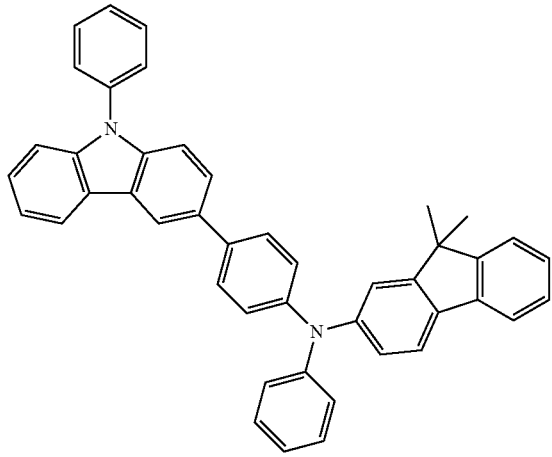
HT1
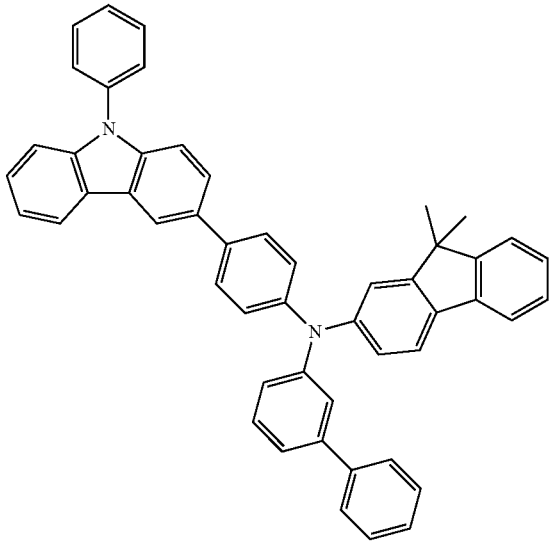
HT2
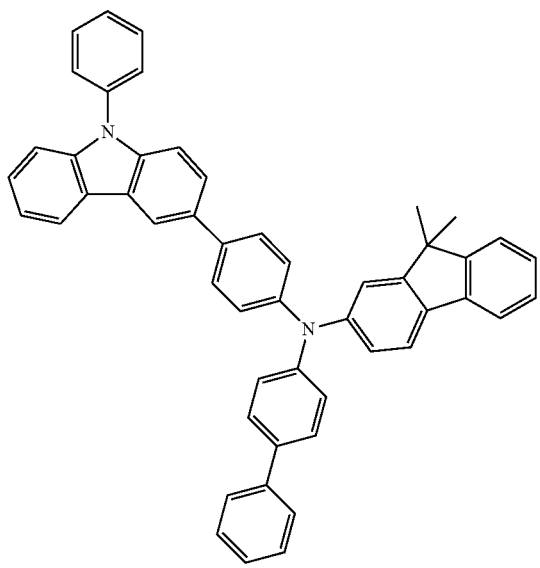
HT3
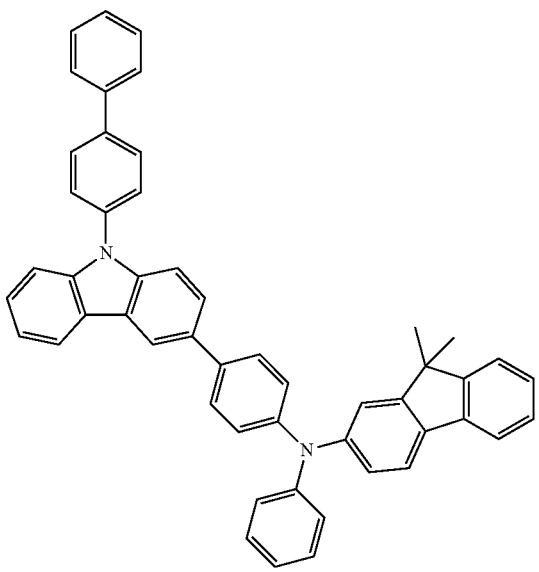
HT4

-continued
HT5
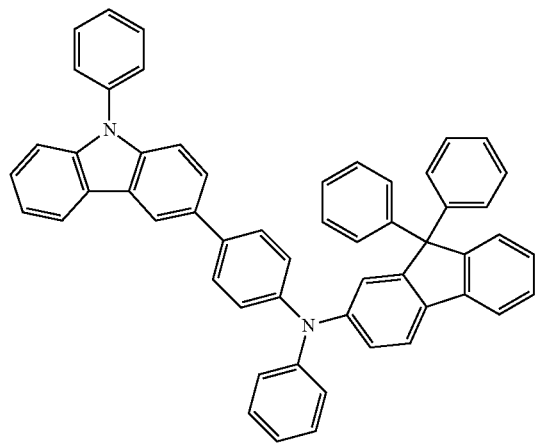
HT6
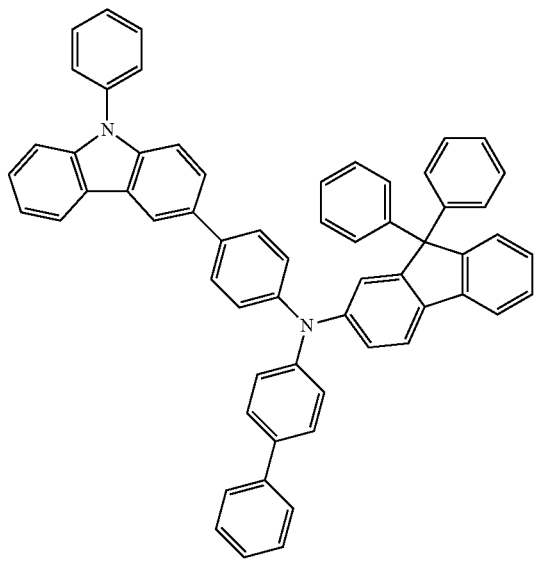
HT7
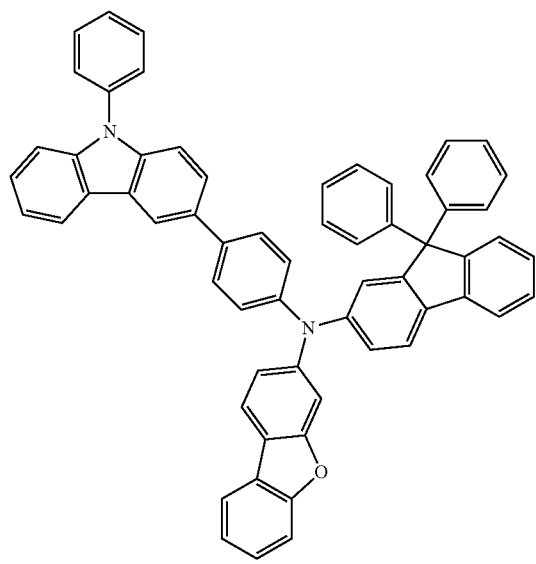
HT8
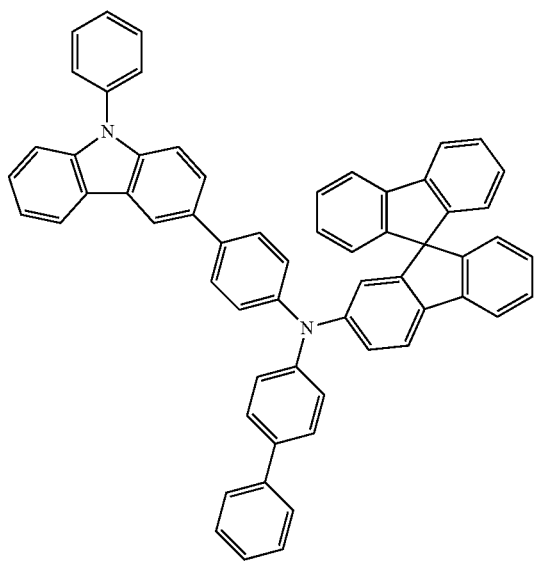

-continued
HT9
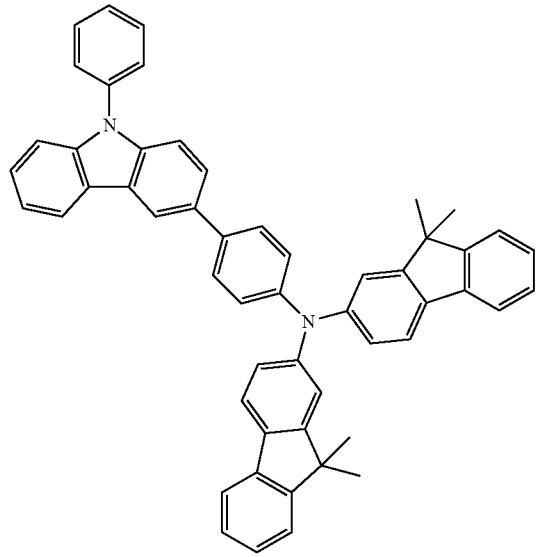
HT10
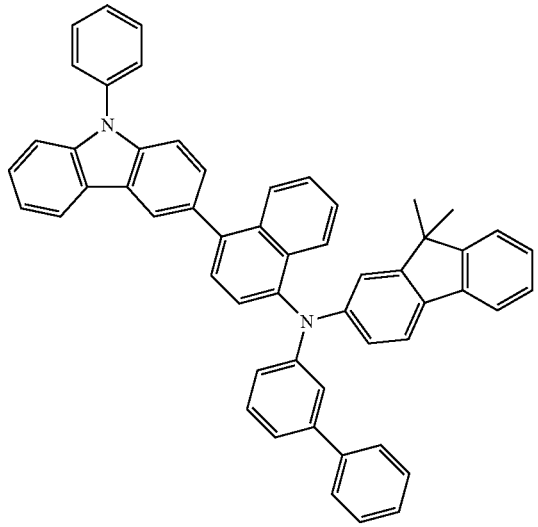
HT11
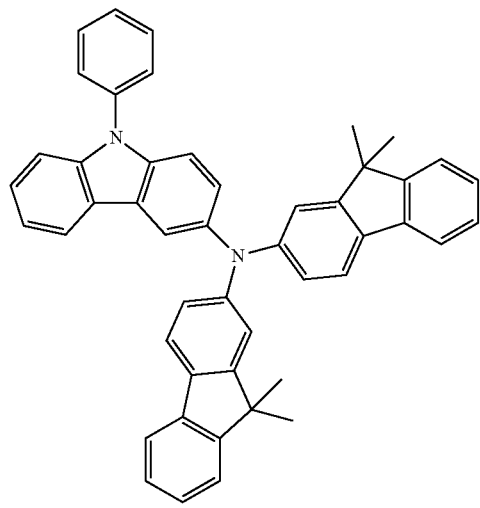
HT12
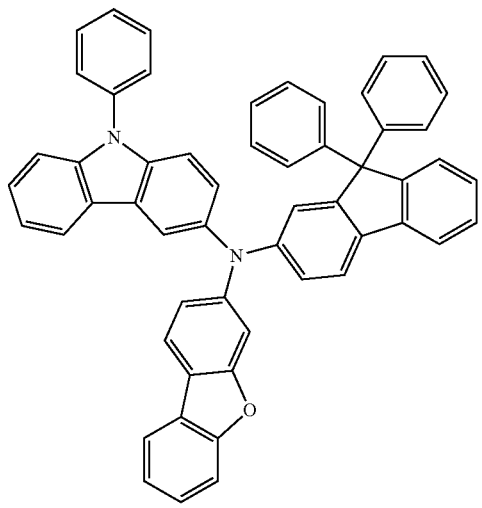
HT13
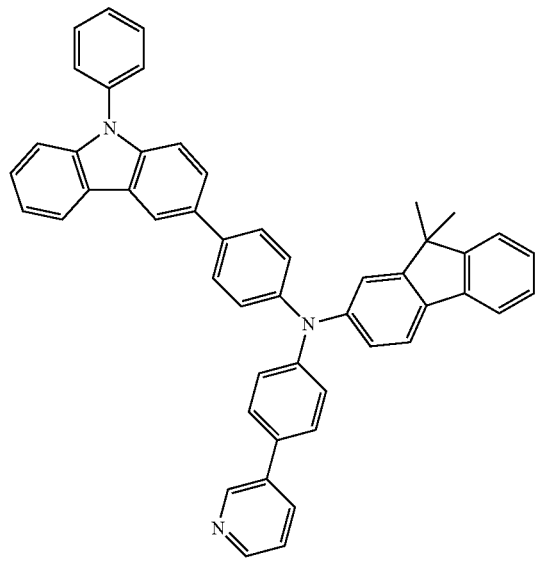
HT14
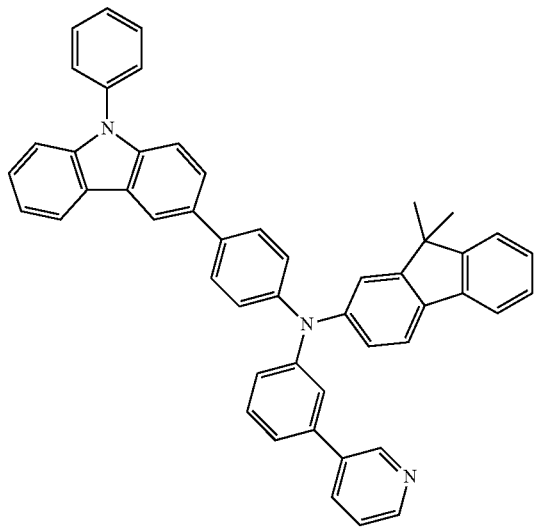

-continued
HT15
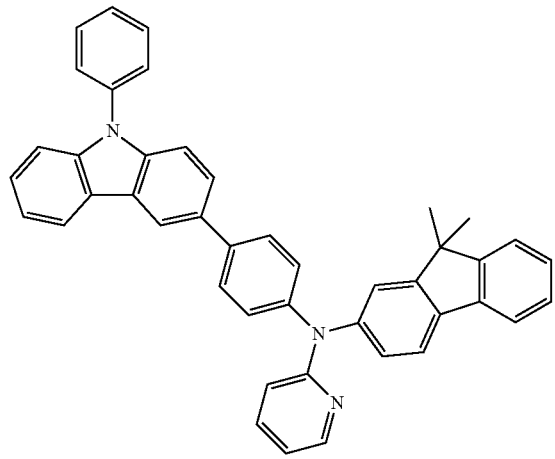
HT16
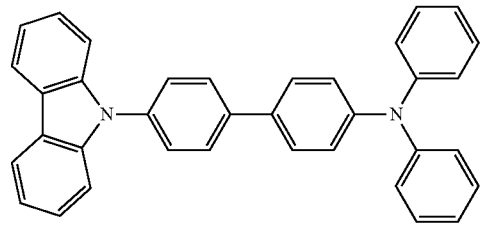
HT17
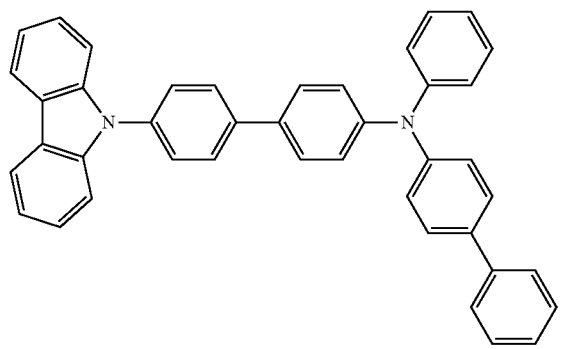
HT18
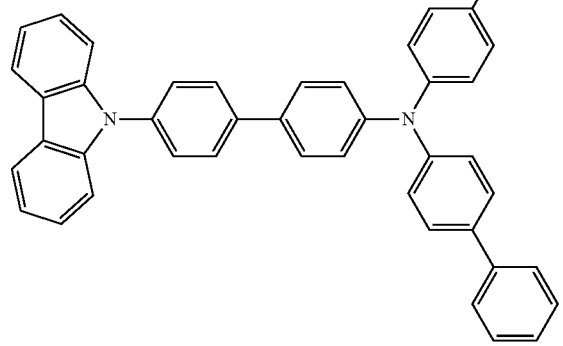
HT19
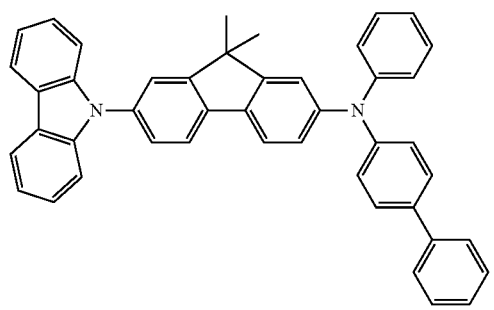
HT20
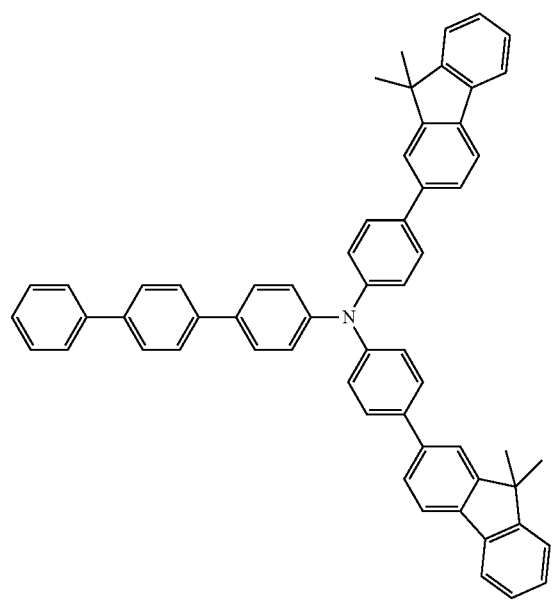

-continued
HT21
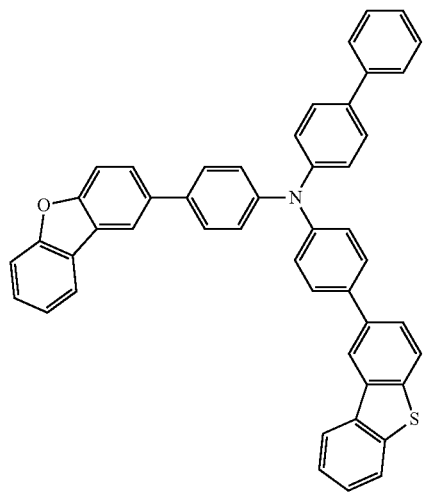
HT22
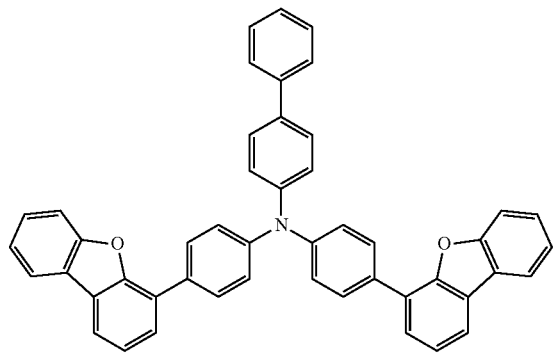
HT23
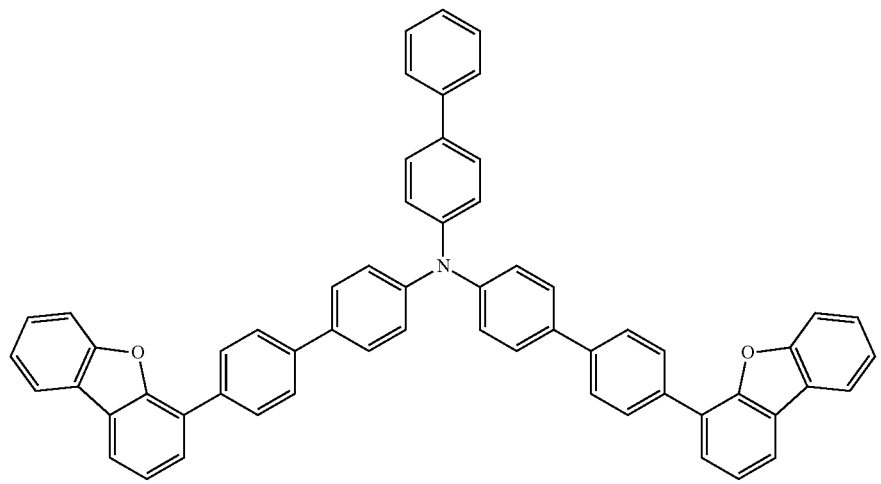
HT24
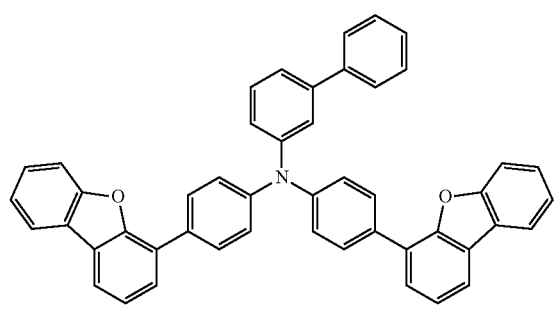
HT25
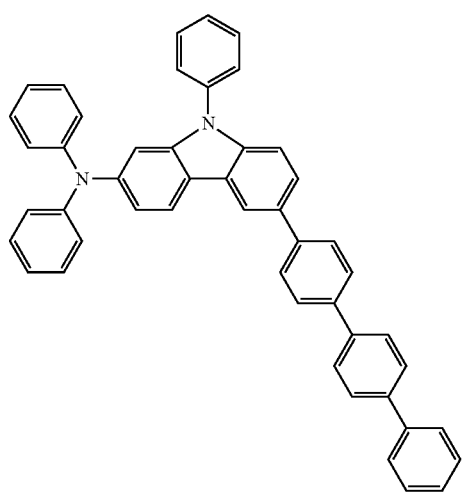

-continued
HT26
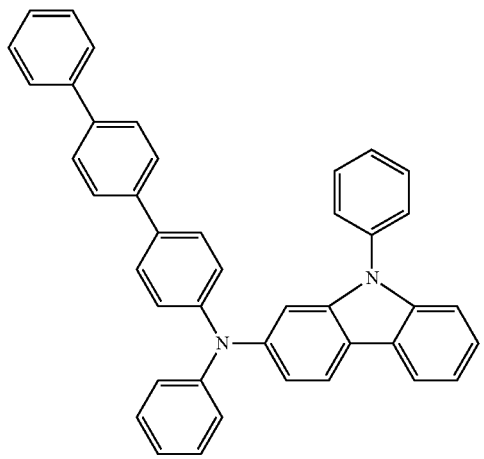
HT27
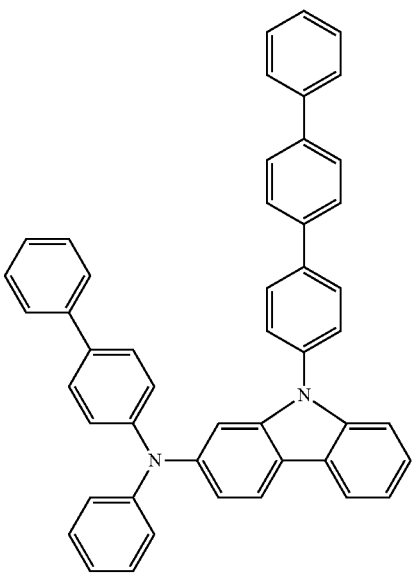
HT28
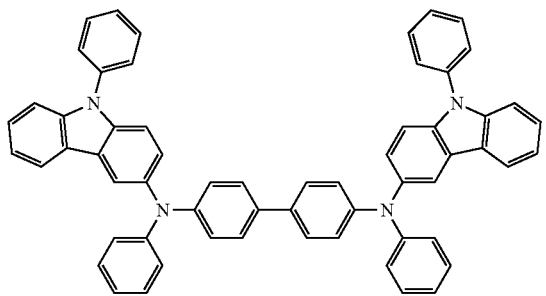
HT29
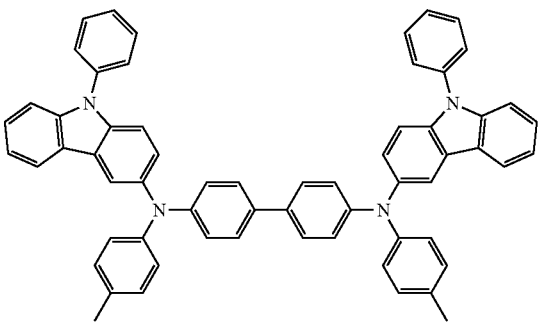
HT30
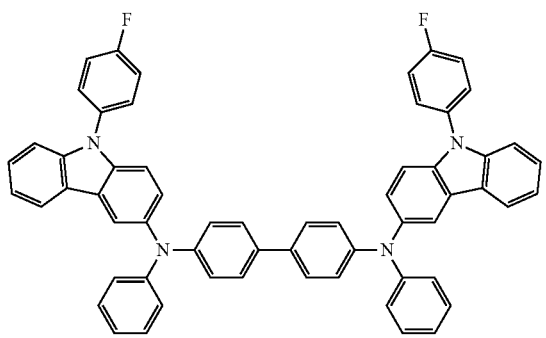
HT31
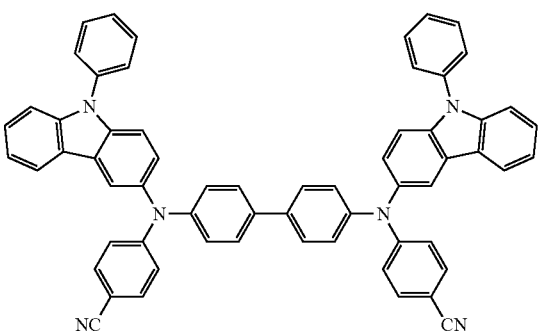

-continued
HT32
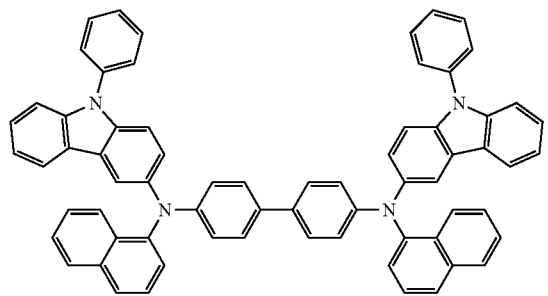
HT33
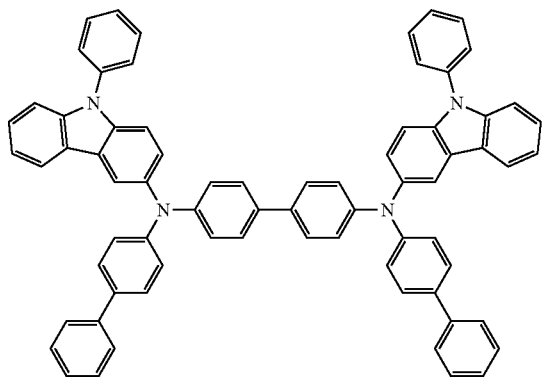
HT34
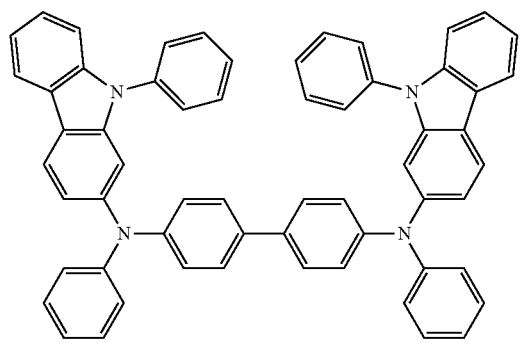
HT35
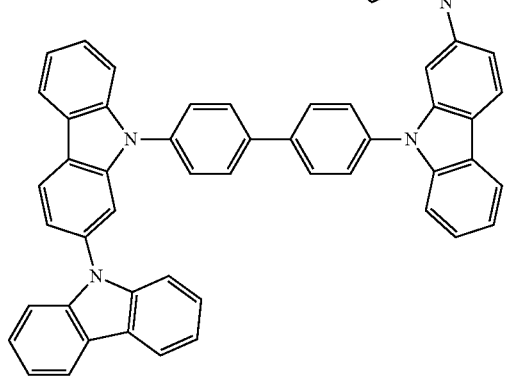
HT36
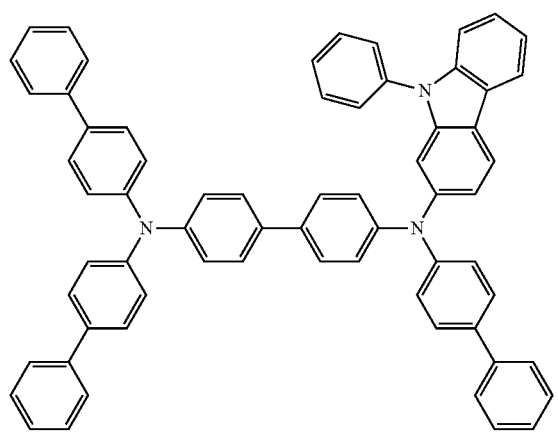
HT37
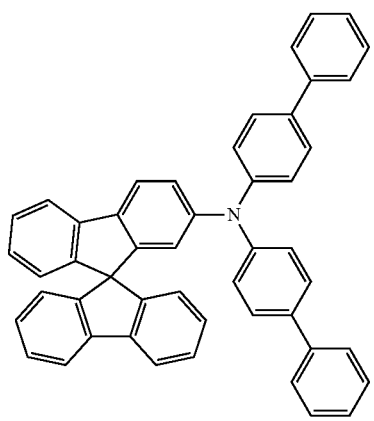

HT38

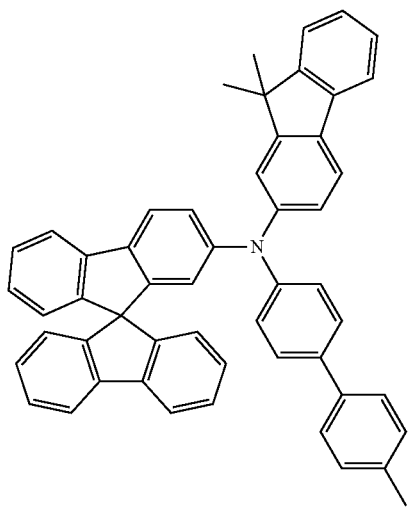

HT39

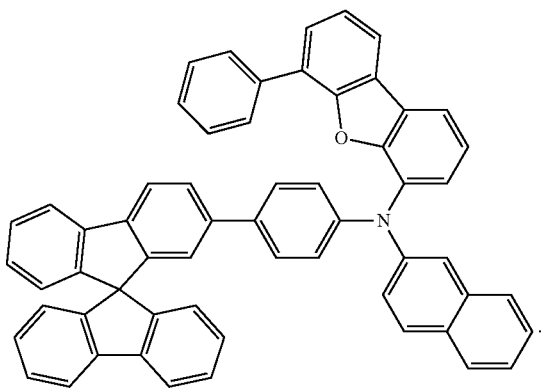

A thickness of the hole transport region may be from about 100 Å to about 10,000 Å, for example, about 100 Å to about 3,000 Å. When the hole transport region includes at least one selected from a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the hole transport region may further include a p-dopant having a LUMO energy level of about −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,12-hexaazatriphenylene-hexacarbonitrile (HAT-CN); and a compound represented by Formula 221, but embodiments of the present disclosure are not limited thereto:

<HAT-CN>

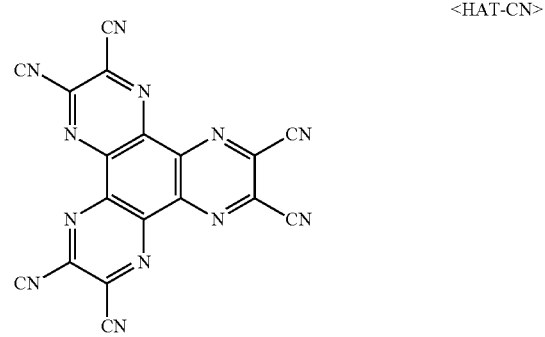

<F4-TCNQ>

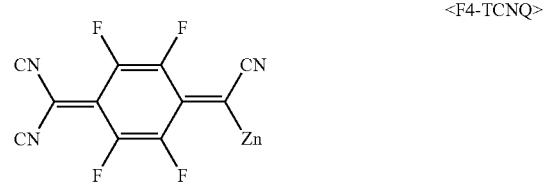

<Formula 221>

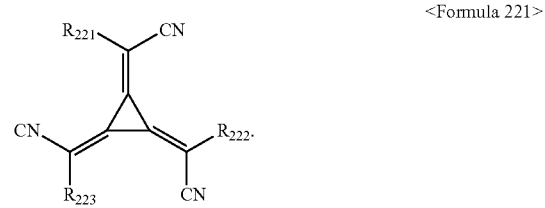

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may each independently have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

An amount of the dopant in the emission layer may be generally in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Host in Emission Layer

The host may include the heterocyclic compound.

In one or more embodiments, the host may further include a compound represented by Formula 301:

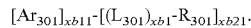

Formula 301

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more $Ar_{301}$(s) may be linked via a single bond.

In one or more embodiments, the compound represented by Formula 301 may be represented by Formula 301-1 or 301-2:

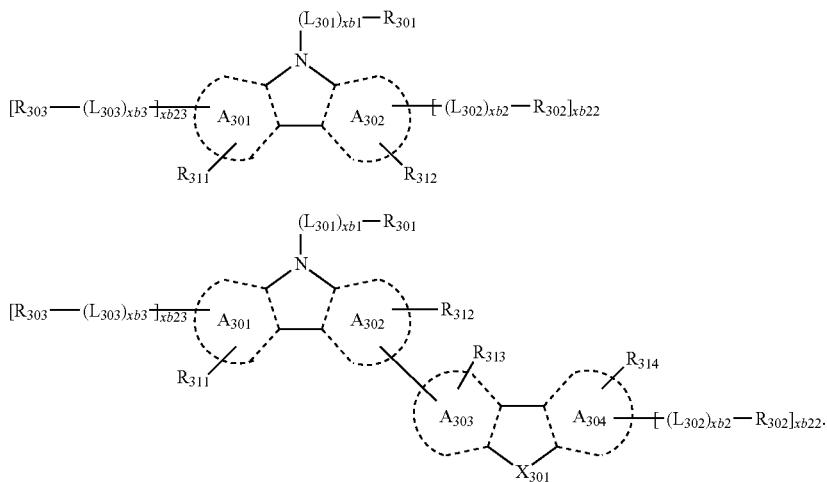

Formula 301-1

<Formula 301-2>

In Formulae 301-1 and 301-2, ring $A_{301}$ to ring $A_{304}$ may each independently be selected from a benzene ring, a naphthalene ring, a phenanthrene ring, a fluoranthene ring, a triphenylene ring, a pyrene ring, a chrysene ring, a pyridine ring, a pyrimidine ring, an indene ring, a fluorene ring, a spiro-bifluorene ring, a benzofluorene ring, a dibenzofluorene ring, an indole ring, a carbazole ring, a benzocarbazole ring, a dibenzocarbazole ring, a furan ring, a benzofuran ring, a dibenzofuran ring, a naphthofuran ring, a benzonaphthofuran ring, a dinaphthofuran ring, a thiophene ring, a benzothiophene ring, a dibenzothiophene ring, a naphthothiophene ring, a benzonaphthothiophene ring, and a dinaphthothiophene ring, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, xb22 and xb23 may each independently be 0, 1, or 2, $L_{301}$, xb1, $R_{301}$, and $Q_{31}$ to $Q_{33}$ are the same as described above, $L_{302}$ to $L_{304}$ may each independently be the same as defined in connection with $L_{301}$, xb2 to xb4 may each independently be the same as defined in connection with xb1, and $R_{302}$ to $R_{304}$ may each independently be the same as defined in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:
H1
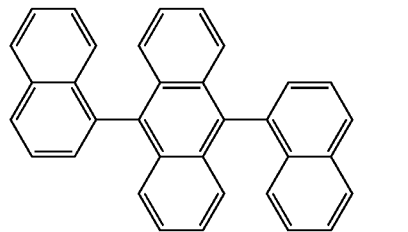
H2
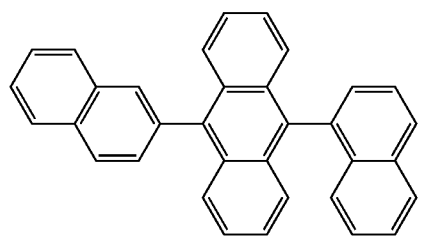
H3
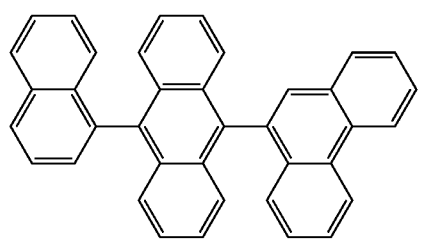
H4
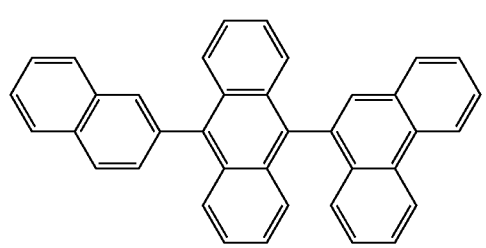
H5
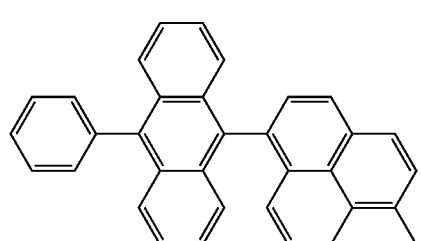
H6
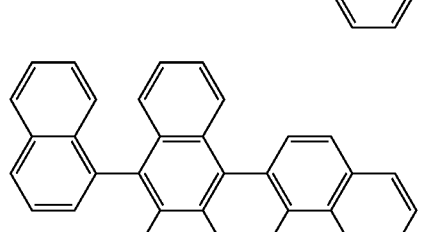
H7
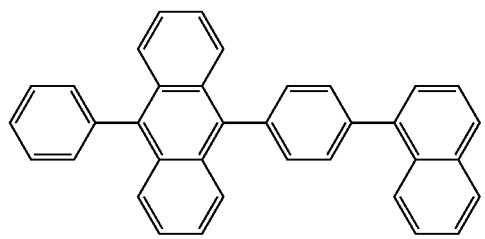
H8
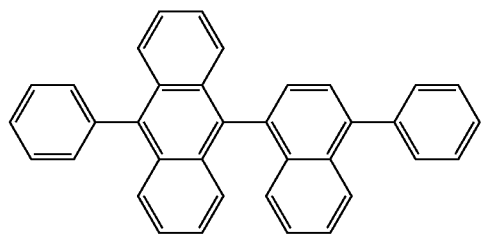
H9
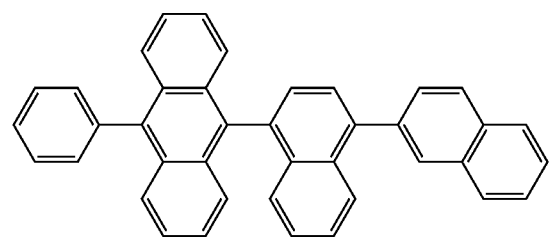
H10
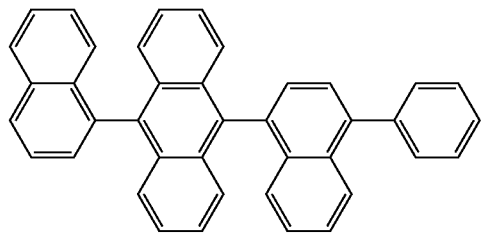
H11
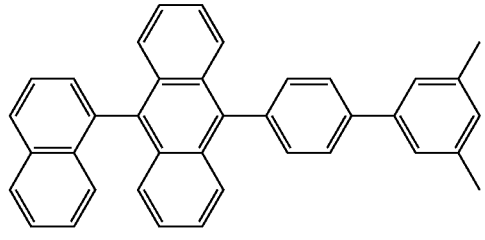
H12
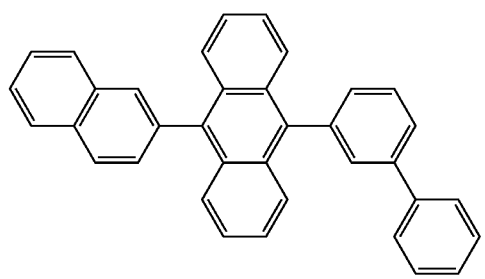

H13
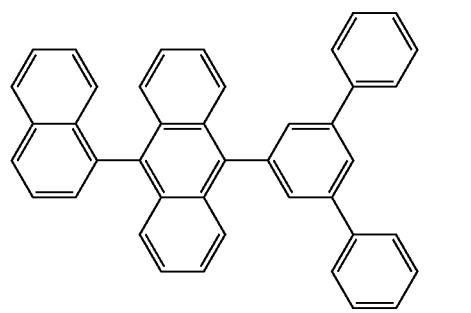
H14
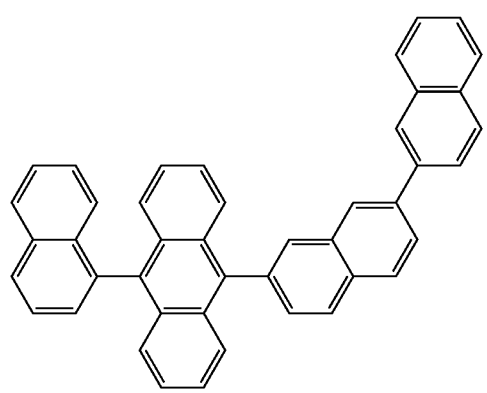
H15
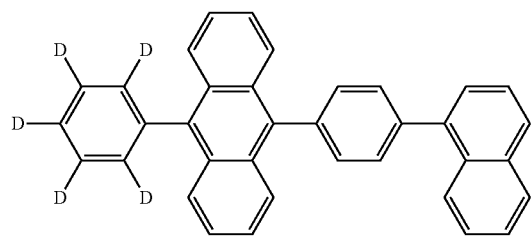
H16
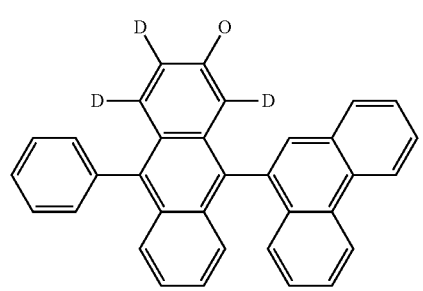
H17
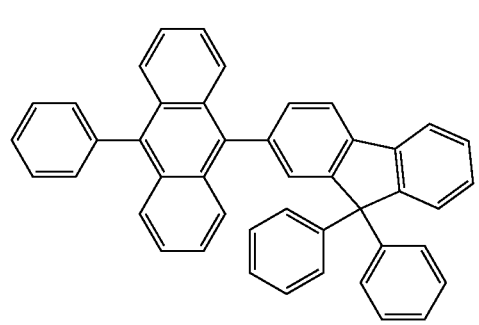
H18
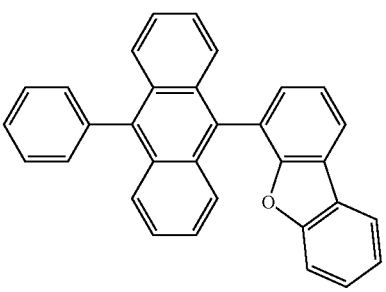
H19
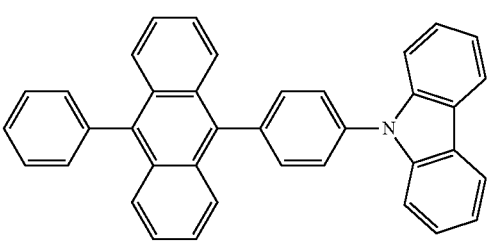
H20
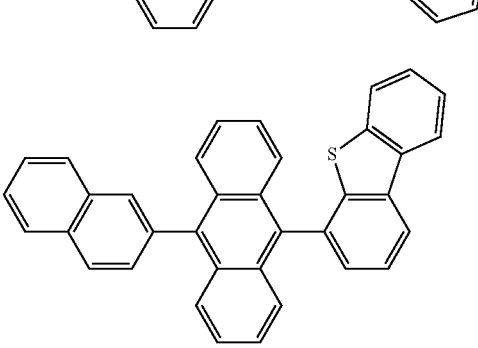
H21
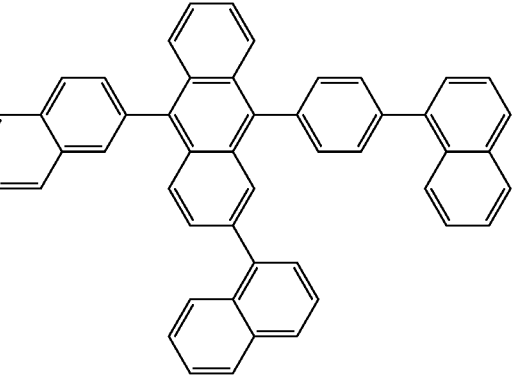
H22
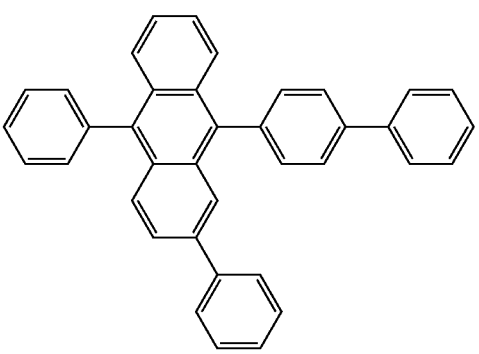

H23
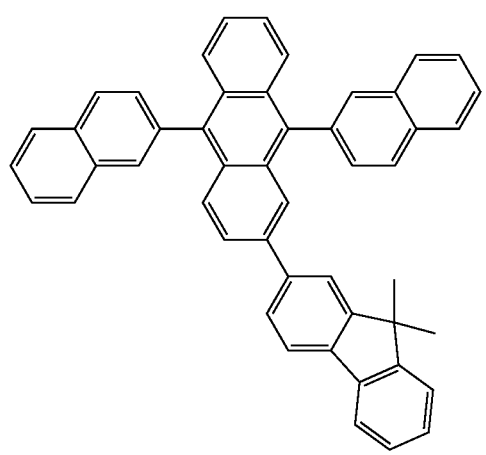
H24
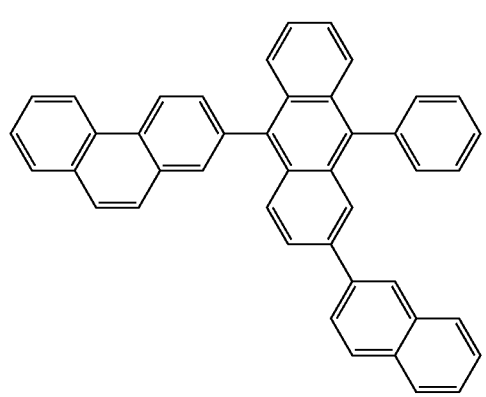
H25
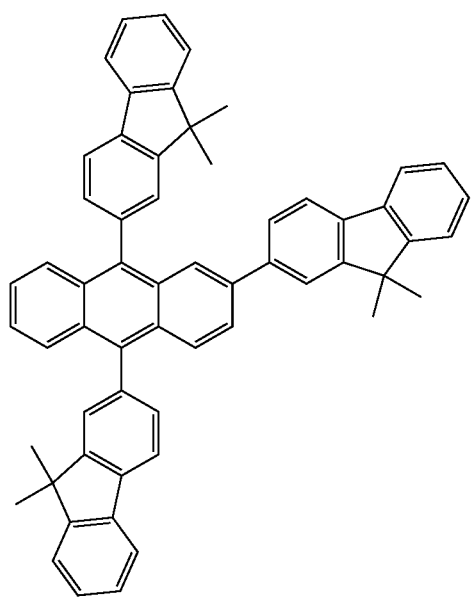
H26
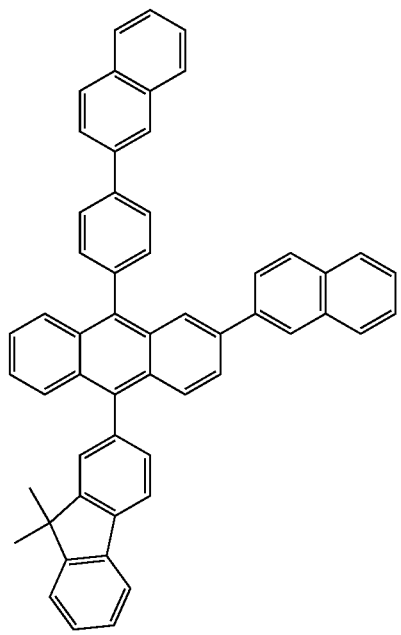
H27
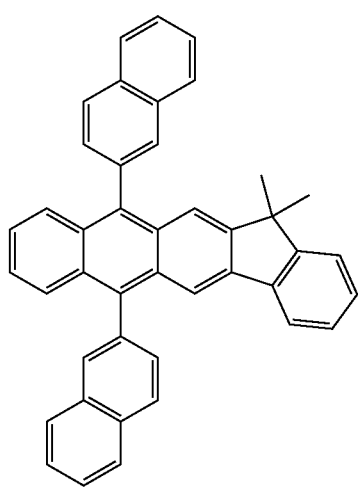
H28
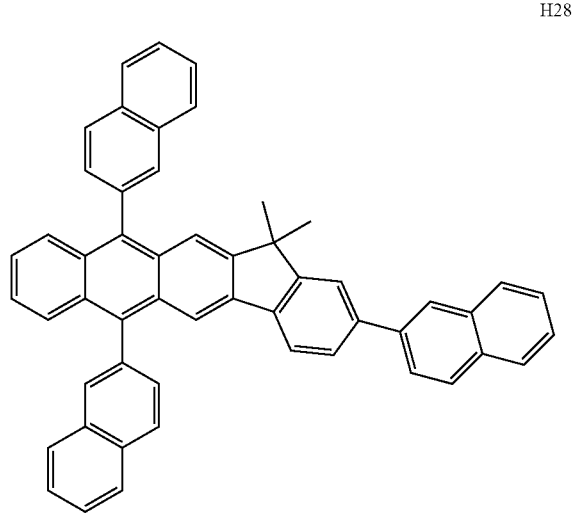

H29
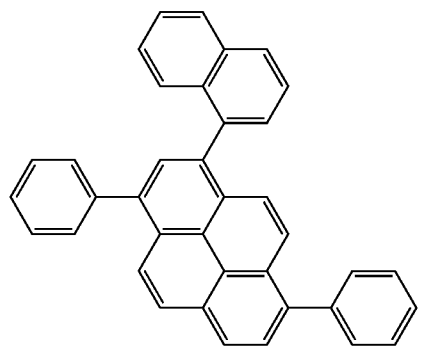
H30
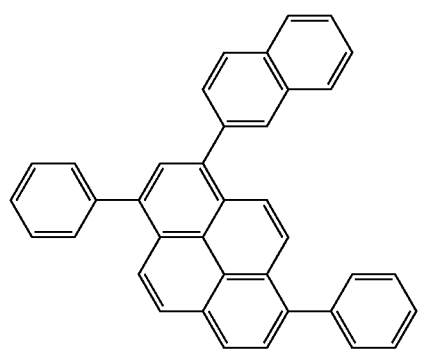
H31
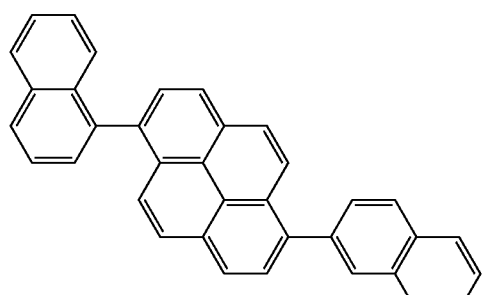
H32
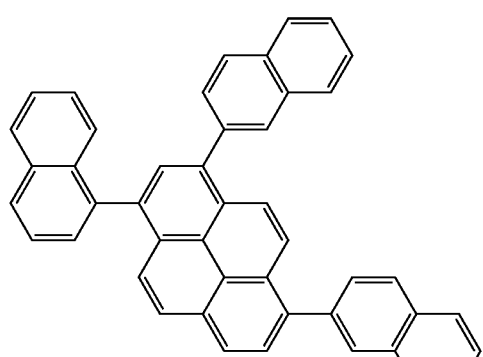
H33
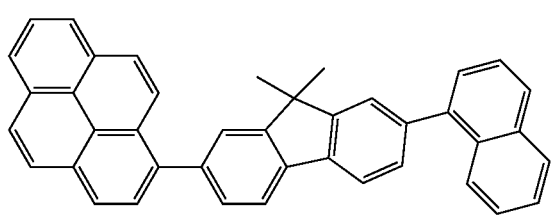
H34
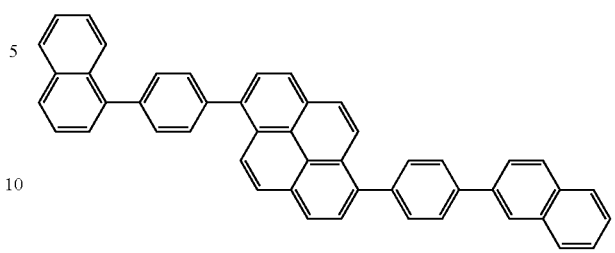
H35
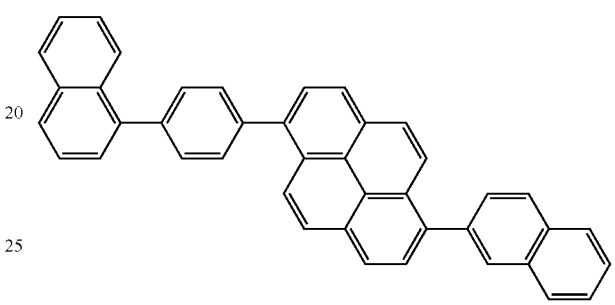
H36
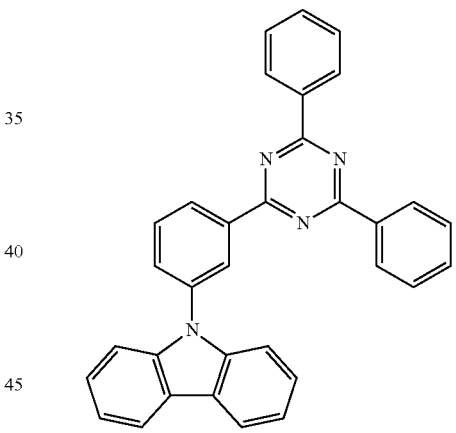
H37
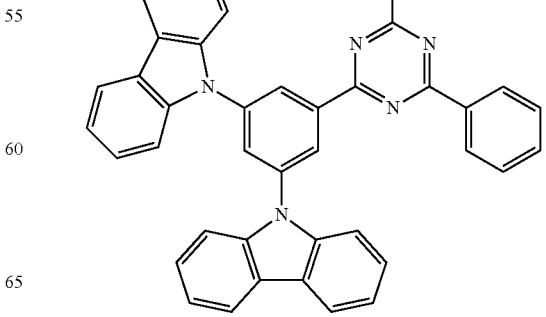

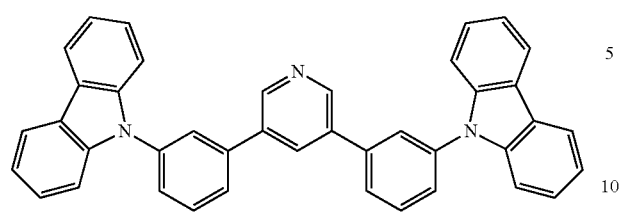
H38
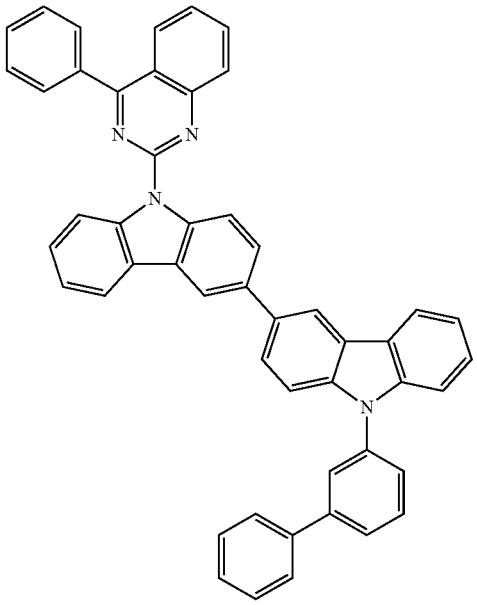
H41
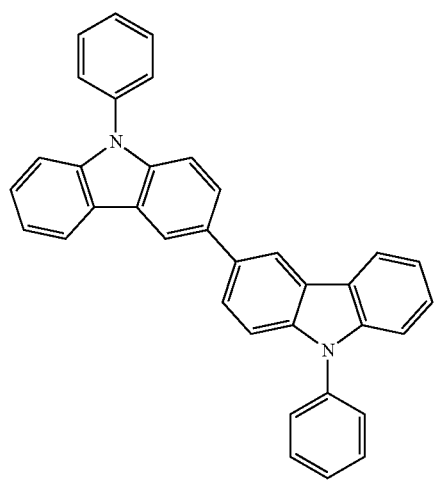
H39
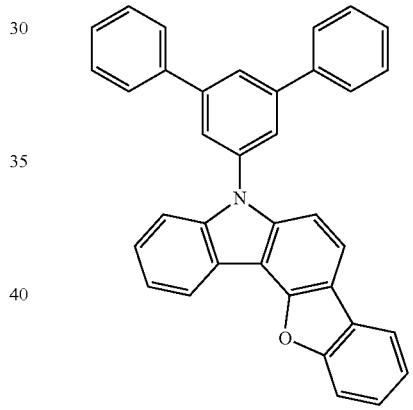
H42
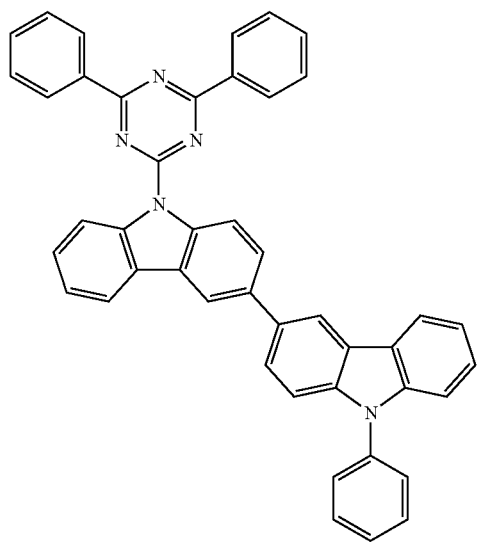
H40
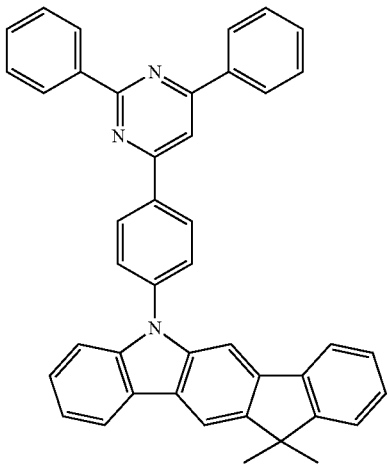
H43

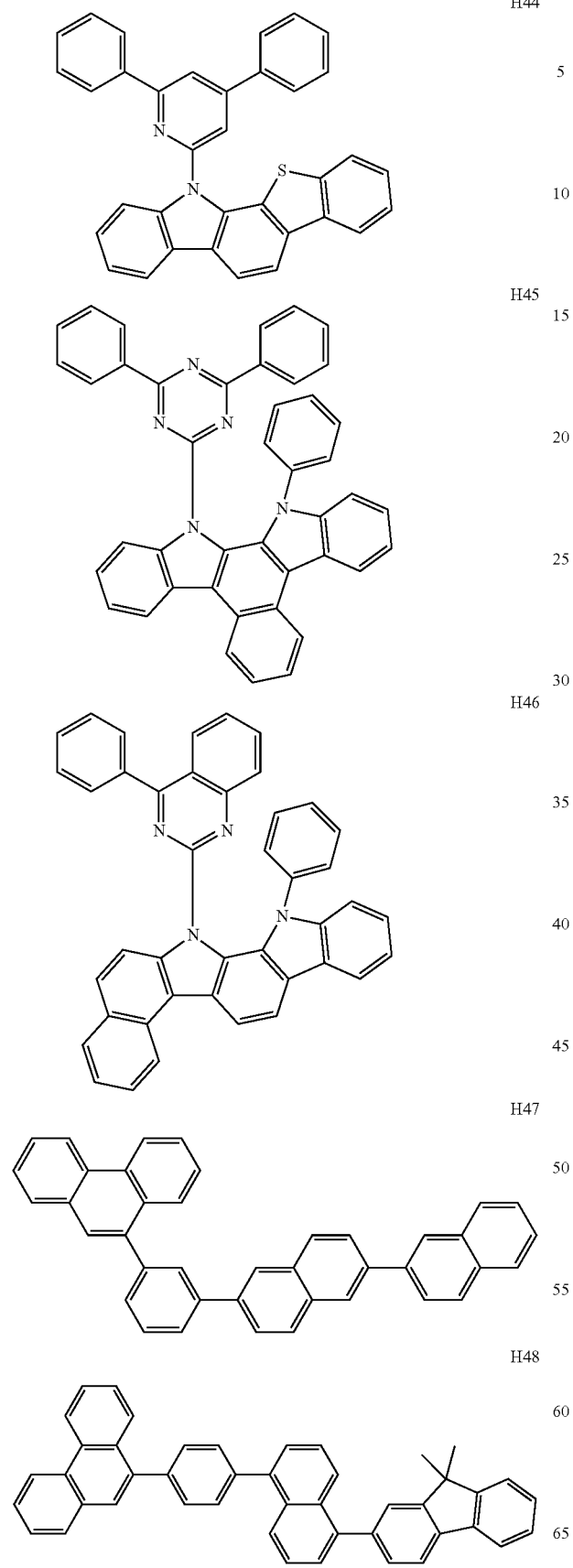
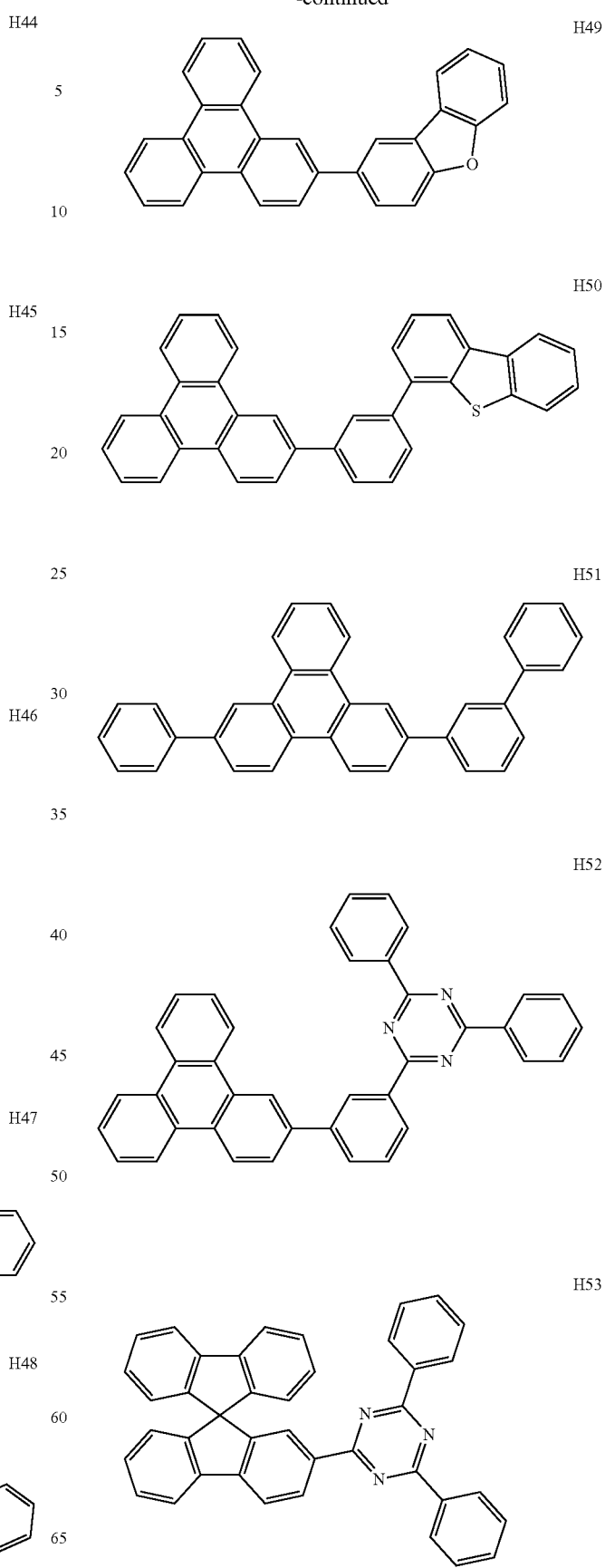

-continued

H54

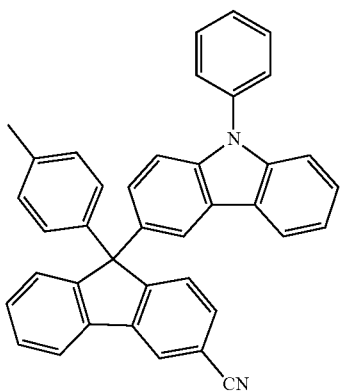

H55

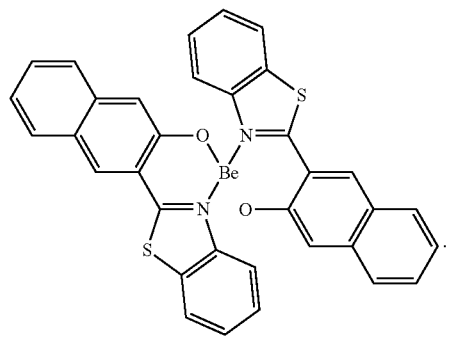

Phosphorescent dopant included in emission layer in organic layer 150

The phosphorescent dopant may include an organometallic complex represented by Formula 401:

$$M(L_{401})_{xc1}(L_{402})_{xc2}$$ Formula 401

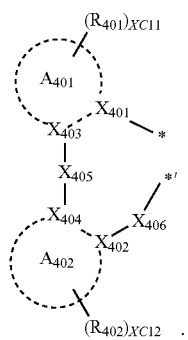

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*$^1$, or *=C($Q_{411}$)=*',
wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *$^1$ in Formula 402 each indicate a binding site to M in Formula 401.

In one embodiment, ring $A_{401}$ and ring $A_{402}$ in Formula 402 may each independently be selected from a benzene group, a naphthalene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantly group, a norbornanyl group, and a norbornenyl group;

a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantly group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O) ($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is two or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see Compounds PD1 to PD4 and PD7). $X_{407}$ and $X_{408}$ may each independently be selected from a single bond, *—O—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and a phosphorus-containing material (for example, phosphine or phosphite), but embodiments of the present disclosure are not limited thereto.

In one or more embodiments, the phosphorescent dopant may be selected from, for example, Compounds PD1 to PD25, but embodiments of the present disclosure are not limited thereto:

PD1

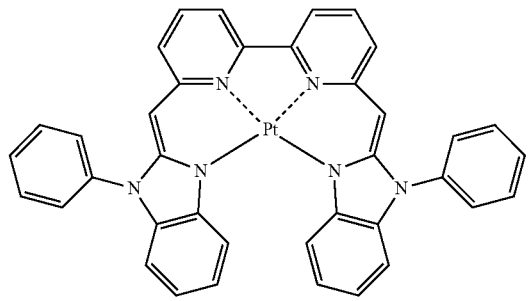

PD2

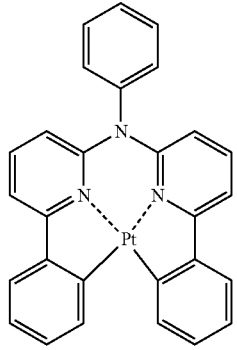

PD3

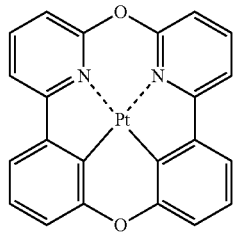

PD4

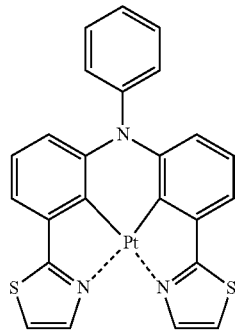

PD5

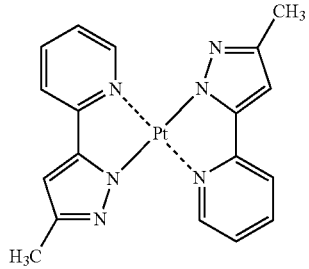

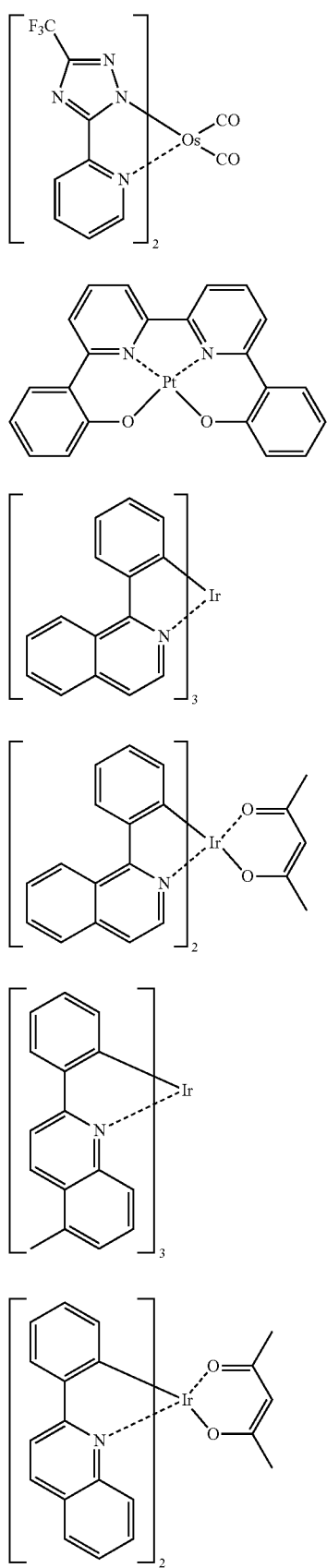

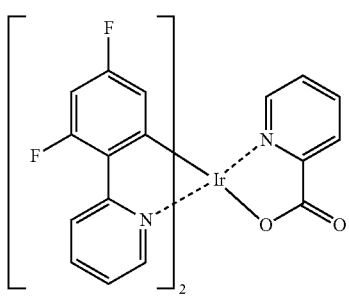
PD17
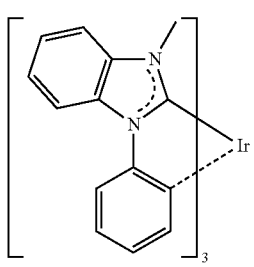
PD18
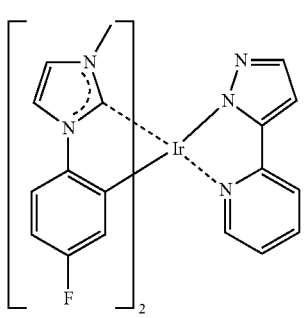
PD19
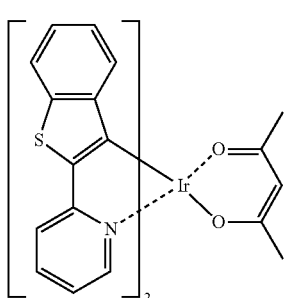
PD20
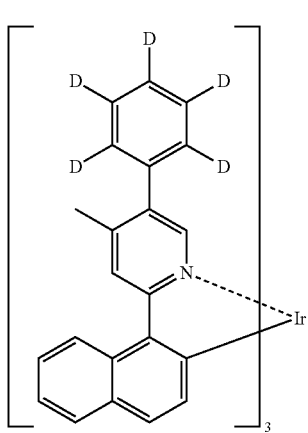
PD21
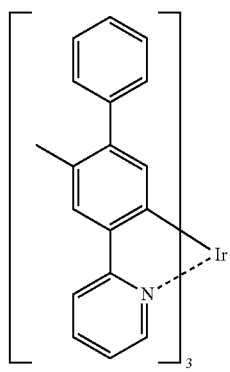
PD22
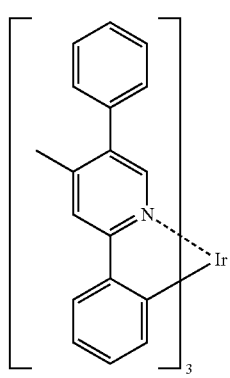
PD23
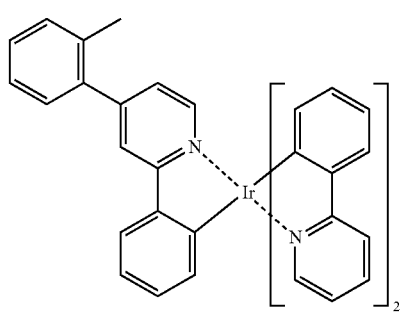
PD24
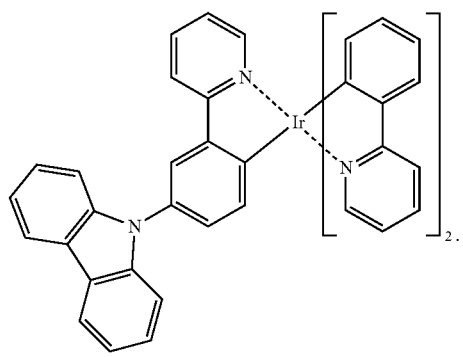
PD25
Fluorescent Dopant in Emission Layer
The fluorescent dopant may include an arylamine compound or a styrylamine compound.

The fluorescent dopant may include a compound represented by Formula 501:

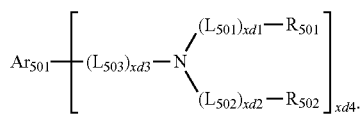

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, xd4 may be an integer from 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

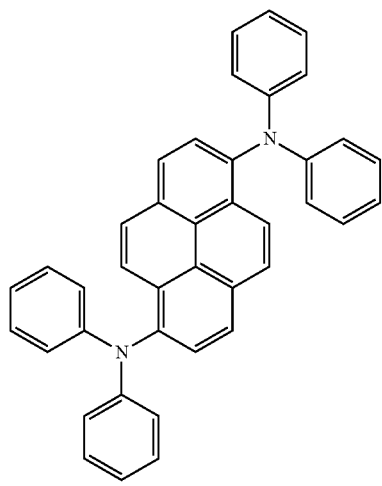

FD1

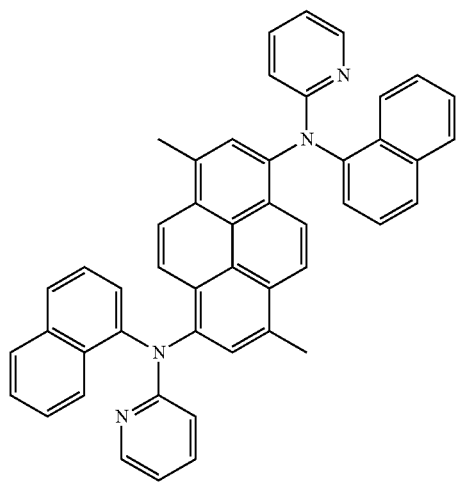

FD2

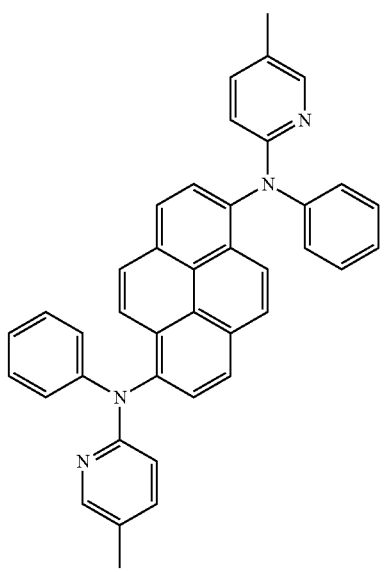

FD3

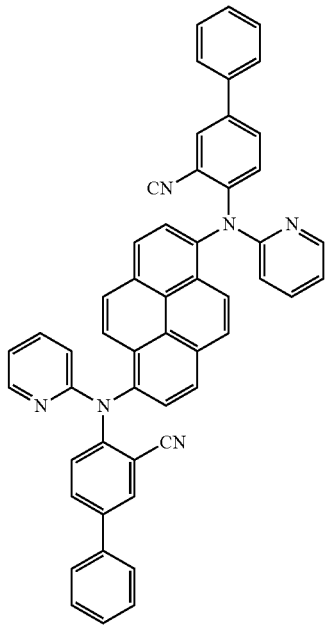

FD4

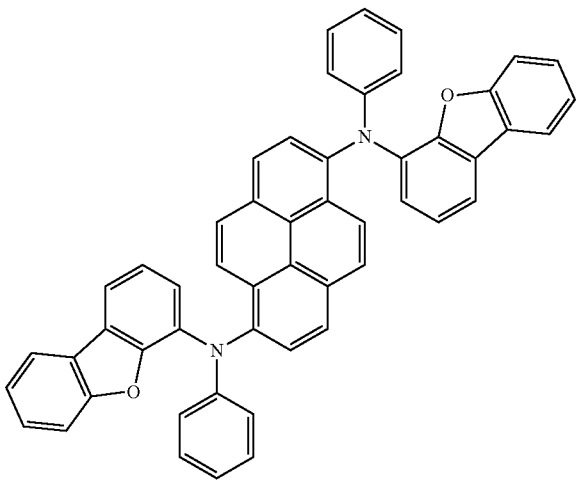

FD5

FD6
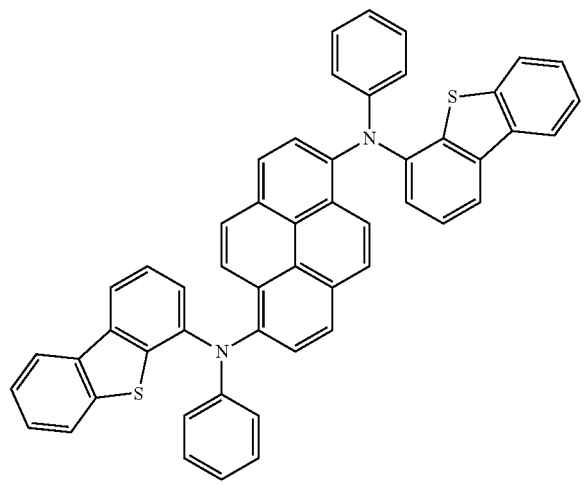
FD9
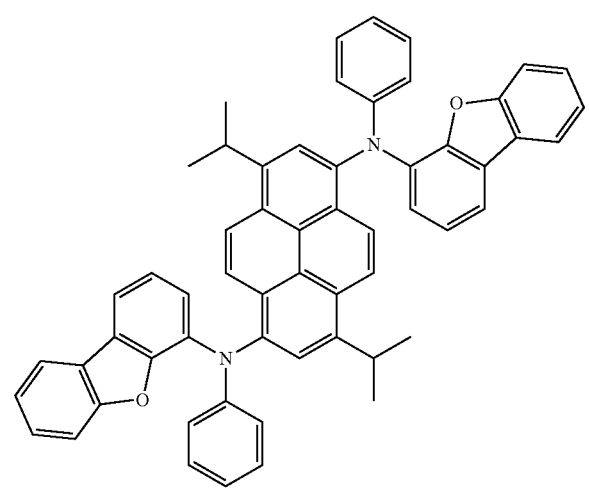
FD7
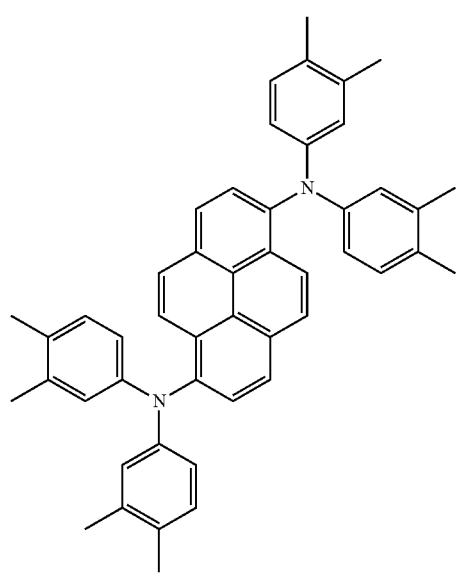
FD10
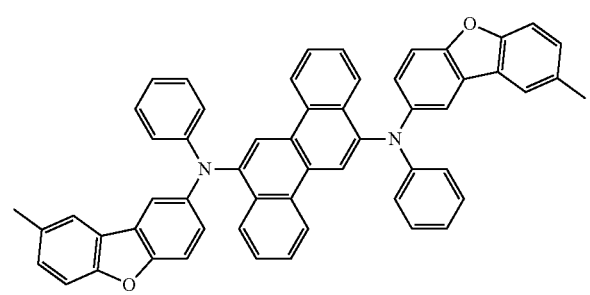
FD11
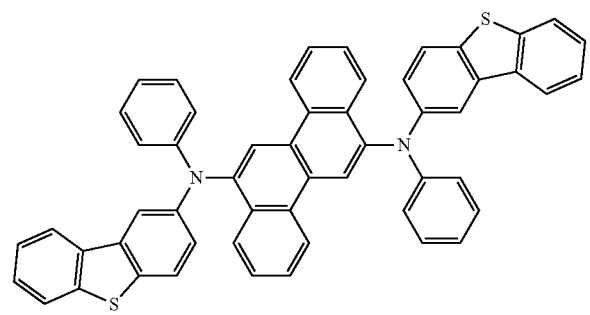
FD8
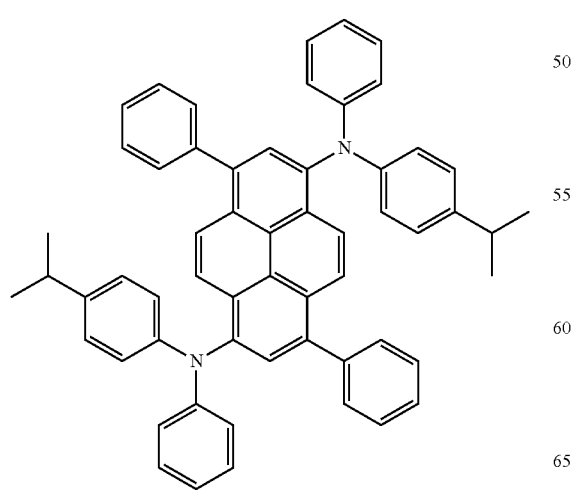
FD12
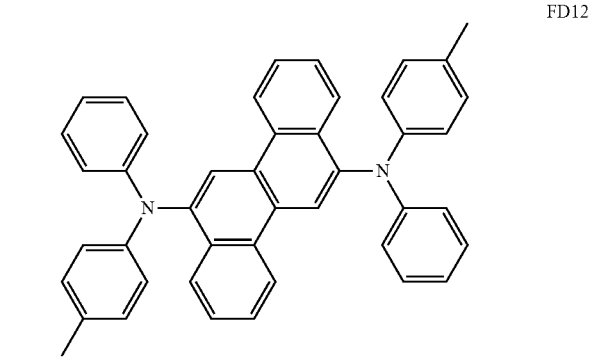

-continued
FD13
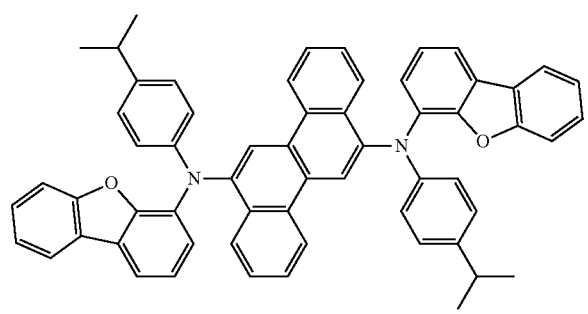
FD14
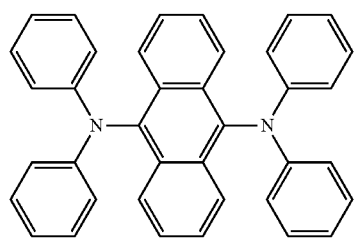
FD15
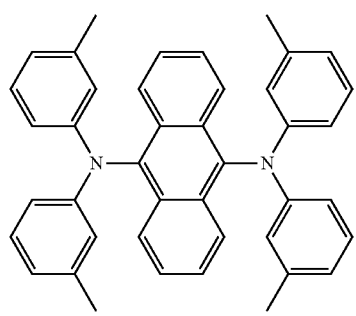
FD16
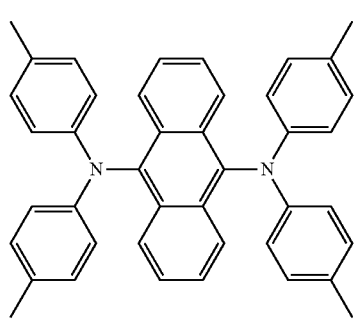
-continued
FD17
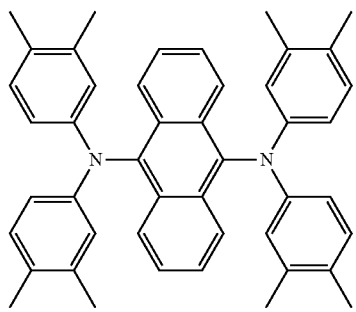
FD18
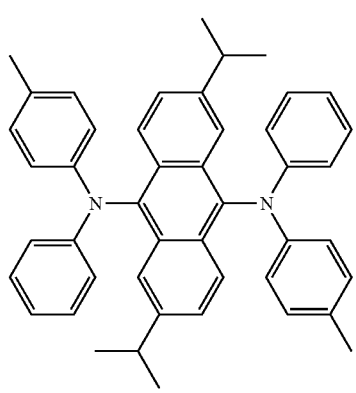
FD19
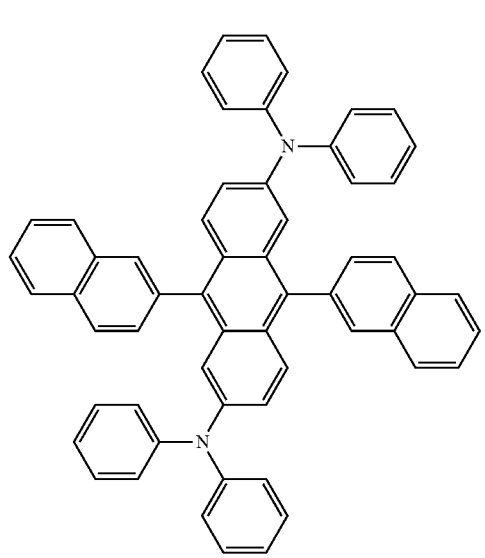
FD20
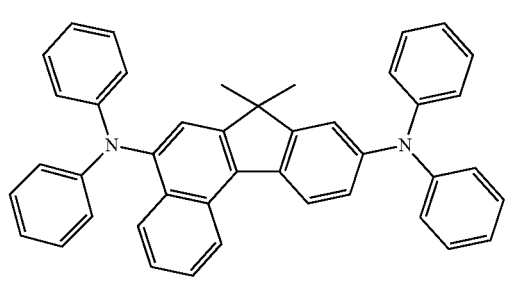

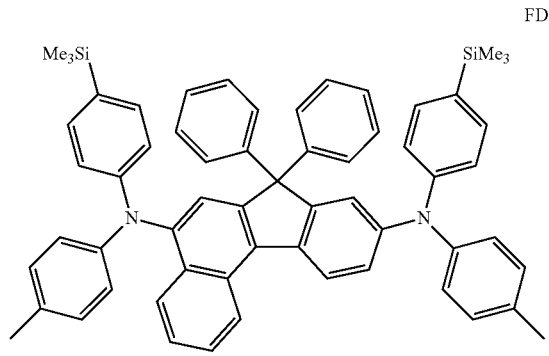
FD21
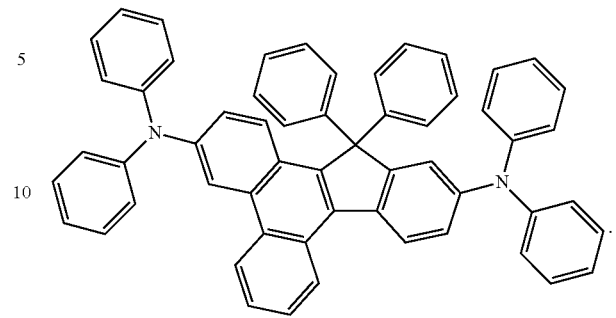
FD22
In one or more embodiments, the fluorescent dopant may be selected from the following compounds, but embodiments of the present disclosure are not limited thereto:
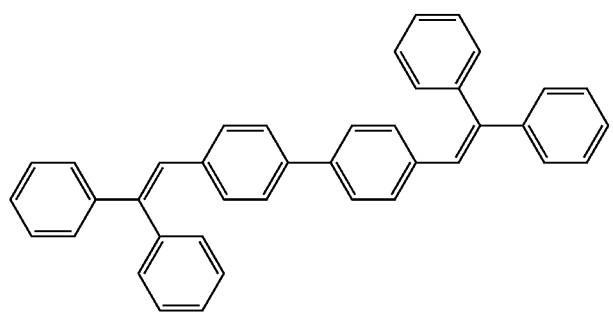
DPVBi
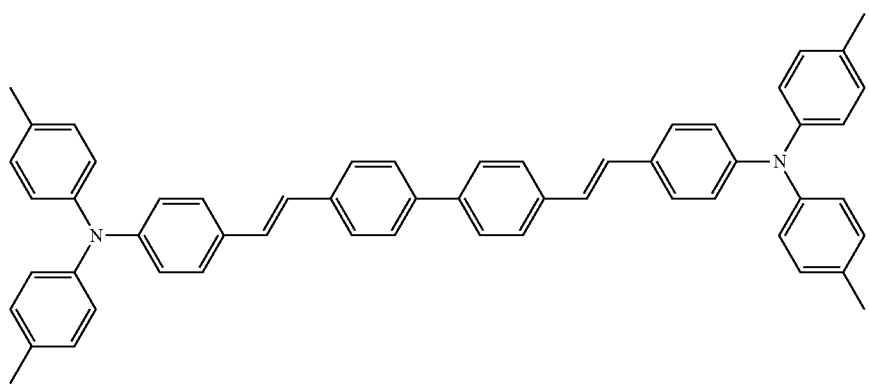
DPAVBi
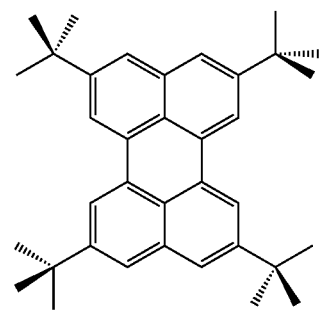
TBPe
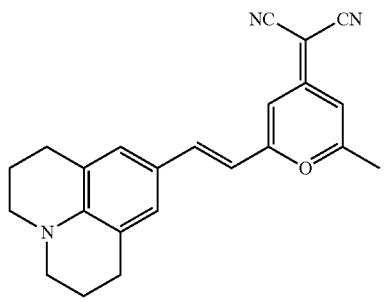
DCM

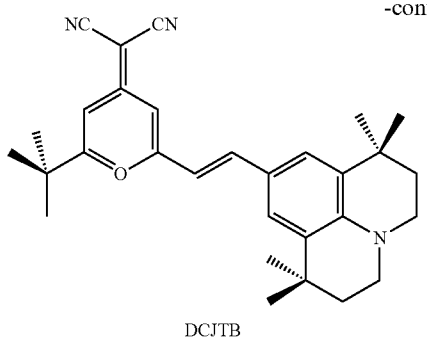
DCJTB

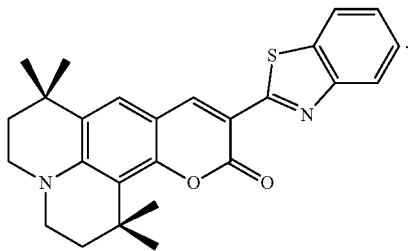
C545T

Coumarin 6

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one 7 electron-depleted nitrogen-containing ring.

As used herein, the term "7 electron-depleted nitrogen-containing ring" indicates a $C_1$-$C_{60}$ heterocyclic group having at least one *—N=*' moiety as a ring-forming moiety.

For example, the "7 electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other (e.g., combined together), or iii) a heteropolycyclic group in which at least one of 5-membered to 7-membered heteromonocyclic groups, each having at least one *—N=*' moiety, is condensed with (e.g., combined with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazole, an imidazopyridine, an imidazopyrimidine, and an azacarbazole, but are not limited thereto.

For example, the electron transport region may include a compound represented by Formula 601:

$$[Ar_{601}]_{xe11}\text{-}[(L_{601})_{xe1}\text{-}R_{601}]_{x21}. \quad \text{Formula 601}$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), and $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and $R_{601}$ (S) in the number of xe21 may include the π electron-depleted nitrogen-containing ring.

In one embodiment, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1:

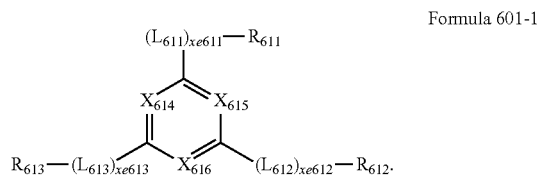

Formula 601-1

In Formula 601-1, $X_{614}$ may be N or C($R_{614}$), $X_{615}$ may be N or C($R_{615}$), and $X_{616}$ may be N or C($R_{616}$), wherein at least one selected from $X_{614}$ to $X_{616}$ may each independently be N, $L_{611}$ to $L_{613}$ may each independently be the same as described in connection with $L_{601}$, xe611 to xe613 may each independently be defined the same as xe1, $R_{611}$ to $R_{613}$ may each independently be the same as defined in connection with $R_{601}$, $R_{614}$ to $R_{616}$ may each independently be selected from hydrogen, deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ are the same as described above.

The electron transport region may include at least one compound selected from Compounds ET1 to ET36, but embodiments of the present disclosure are not limited thereto:

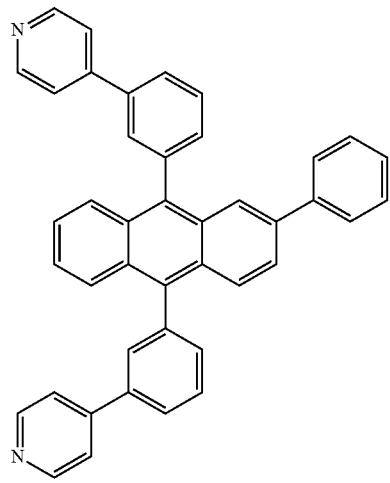

ET3

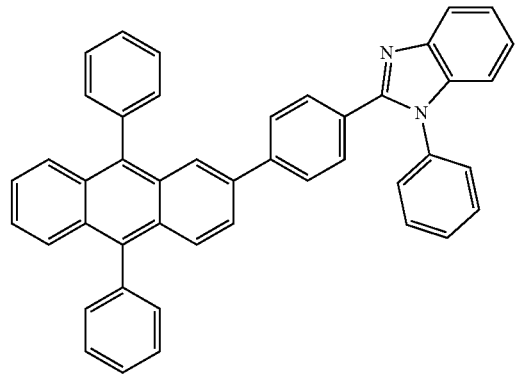

ET1

ET4

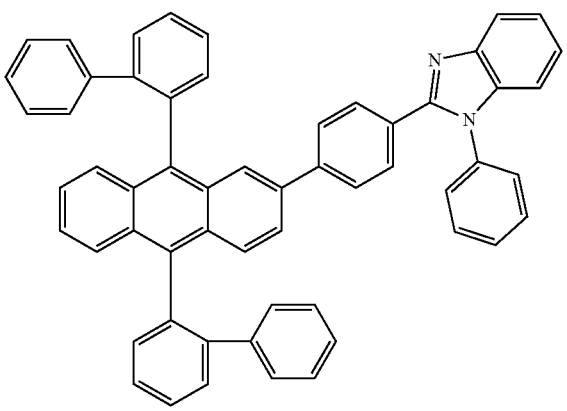

ET2

ET5

ET6
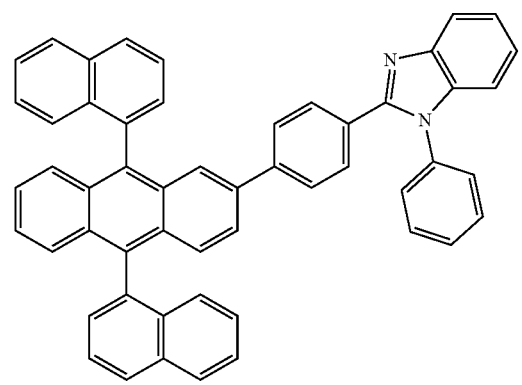
ET7
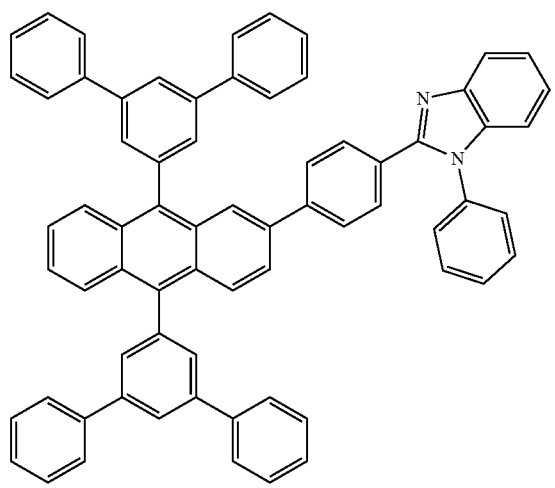
ET8
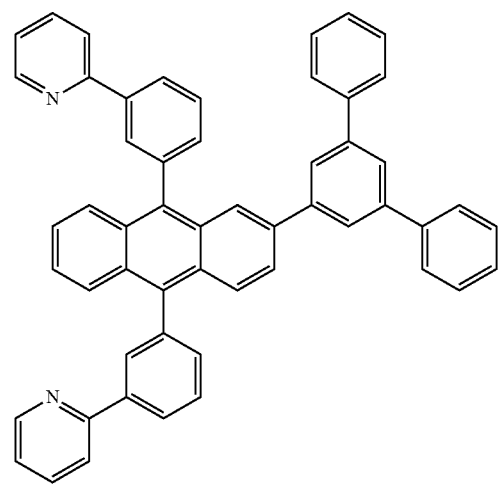
ET9
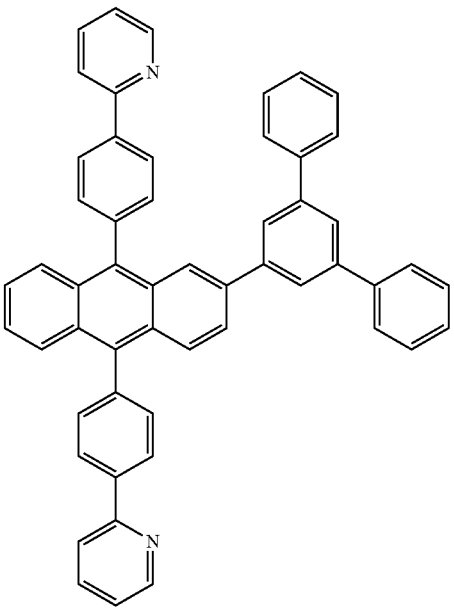
ET10
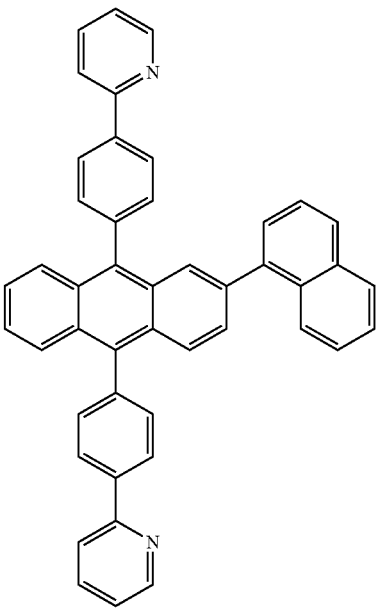

ET11
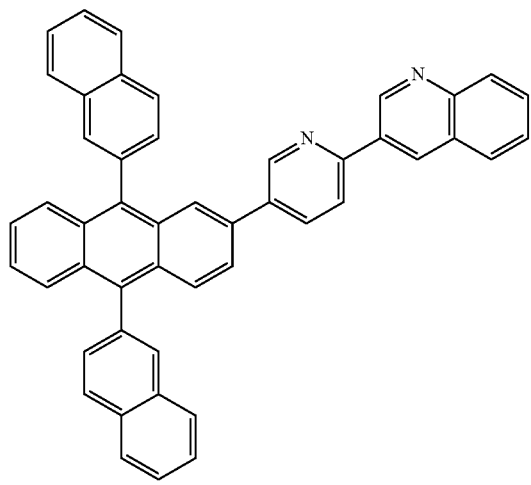
ET14
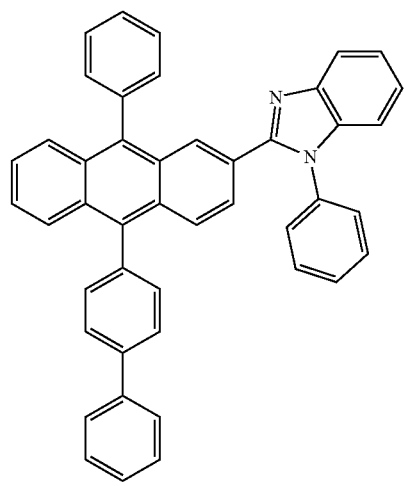
ET12
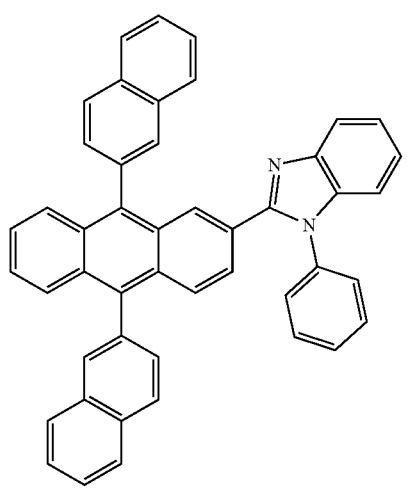
ET15
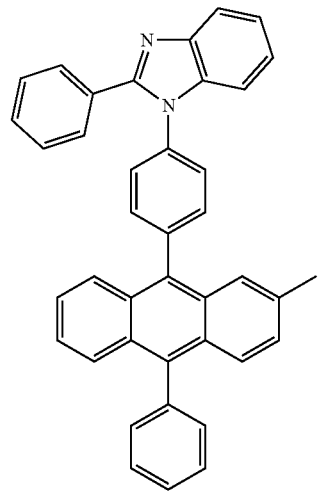
ET13
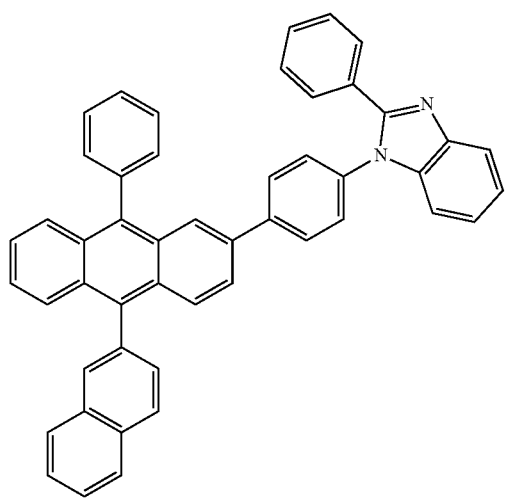
ET16
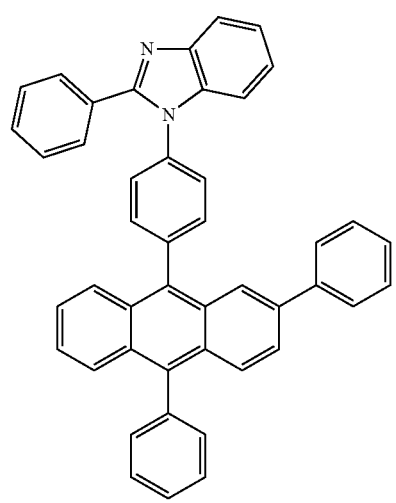

ET17
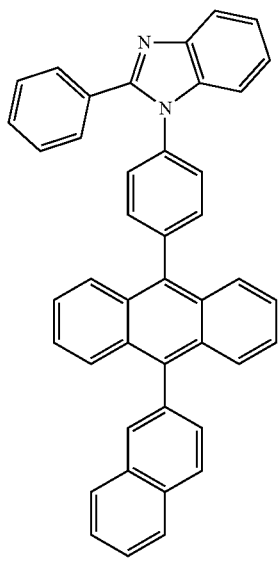
ET18
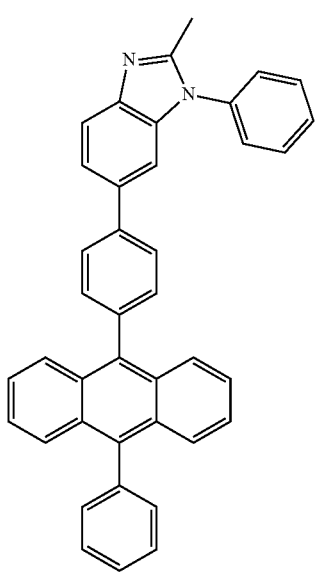
ET19
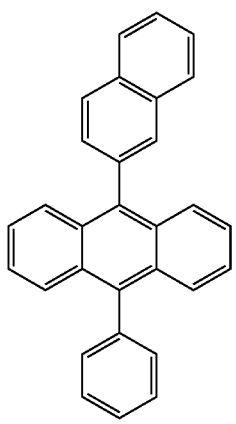
ET20
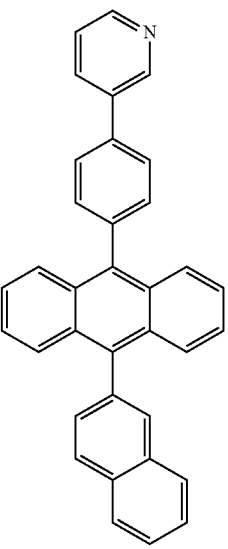
ET21
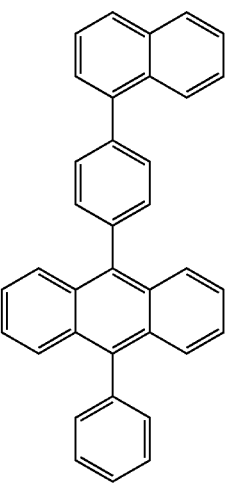
ET22
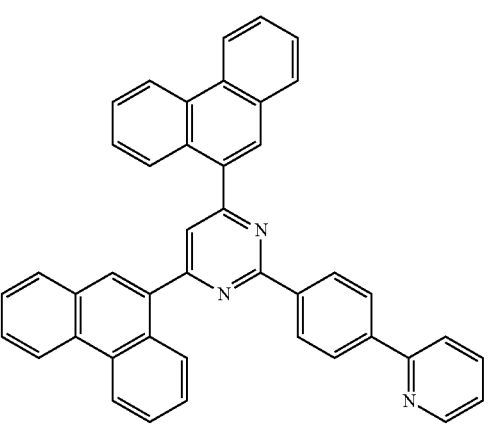

ET23
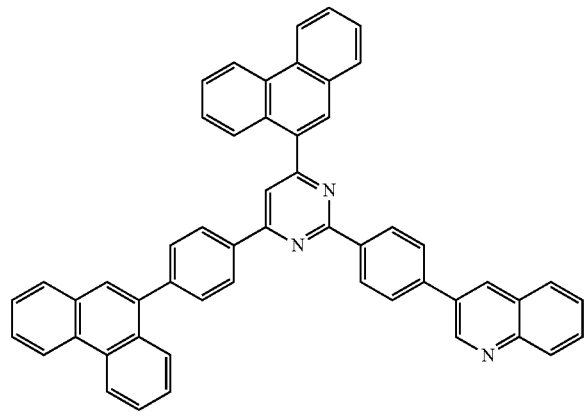
ET24
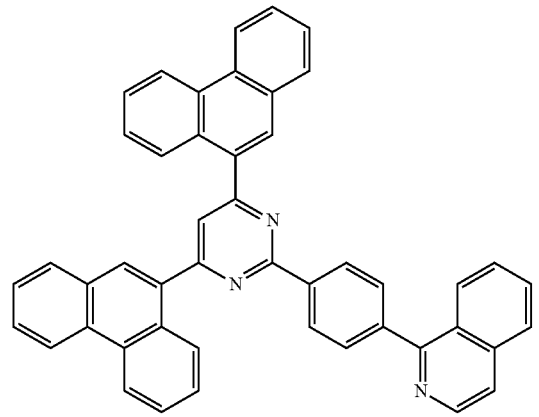
ET25
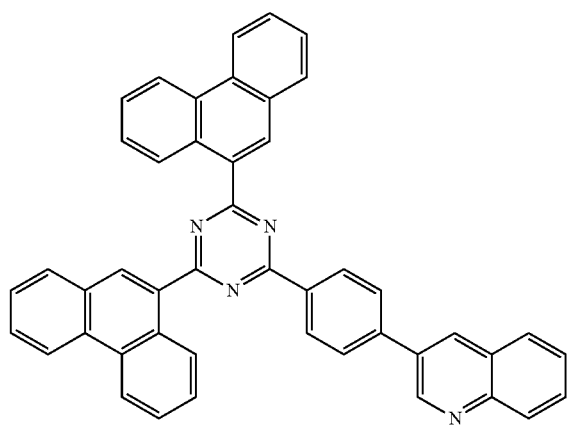
ET26
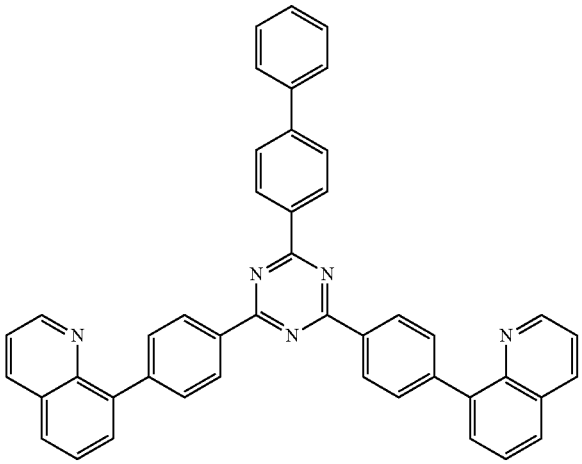
ET27
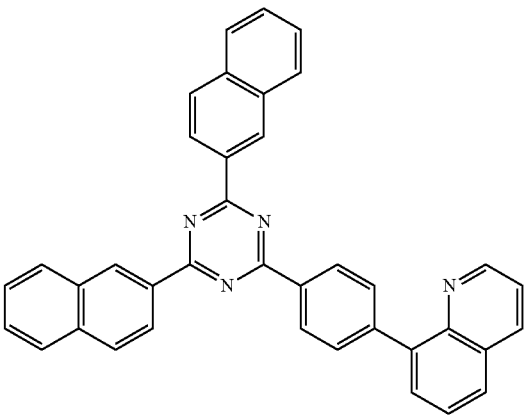
ET28
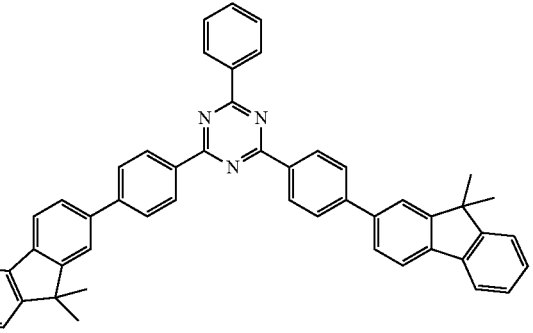

ET29
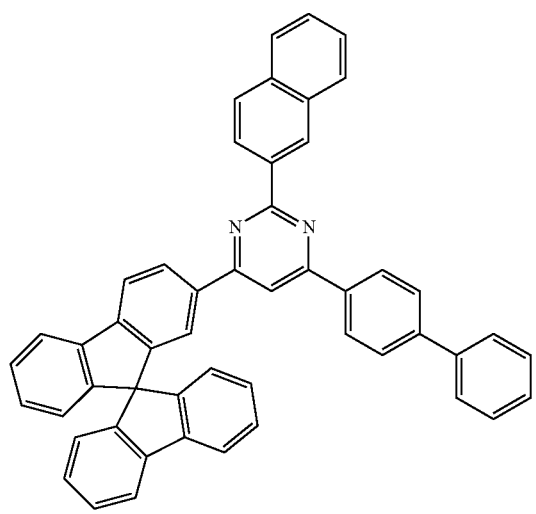
ET32
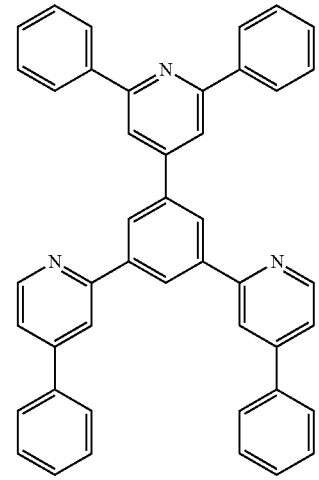
ET30
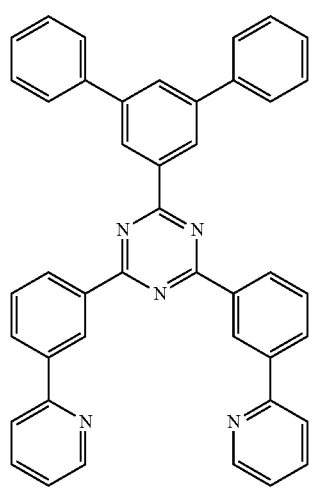
ET33
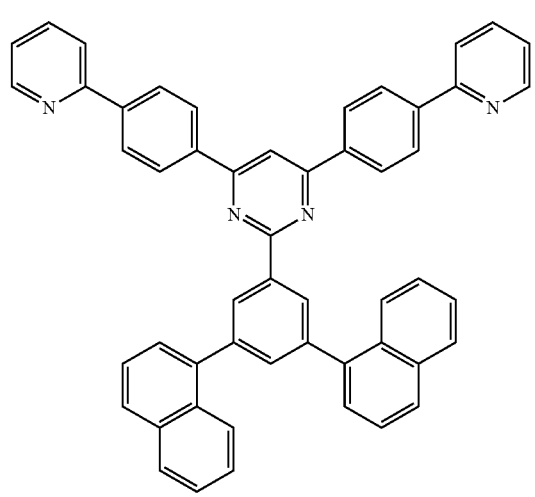
ET31
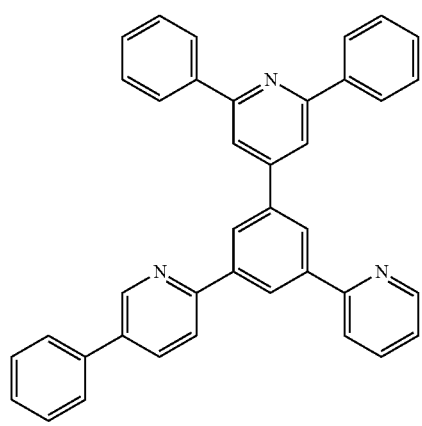
ET34
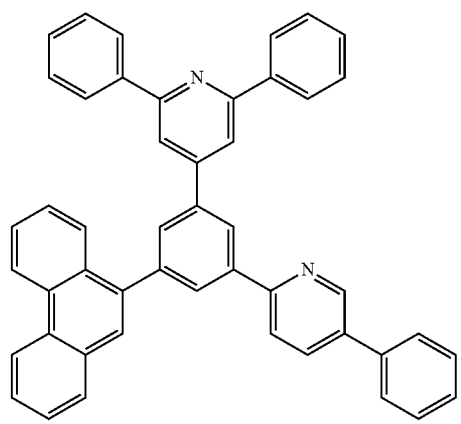

ET35

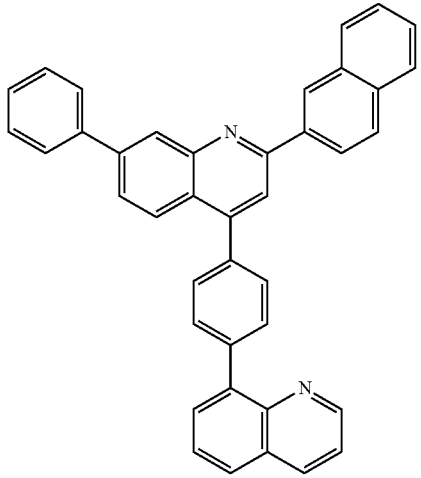

ET36

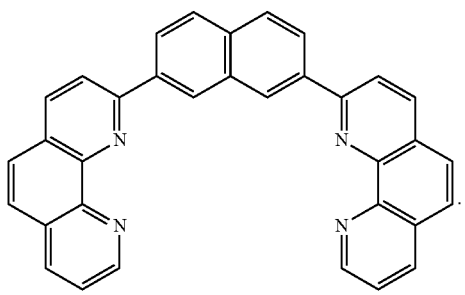

In one or more embodiments, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

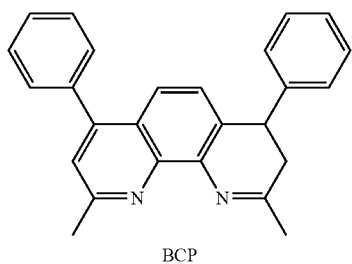

BCP

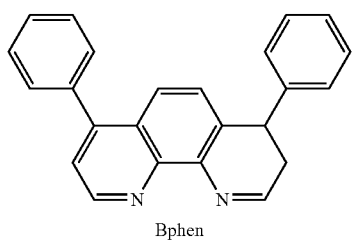

Bphen

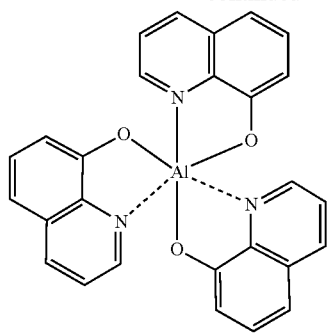

Alq₃

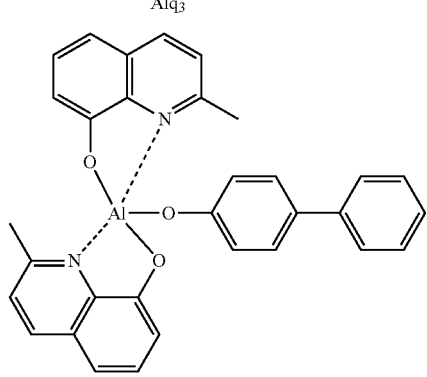

BAlq

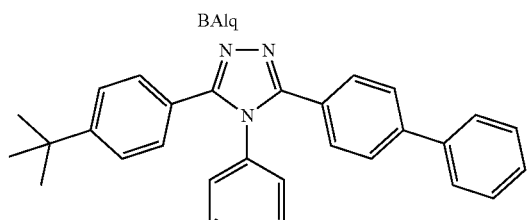

TAZ

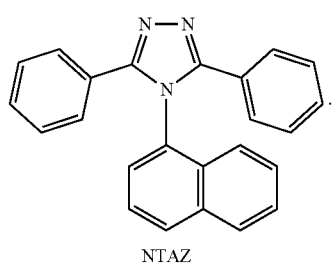

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, excellent hole blocking characteristics or electron control characteristics may be obtained without a substantial increase in driving voltage.

A thickness of the electron transport layer may be from about 100 Å to about 1,000 Å, for example, about 150 Å to about 500 Å. When the thickness of the electron transport layer is within the range described above, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2:

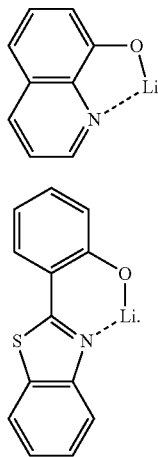

ET-D1

ET-D2

The electron transport region may include an electron injection layer that facilitates electron injection from the second electrode 190. The electron injection layer may directly contact (e.g., physically contact) the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth-metal may be selected from Mg, Ca, Sr, and Ba.

The rare earth-metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ ($0<x<1$), or $Ba_xCa_{1-x}O$ ($0<x<1$). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $Sc_2O_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include (e.g., consist of) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When a thickness of the electron injection layer is within these ranges, suitable or satisfactory electron injection characteristics may be obtained without substantial increase in driving voltage.

Second Electrode 190

The second electrode 190 may be on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
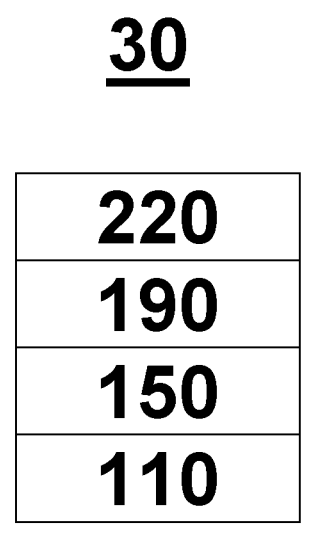
Figure 4:
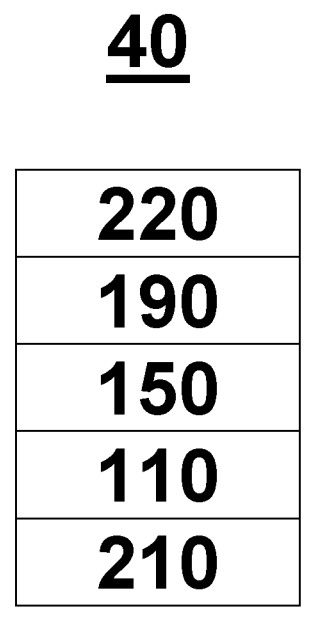

Description of FIGS. 2 to 4

Figure 2:
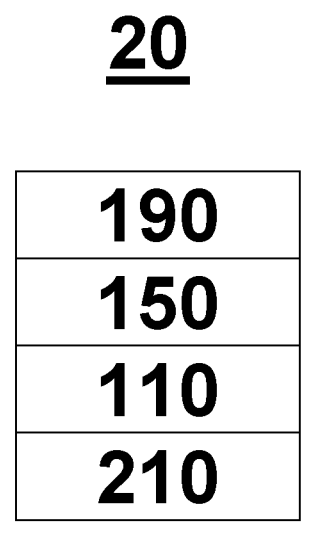

FIG. 2 is a schematic view of an organic light-emitting device 20 according to an embodiment. The organic light-emitting device 20 includes a first capping layer 210, the first electrode 110, the organic layer 150, and the second electrode 190, which are sequentially stacked in this stated order. FIG. 3 is a schematic view of an organic light-emitting device 30 according to an embodiment. The organic light-emitting device 30 includes the first electrode 110, the organic layer 150, the second electrode 190, and a second capping layer 220, which are sequentially stacked in this stated order. FIG. 4 is a schematic view of an organic light-emitting device 40 according to an embodiment. The organic light-emitting device 40 includes the first capping layer 210, the first electrode 110, the organic layer 150, the second electrode 190, and the second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110 and the first capping layer 210 toward the outside, wherein the first electrode 110 may be a semi-transmissive electrode or a transmissive electrode. In the organic layer 150 of each of the organic light-emitting devices 30 and 40, light generated in an emission layer may pass through the second electrode 190 and the second capping layer 220 toward the outside, wherein the second electrode 190 may be a semi-transmissive electrode or a transmissive electrode.

The first capping layer 210 and the second capping layer 220 may increase external luminescence efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

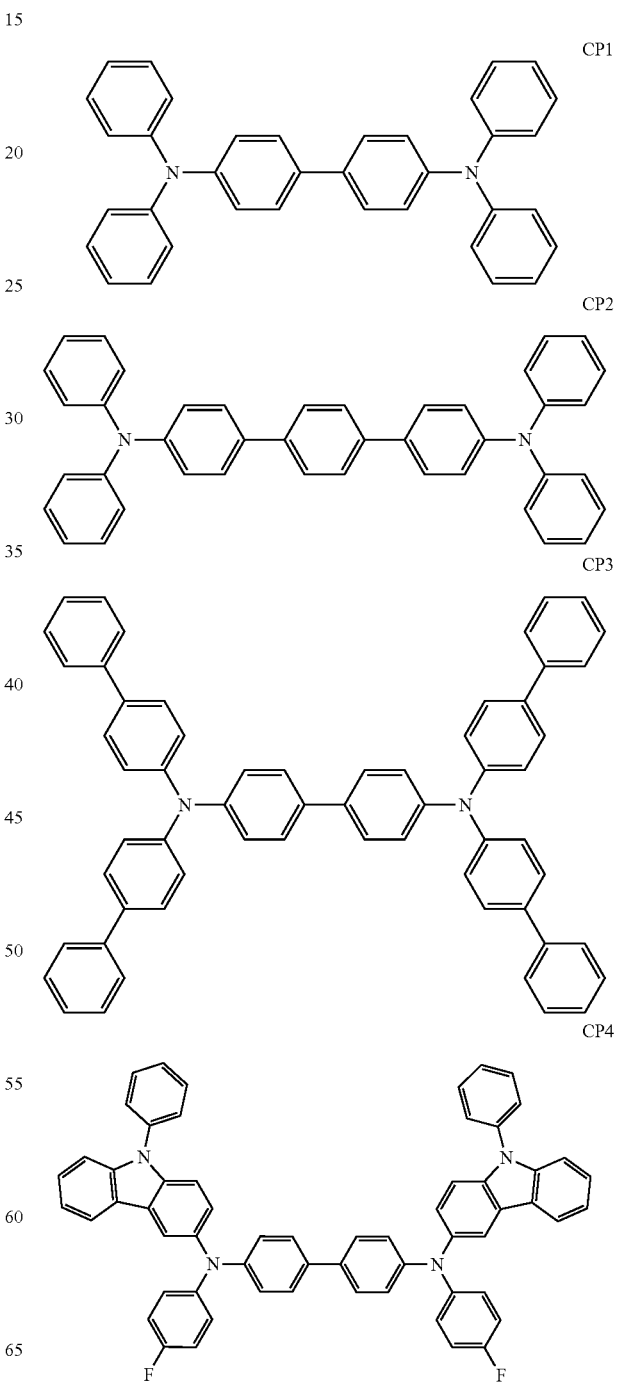

-continued

CP5

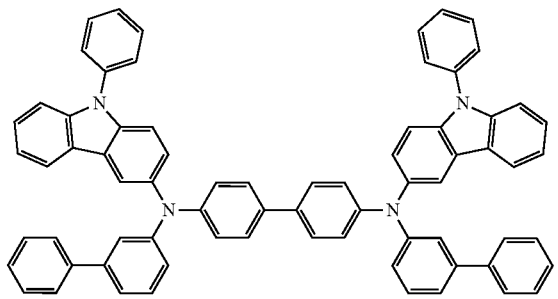

Hereinbefore, the organic light-emitting device according to an embodiment has been described in connection with FIGS. 1 to 4, but embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

Apparatus

The organic light-emitting device may be included in various suitable apparatuses. For example, a light-emitting apparatus, an authentication apparatus, or an electronic apparatus, which includes the organic light-emitting device, may be provided.

The light-emitting apparatus may further include, in addition to the organic light-emitting device, a thin film transistor including a source electrode and a drain electrode. One of the source electrode and the drain electrode of the thin film transistor may be in electrical contact with one of the first electrode and the second electrode of the organic light-emitting device. The light-emitting apparatus may be used as various suitable displays, light sources, and the like.

The authentication apparatus may be, for example, a biometric authentication apparatus for authenticating an individual by using biometric information of a biometric body (for example, a finger tip, a pupil, or the like).

The authentication apparatus may further include, in addition to the organic light-emitting device, a biometric information collector.

The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, or endoscope displays), fish finders, various suitable measuring instruments, meters (for example, meters for a vehicle, an aircraft, and a vessel), projectors, and the like, but embodiments of the present disclosure are not limited thereto.

General Definition of at Least Some Substituents

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminal end (e.g., at the terminus) of the $C_2$-$C_{60}$ alkyl group, and examples thereof include an ethenyl group, a propenyl group, and a butenyl group.

The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminal end (e.g., at the terminus) of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the ring and/or group is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, indicates —$OA_{102}$ (wherein $A_{102}$ is the $C_6$-$C_{60}$ aryl group), and the term "$C_6$-$C_{60}$ arylthio group," as used herein, indicates —$SA_{103}$ (wherein $A_{103}$ is the $C_6$-$C_{60}$ aryl group).

The term "$C_1$-$C_{60}$ heteroaryloxy group," as used herein, refers to —$OA_{104}$ (wherein $A_{104}$ is the $C_1$-$C_{60}$ heteroaryl group), and a $C_1$-$C_{60}$ heteroarylthio group used herein indicates —$SA_{105}$ (wherein $A_{105}$ is the $C_1$-$C_{60}$ heteroaryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire molecular structure is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecular structure is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The term "$C_5$-$C_{60}$ carbocyclic group," as used herein, refers to an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

In the present specification, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted or unsubstituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." For example, in some embodiments, the "terphenyl group" is a phenyl group having, as a substituent, a $C_6$-$C_{60}$ aryl group substituted with a $C_6$-$C_{60}$ aryl group.

\* and \*', as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples indicates that an identical molar equivalent of B was used in place of A.

EXAMPLE

Synthesis Example

Synthesis Example 1: Synthesis of Compound 1

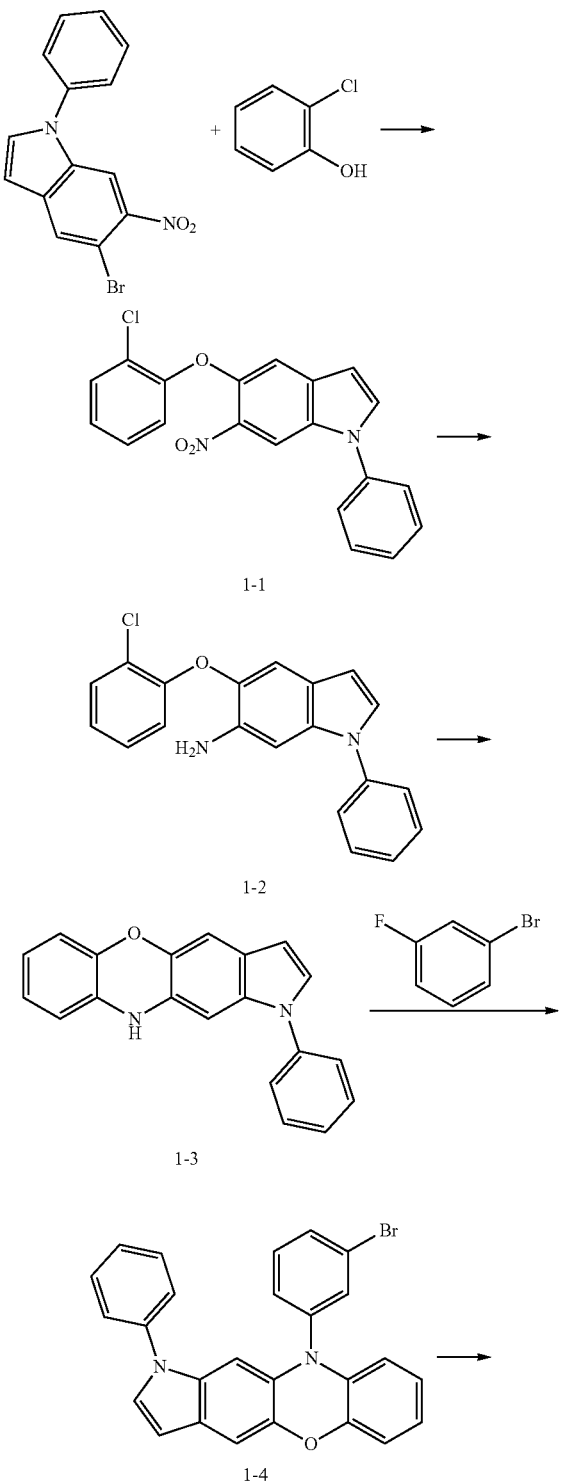

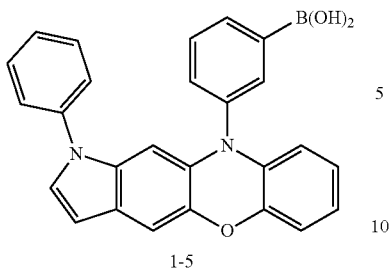

1-5

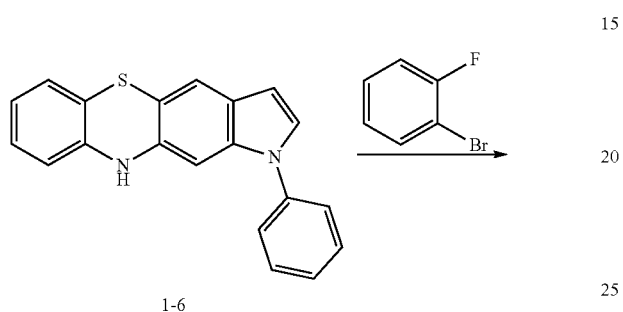

1-6

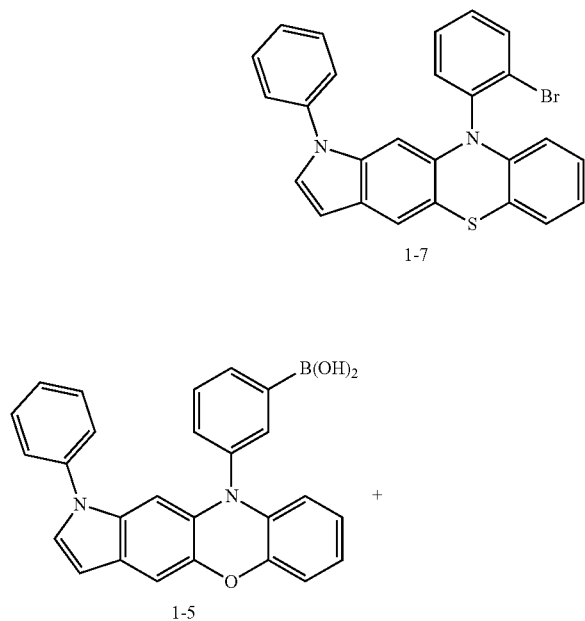

1-5

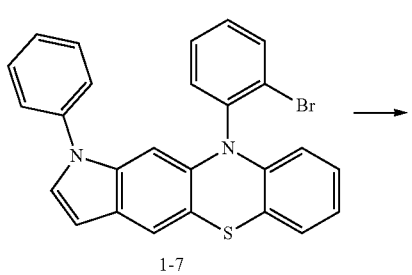

1-7

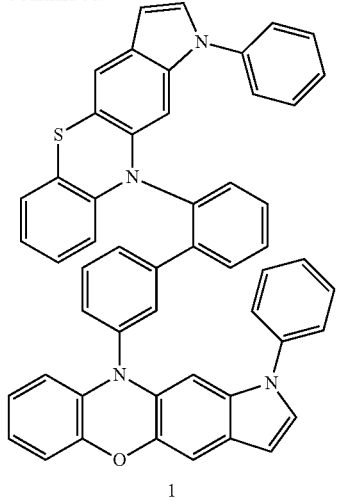

1

Synthesis of Intermediate 1-1

5-bromo-6-nitro-1-phenyl-1H-indole (CAS #=1616427-53-2) was reacted with 2-chlorophenol (CAS #=95-57-8) in the presence of a Cu catalyst to obtain Intermediate 1-1. Intermediate 1-1 was identified by liquid chromatography-mass spectrometry (LC-MS).

$C_{20}H_{13}ClN_2O_3$: M+1 365.13.

Synthesis of Intermediate 1-2

Intermediate 1-1 was reacted with ammonium chloride in the presence of ethanol to obtain Intermediate 1-2. Intermediate 1-2 was identified by LC-MS.

$C_{20}H_{15}ClN_2O$: M+1 335.08.

Synthesis of Intermediate 1-3

Intermediate 1-2 was reacted with sodium hydride in the presence of N,N-dimethylformamide to obtain Intermediate 1-3. Intermediate 1-3 was identified by LC-MS.

$C_{20}H_{14}N_2O$: M+1 299.24.

Synthesis of Intermediate 1-4

Intermediate 1-3 was reacted with 1-bromo-3-fluorobenzene (CAS #=1073-06-9) in the presence of a Pd catalyst to obtain Intermediate 1-4. Intermediate 1-4 was identified by LC-MS.

$C_{26}H_{17}BrN_2O$: M+1 453.03.

Synthesis of Intermediate 1-5

Intermediate 1-4 was reacted with nBuLi and then reacted with trimethylborate to obtain Intermediate 1-5. Intermediate 1-5 was identified by LC-MS.

$C_{26}H_{19}BN_2O_3$: M+1 419.33.

Synthesis of Intermediate 1-6

Intermediate 1-6 was synthesized in substantially the same manner as in Synthesis of Intermediate 1-3, except that 2-chlorobenzenethiol was used instead of 2-chlorophenol in Synthesis of Intermediate 1-1. Intermediate 1-6 was identified by LC-MS.

$C_{20}H_{14}N_2S$: M+1 315.15.

Synthesis of Intermediate 1-7

Intermediate 1-6 was reacted with 1-bromo-2-fluorobenzene (CAS #=1072-85-1) in the presence of a Pd catalyst to obtain Intermediate 1-7. Intermediate 1-7 was identified by LC-MS.

$C_{26}H_{17}BrN_2S$: M+1 469.12.

Synthesis of Compound 1

3.6 g of Intermediate 1-5, 4 g of Intermediate 1-7, 0.4 g of tetrakis(triphenylphosphine)palladium (a Pd catalyst), and 3 g of potassium carbonate were added to a reaction container, dissolved in 40 mL of toluene, 10 mL of ethanol, and 10 mL of distilled water, and then refluxed for 24 hours. After the reaction was completed, the reaction solution was extracted therefrom by using ethyl acetate. An organic layer collected therefrom was dried by using magnesium sulfate, and a residue obtained by evaporating a solvent therefrom was separated and purified by silica gel column chromatography to obtain 3.4 g (yield: 52%) of Compound 1. Compound 1 was identified by LC-MS and $^1$H-NMR.

Synthesis Example 2: Synthesis of Compound 15

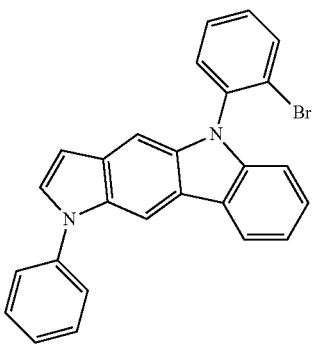

15-3

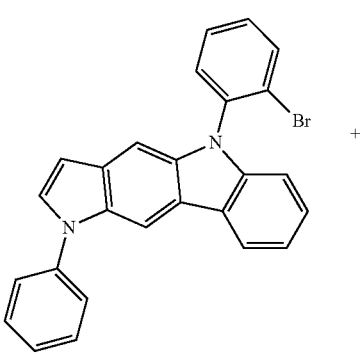

15-3

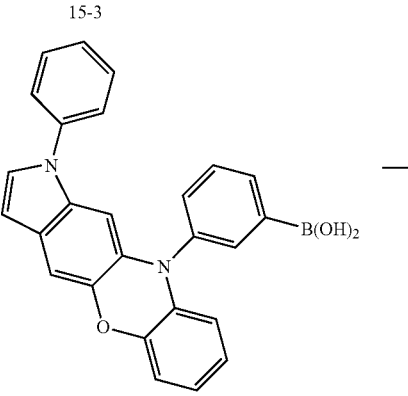

1-5

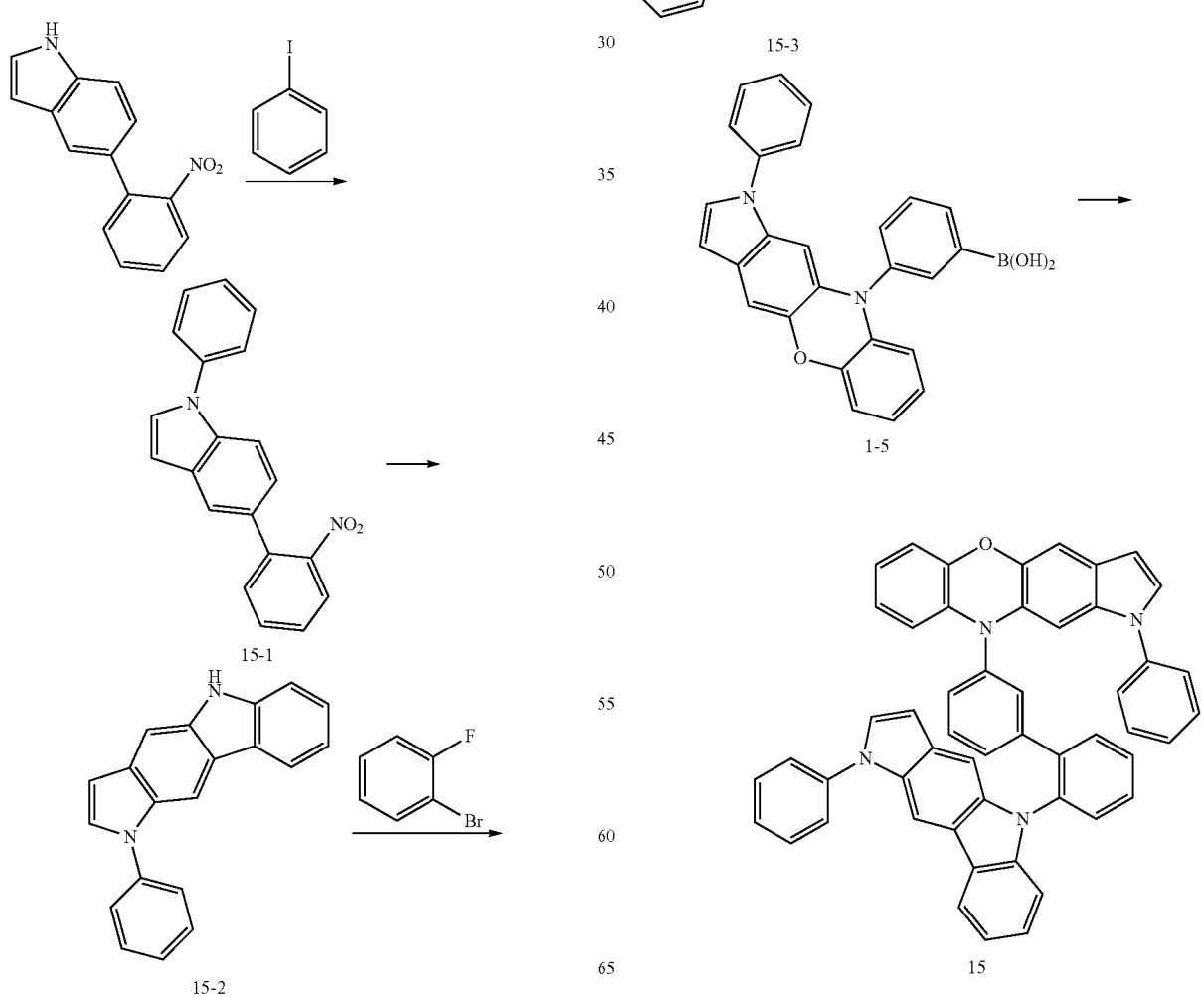

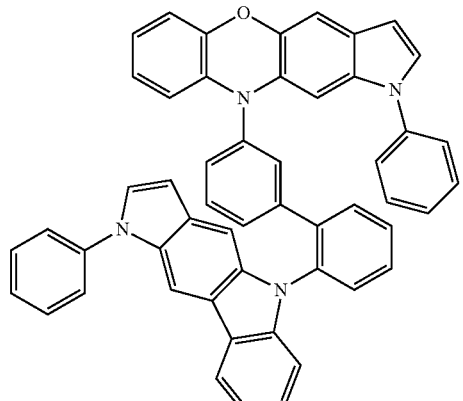

15

Synthesis of Intermediate 15-1

5-(2-nitrophenyl)-1H-indole (CAS #=599198-43-3) was reacted with iodobenzene (CAS #=591-50-4) in the presence of a Cu catalyst to obtain Intermediate 15-1. Intermediate 15-1 was identified by LC-MS.
$C_{20}H_{14}N_2O$: M+1 315.25.

Synthesis of Intermediate 15-2

Intermediate 15-1 was reacted with triphenylphosphine in the presence of o-dichlorobenzene to obtain Intermediate 15-2. Intermediate 15-2 was identified by LC-MS.
$C_{20}H_{14}N_2$: M+1 283.11.

Synthesis of Intermediate 15-3

Intermediate 15-2 was reacted with 1-bromo-2-fluorobenzene (CAS #=1072-85-1) in the presence of a Pd catalyst to obtain Intermediate 15-3. Intermediate 15-3 was identified by LC-MS.
$C_{26}H_{17}BrN_2$: M+1 437.11.

Synthesis of Compound 15

1.8 g (yield: 48%) of Compound 15 was synthesized in substantially the same manner as in Synthesis of Compound 1, except that Intermediate 15-3 was used instead of Intermediate 1-7. Compound 15 was identified by LC-MS and $^1$H-NMR.

Synthesis Example 3: Synthesis of Compound 18

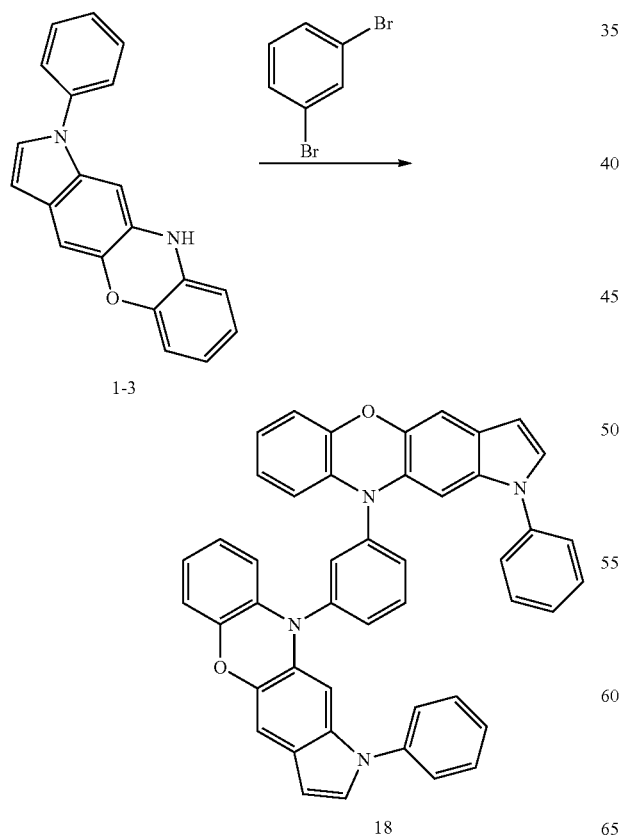

Synthesis of Compound 18

7 g of Intermediate 1-3, 2 g of 1,3-dibromobenzene, 1.5 g of sodium tert-butoxide, 0.3 g of tris(dibenzylideneacetone)dipalladium(0), and 0.3 mL of tri-tert-butylphosphine were dissolved in 40 mL of toluene and refluxed for 24 hours. After the reaction was completed, the reaction solution was extracted therefrom by using ethyl acetate. An organic layer collected therefrom was dried by using magnesium sulfate, and a residue obtained by evaporating a solvent therefrom was separated and purified by silica gel column chromatography to obtain 3.8 g (yield: 70%) of Compound 18. Compound 18 was identified by LC-MS and proton nuclear magnetic resonance spectroscopy (1H-NMR).

Synthesis Example 4: Synthesis of Compound 20

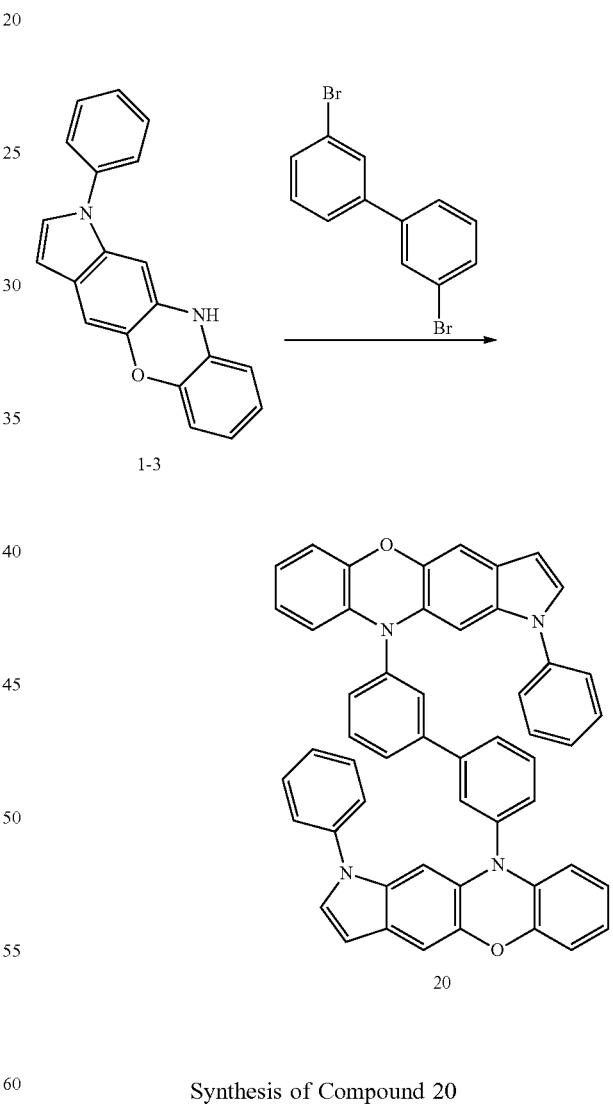

Synthesis of Compound 20

4.6 g (yield: 75%) of Compound 20 was synthesized in substantially the same manner as in Synthesis of Compound 18, except that 3,3-dibromo-1,1'-biphenyl was used instead of 1,3-dibromobenzene. Compound 20 was identified by LC-MS and $^1$H-NMR.

Synthesis Example 5: Synthesis of Compound 21

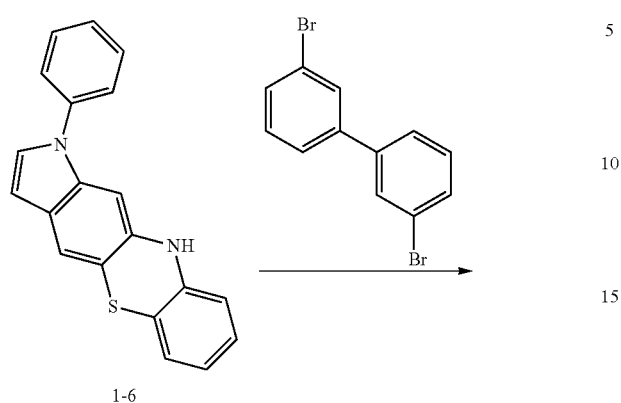

Synthesis of Compound 21

6.6 g (yield: 80%) of Compound 21 was synthesized in substantially the same manner as in Synthesis of Compound 20, except that Intermediate 1-6 was used instead of Intermediate 1-3. Compound 21 was identified by LC-MS and ¹H-NMR.

Synthesis Example 6: Synthesis of Compound 23

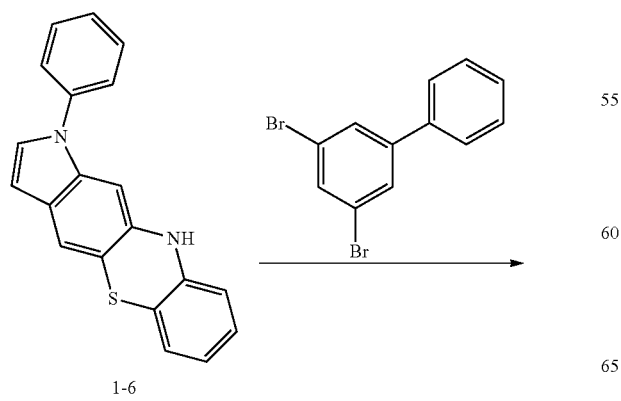

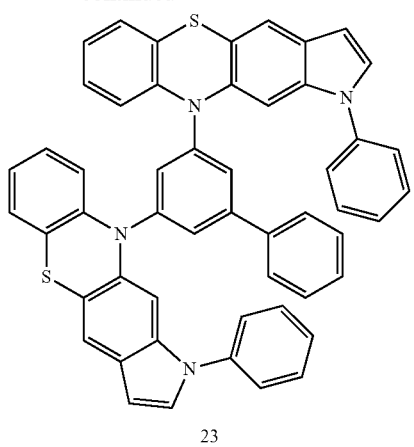

Synthesis of Compound 23

5.3 g (yield: 65%) of Compound 23 was synthesized in substantially the same manner as in Synthesis of Compound 21, except that 3,5-dibromo-1,1'-biphenyl was used instead of 3,3-dibromo-1,1'-biphenyl. Compound 23 was identified by LC-MS and ¹H-NMR.

Synthesis Example 7: Synthesis of Compound 30

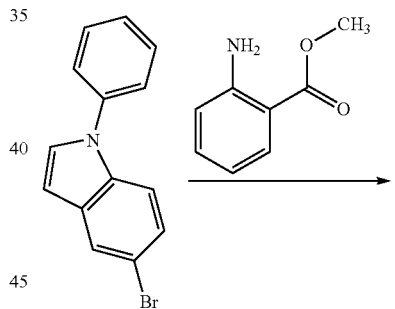

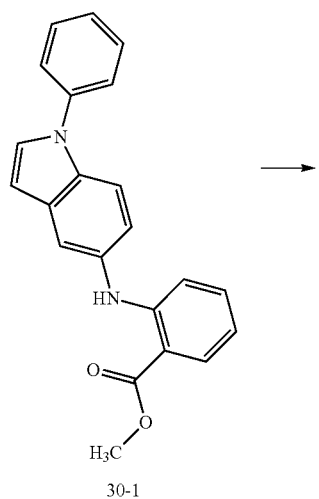

-continued

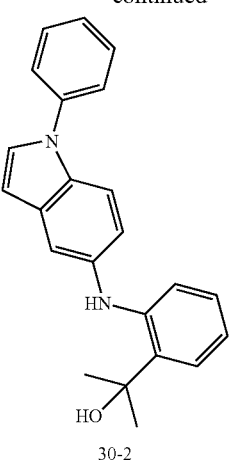

30-2

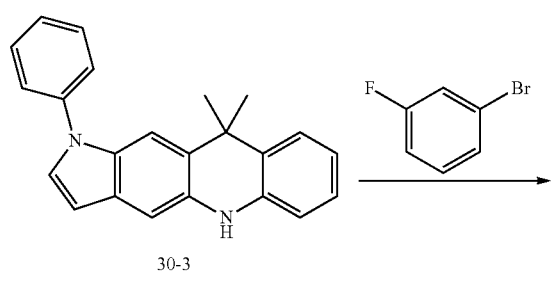

30-3

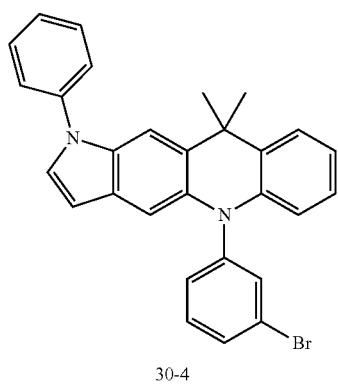

30-4

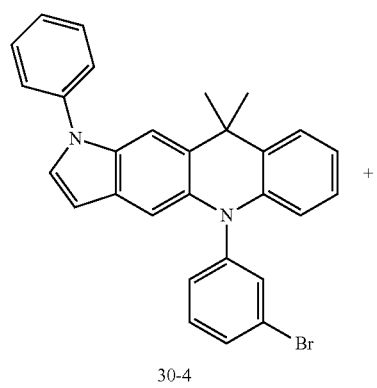

30-4

-continued

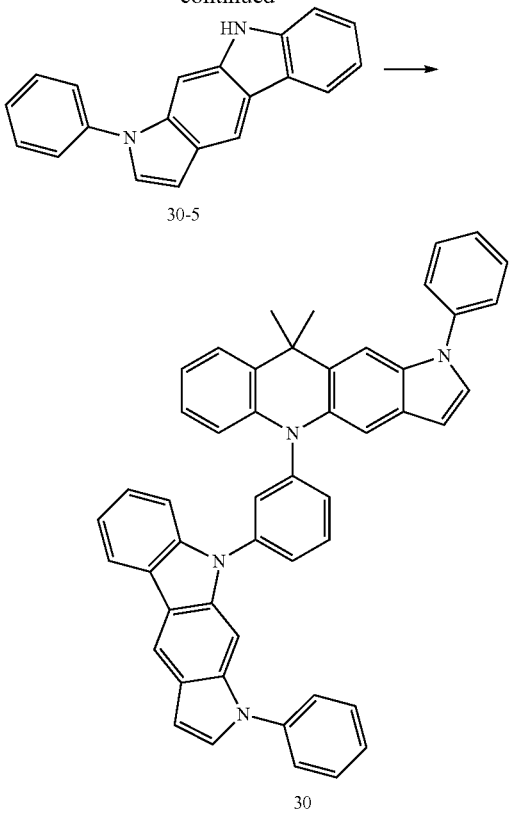

30-5

30

Synthesis of Intermediate 30-1

5-bromo-1-phenyl-1H-indole (CAS #=504424-70-8) was reacted with 2-(methoxycarbonyl)aniline (CAS #=134-20-3) in the presence of a Pd catalyst to obtain Intermediate 30-1. Intermediate 30-1 was identified by LC-MS.

$C_{22}H_{18}N_2O_2$: M+1 343.31.

Synthesis of Intermediate 30-2

Intermediate 30-1 was reacted with methylmagnesium bromide (CAS #=75-16-1) to obtain Intermediate 30-2. Intermediate 30-2 was identified by LC-MS.

$C_{23}H_{22}N_2O$: M+1 343.11.

Synthesis of Intermediate 30-3

Intermediate 30-2 was reacted in the presence of phosphoric acid to obtain Intermediate 30-3. Intermediate 30-3 was identified by LC-MS.

$C_{23}H_{20}N_2$: M+1 325.22.

Synthesis of Intermediate 30-4

Intermediate 30-3 was reacted with 1-bromo-3-fluorobenzene (CAS #=1073-06-9) in the presence of a Pd catalyst to obtain Intermediate 30-4. Intermediate 30-4 was identified by LC-MS.

$C_{29}H_{23}BrN_2$: M+1 479.09.

Synthesis of Intermediate 30-5

Intermediate 30-5 was synthesized in substantially the same manner as in Synthesis of Intermediate 15-2, except that Intermediate 30-5 was isolated instead of Intermediate 15-2. Intermediate 30-5 was identified by LC-MS.

$C_{20}H_{14}N_2$: M+1 283.13.

Synthesis of Compound 30

5 g of Intermediate 30-4, 3 g of Intermediate 30-5, 1.5 g of sodium tert-butoxide, 0.4 g of tris(dibenzylideneacetone)dipalladium(0), and 0.35 mL of tri-tert-butylphosphine were dissolved in 50 mL of toluene and refluxed for 24. After the reaction was completed, the reaction solution was extracted therefrom by using ethyl acetate. An organic layer collected therefrom was dried by using magnesium sulfate, and a residue obtained by evaporating a solvent therefrom was separated and purified by silica gel column chromatography to obtain 5 g (yield: 70%) of Compound 30. Compound 30 was identified by LC-MS and 1H-NMR.

Synthesis Example 8: Synthesis of Compound 31

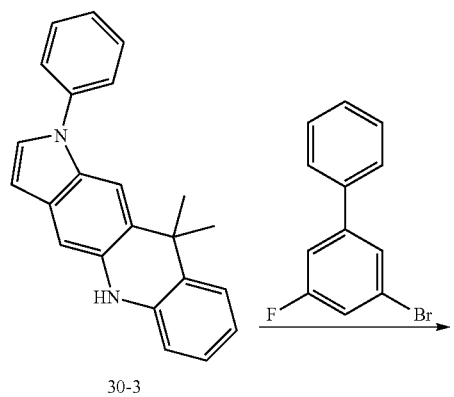

30-3

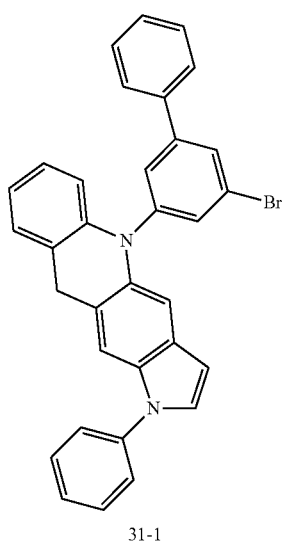

31-1

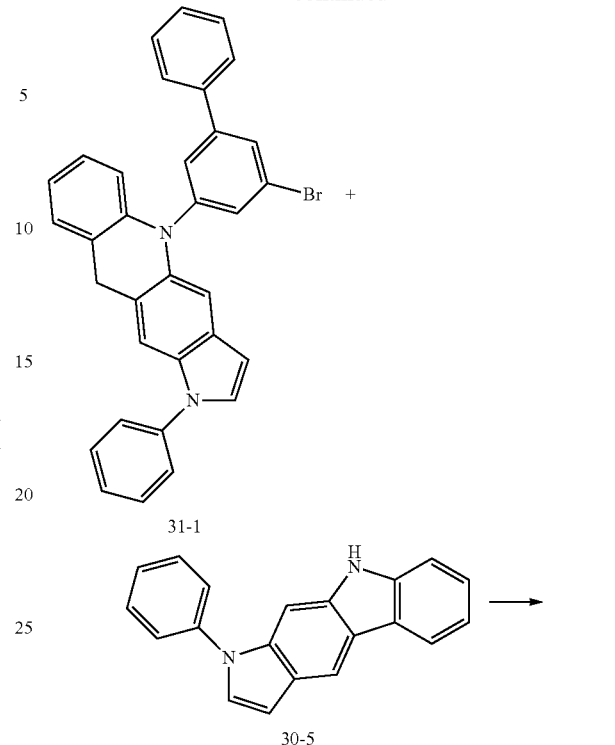

31-1

30-5

31

Synthesis of Intermediate 31-1

Intermediate 30-3 and 3-bromo-5-fluoro-1,1'-biphenyl (CAS #=136649-30-4) were reacted in the presence of a Pd catalyst to obtain Intermediate 31-1. Intermediate 31-1 was identified by LC-MS.

$C_{35}H_{27}BrN_2$: M+1 555.23.

Synthesis of Compound 31

5.2 g (yield: 67%) of Compound 31 was synthesized in substantially the same manner as in Synthesis of Compound 30, except that Intermediate 31-1 was used instead of Intermediate 30-4. Compound 31 was identified by LC-MS and $^1$H-NMR.

$^1$H NMR and mass-spectrometry-fast atom bombardment (MS/FAB) results for the Compounds synthesized in Synthesis Examples 1 to 8 are shown in Table 1.

Synthesis methods of compounds other than the Compounds shown in Table 1 may also be readily recognized by those of ordinary skill in the art by referring to the synthesis mechanisms and starting materials described above.

TABLE 1

| Synthesis Example | Compound | $^1$H NMR (CDCl$_3$, 400 MHz) | MS/FAB Found [M + 1] | calc. |
|---|---|---|---|---|
| 1 | 1 | 7.48-7.38 (11H, m), 7.28 (1H, d), 7.25 (1H, d), 7.24-7.22 (2H, m), 7.18-7.06 (4H, m), 6.97-6.77 (9H, m), 6.67 (1H, d), 6.57 (1H, s), 6.54 (1H, d), 6.47 (1H, d), 6.37 (1H, d), 6.29 (1H, d) | 763.41 | 762.25 |
| 2 | 15 | 8.18 (1H, d), 7.99 (1H, s), 7.70 (1H, s), 7.67 (1H, d), 7.45-7.37 (13H, m), 7.25-7.12 (7H, m), 6.97-6.77 (5H, m), 6.57-6.51 (3H, m), 6.37 (1H, q), 6.25 (1H, q) | 731.35 | 730.27 |
| 3 | 18 | 7.48-7.41 (10H, m), 7.30 (2H, m), 7.25 (2H, d), 7.08 (1H, t), 6.83-6.77 (6H, m), 6.57-6.54 (4H, m), 6.37-6.35 (3H, m), 6.30 (2H, q) | 671.15 | 670.24 |
| 4 | 20 | 7.48-7.38 (12H, m), 7.25 (2H, d), 7.20-7.18 (2H, m), 7.07 (2H, t), 6.92 (2H, t), 6.83-6.77 (6H, m), 6.57-6.54 (4H, m), 6.37 (2H, d), 6.32 (2H, q) | 747.26 | 746.27 |
| 5 | 21 | 7.48-7.38 (10H, m), 7.28 (2H, d), 7.24 (2H, m), 7.20-7.07 (8H, m), 6.94-6.89 (6H, m), 6.70 (2H, d), 6.47 (2H, d), 6.15 (2H, q) | 779.31 | 778.22 |
| 6 | 23 | 7.63-7.60 (2H, m), 7.48-7.40 (13H, m), 7.28 (2H, d), 7.24 (2H, m), 7.17 (2H, t), 7.03 (2H, d), 6.91 (2H, t), 6.86 (2H, t), 6.70 (2H, d), 6.69-6.67 (2H, m), 6.47-6.46 (2H, m), 6.37 (1H, t) | 779.29 | 778.22 |
| 7 | 30 | 8.27-8.20 (2H, m), 7.77 (1H, m), 7.66 (1H, d), 7.57 (1H, m), 7.48-7.37 (13H, m), 7.31-7.18 (5H, m), 7.02 (1H, t), 6.98-6.86 (3H, m), 6.65 (1H, d), 6.34 (1H, d), 5.87 (1H, d), 1.76 (3H, m), 1.67 (3H, m) | 681.35 | 680.29 |
| 8 | 31 | 8.31-8.25 (2H, m), 7.81 (1H, m), 7.79-7.76 (2H, m), 7.67 (1H, d), 7.49-7.39 (17H, m), 7.29-7.22 (2H, m), 6.98-6.86 (4H, m), 6.74 (1H, m), 6.67 (1H, t), 6.65 (1H, d), 6.53 (1H, t), 6.34 (1H, d), 1.76 (3H, m), 1.67 (3H, m) | 757.29 | 756.33 |

Example 1

A Corning (15 Ω/cm$^2$, 1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

NPB was vacuum-deposited on the ITO glass substrate to form a hole injection layer having a thickness of 300 Å, and TCTA was vacuum-deposited on the hole injection layer to form a hole transport layer having a thickness of 200 Å. CzSi was vacuum-deposited on the hole transport layer to form an electron blocking layer having a thickness of 100 Å.

Compound 1 and Ir(pmp)$_3$ were co-deposited on the electron blocking layer to a weight ratio of 92:8 to form an emission layer having a thickness of 250 Å. Then, TSPO1 was vacuum-deposited on the emission layer to form an electron transport layer having a thickness of 200 Å, and TPBI was vacuum-deposited on the electron transport layer to form an electron injection layer having a thickness of 300 Å. LiF was vacuum-deposited on the electron transport layer to a thickness of 10 Å and Al was vacuum-deposited a thickness of 3,000 Å to form a LiF/Al electrode, thereby completing the manufacture of an organic light-emitting device.

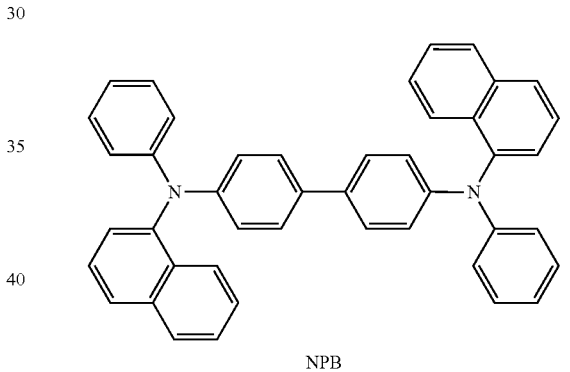

NPB

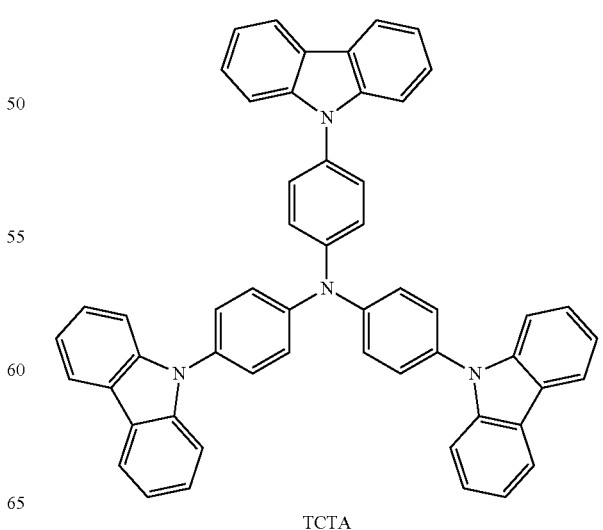

TCTA

-continued

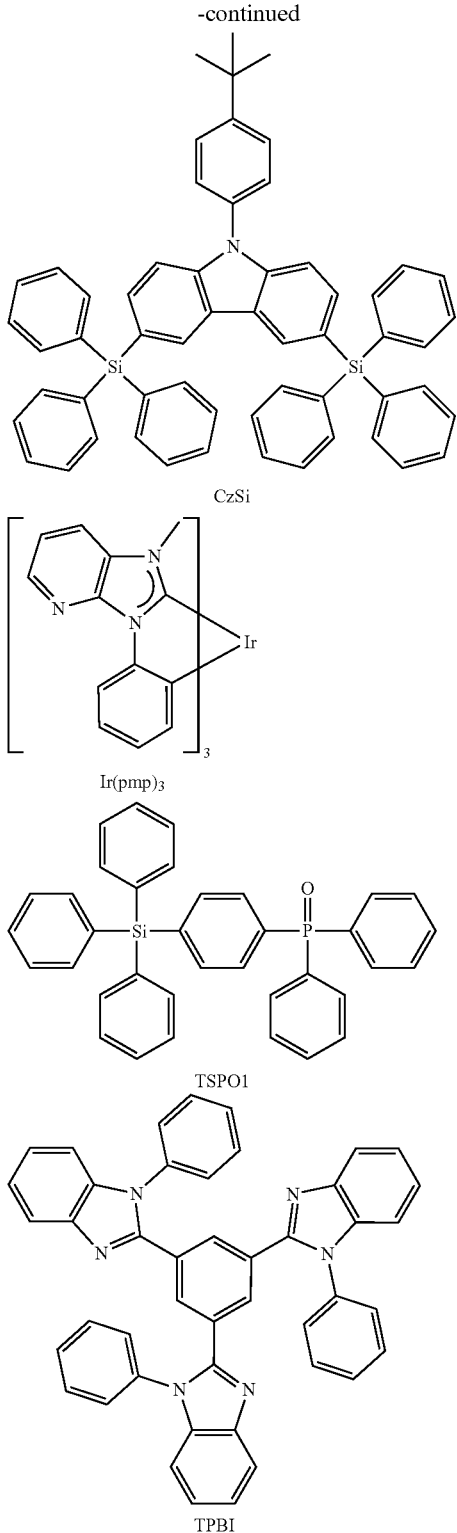

CzSi

Ir(pmp)₃

TSPO1

TPBI

Example 2

An organic light-emitting device was manufactured in substantially the same manner as in Example 1, except that Compound 15 was used instead of Compound 1 in forming an emission layer.

Example 3

An organic light-emitting device was manufactured in substantially the same manner as in Example 1, except that Compound 18 was used instead of Compound 1 in forming an emission layer.

Example 4

An organic light-emitting device was manufactured in substantially the same manner as in Example 1, except that Compound 20 was used instead of Compound 1 in forming an emission layer.

Example 5

An organic light-emitting device was manufactured in substantially the same manner as in Example 1, except that Compound 21 was used instead of Compound 1 in forming an emission layer.

Example 6

An organic light-emitting device was manufactured in substantially the same manner as in Example 1, except that Compound 23 was used instead of Compound 1 in forming an emission layer.

Example 7

An organic light-emitting device was manufactured in substantially the same manner as in Example 1, except that Compound 30 was used instead of Compound 1 in forming an emission layer.

Example 8

An organic light-emitting device was manufactured in substantially the same manner as in Example 1, except that Compound 31 was used instead of Compound 1 in forming an emission layer.

Comparative Example 1

An organic light-emitting device was manufactured in substantially the same manner as in Example 1, except that Comparative Compound 1 was used instead of Compound 1 in forming an emission layer.

Comparative Example 2

An organic light-emitting device was manufactured in substantially the same manner as in Example 1, except that Comparative Compound 2 was used instead of Compound 1 in forming an emission layer.

Comparative Example 3

An organic light-emitting device was manufactured in substantially the same manner as in Example 1, except that mCP was used instead of Compound 1 in forming an emission layer.

Comparative Compound 1

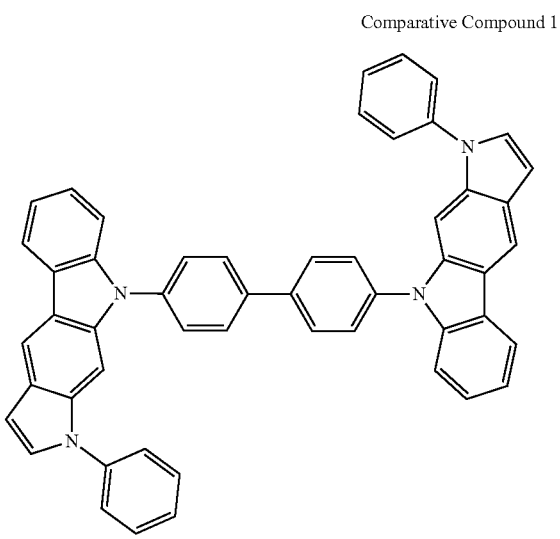

Comparative Compound 2

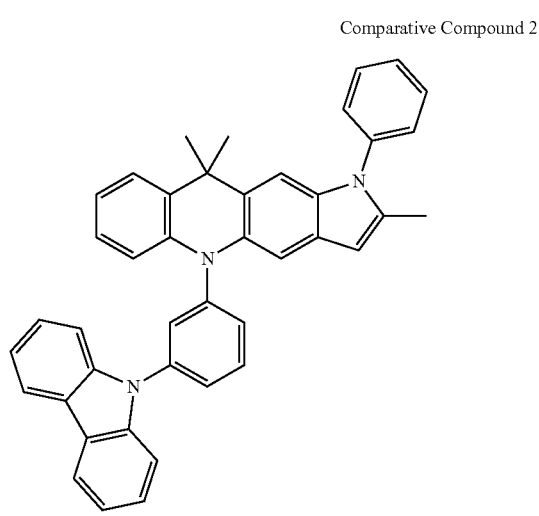

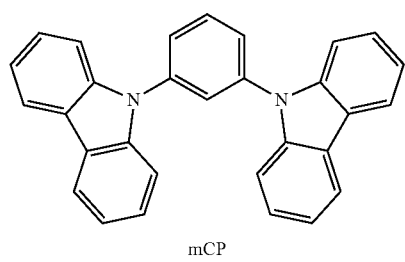

mCP

Evaluation Example

The driving voltage, current efficiency, and external quantum efficiency of the organic light-emitting devices manufactured according to Examples 1 to 8 and Comparative Examples 1 to 3 were measured at a current density of 10 mA/cm$^2$ by using a current-voltage meter (Keithley SMU 236) and a luminance meter (PR650), and results thereof are shown in Table 2.

TABLE 2

|  | Emission layer compound | Driving voltage (V) | Current efficiency (cd/A/y) | External quantum efficiency (%) |
|---|---|---|---|---|
| Example 1 | Compound 1 | 4.1 | 2.3 | 12.6 |
| Example 2 | Compound 15 | 4.3 | 2.3 | 12.5 |
| Example 3 | Compound 18 | 4.0 | 2.3 | 11.2 |
| Example 4 | Compound 20 | 4.1 | 2.3 | 12.2 |
| Example 5 | Compound 21 | 4.2 | 2.3 | 12.8 |
| Example 6 | Compound 23 | 4.2 | 2.3 | 13.3 |
| Example 7 | Compound 30 | 3.9 | 2.3 | 8.3 |
| Example 8 | Compound 31 | 4.0 | 2.3 | 9.5 |
| Comparative Example 1 | Comparative Compound 1 | 4.2 | 2.3 | 12.1 |
| Comparative Example 2 | Comparative Compound 2 | 4.0 | 2.3 | 9.1 |
| Comparative Example 3 | mCP | 4.3 | 2.3 | 11.8 |

Referring to Table 2, it can be seen that the organic light-emitting devices of Examples 1 to 8, in which the compounds according to one or more embodiments of the present disclosure are used in the emission layer have a low driving voltage and improved current efficiency and external quantum efficiency, as compared with the organic light-emitting devices of Comparative Examples 1 to 3.

According to embodiments of the present disclosure, the organic light-emitting device including the heterocyclic compound may have a low driving voltage, high efficiency, and a long lifespan.

It should be understood that embodiments described herein should be considered in a descriptive sense only and not for purposes of limitation. Descriptions of features or aspects within each embodiment should be considered as available for other similar features or aspects in other embodiments.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims, and equivalents thereof.

What is claimed is:
1. A heterocyclic compound represented by Formula 1:

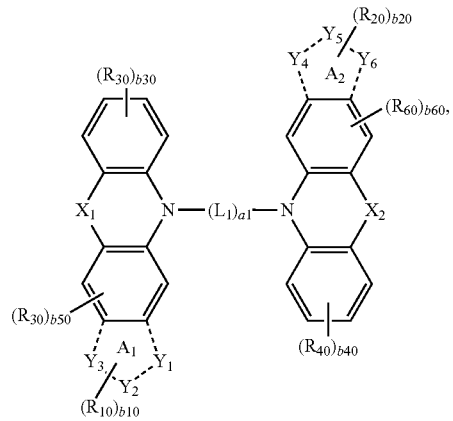

Formula 1 wherein, in Formula 1,
$X_1$ is a single bond O, S, $N(R_3)$, $C(R_4)(R_5)$, or $Si(R_4)(R_5)$,
$X_2$ is a single bond O, S, $N(R_6)$, $C(R_7)(R_8)$, or $Si(R_7)(R_8)$,
each of $X_1$ and $X_2$ is not both a single bond,
$A_1$ and $A_2$ are each independently a 5-membered $C_2$-$C_4$ heterocyclic group,
$Y_1$, $Y_2$, $Y_3$, $Y_4$, $Y_5$, and $Y_6$ are each independently selected from N, C, O, and S,
$L_1$ is selected from a substituted or unsubstituted $C_5$-$C_{60}$ carbocyclic group and a substituted or unsubstituted $C_1$-$C_{60}$ heterocyclic group,
a1 is an integer from 1 to 3,
$R_3$, $R_4$, $R_5$, $R_6$, $R_7$, $R_8$, $R_{10}$, $R_{20}$, $R_{30}$, $R_{40}$, $R_{50}$, and $R_{60}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$C(=O)(Q_1)$, —$N(Q_1)(Q_2)$, $P(=O)(Q_1)(Q_2)$, and —$S(=O)_2(Q_1)(Q_2)$,
b10 and b20 are each independently an integer from 0 to 3
b30 and b40 are each independently an integer from 0 to 4,
b50 and b60 are each independently an integer from 0 to 2,
at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The heterocyclic compound of claim 1, wherein:
$A_1$ and $A_2$ are each independently selected from a pyrrole group, a thiophene group, a furan group, a pyrazole group, an imidazole group, an oxazole group, an isoxazole group, a thiazole group, and an isothiazole group.

3. The heterocyclic compound of claim 1, wherein:
$L_1$ is selected from:
a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a phenylcarbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a phenylcarbazole group, a dibenzofuran group, and a dibenzothiophene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a phenylcarbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

4. The heterocyclic compound of claim 1, wherein:
L$_1$ is selected from groups represented by Formulae 3-1 to 3-46:
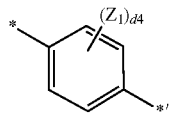
Formula 3-1
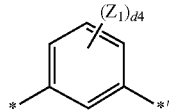
Formula 3-2
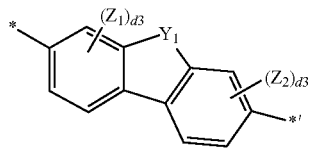
Formula 3-3
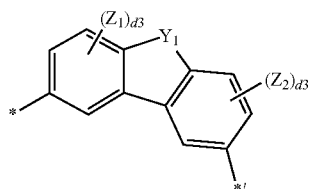
Formula 3-4
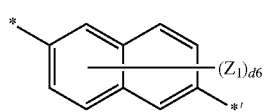
Formula 3-5
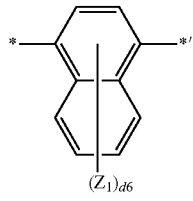
Formula 3-6
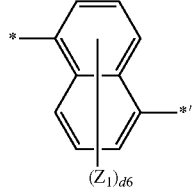
Formula 3-7
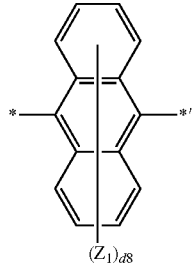
Formula 3-8
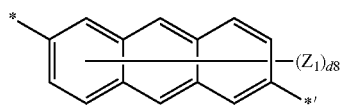
Formula 3-9
-continued
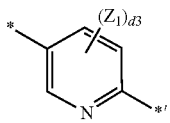
Formula 3-10
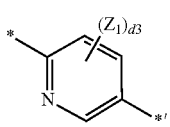
Formula 3-11
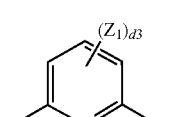
Formula 3-12
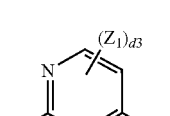
Formula 3-13
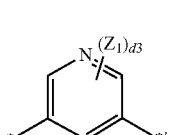
Formula 3-14
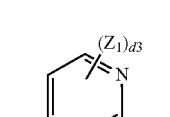
Formula 3-15
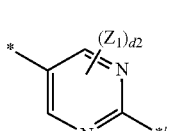
Formula 3-16
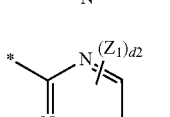
Formula 3-17
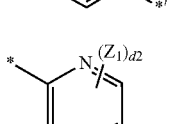
Formula 3-18
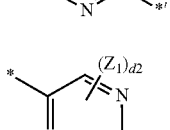
Formula 3-19
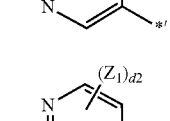
Formula 3-20
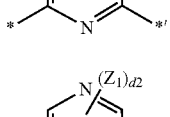
Formula 3-21

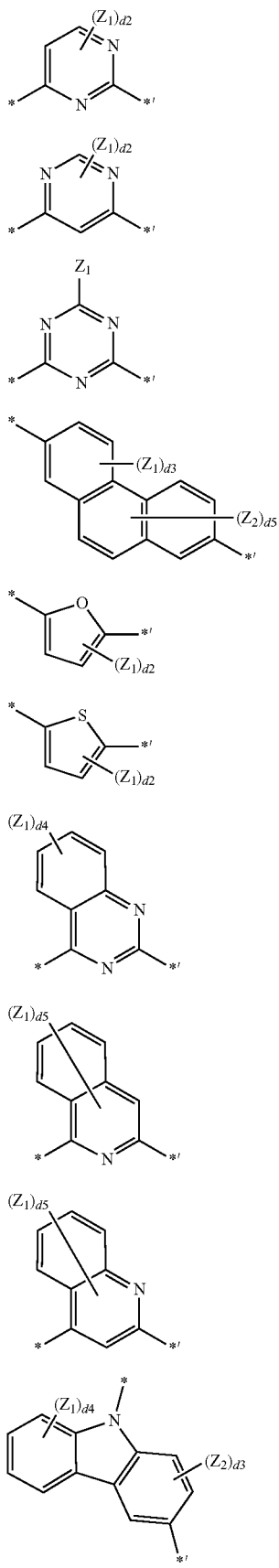
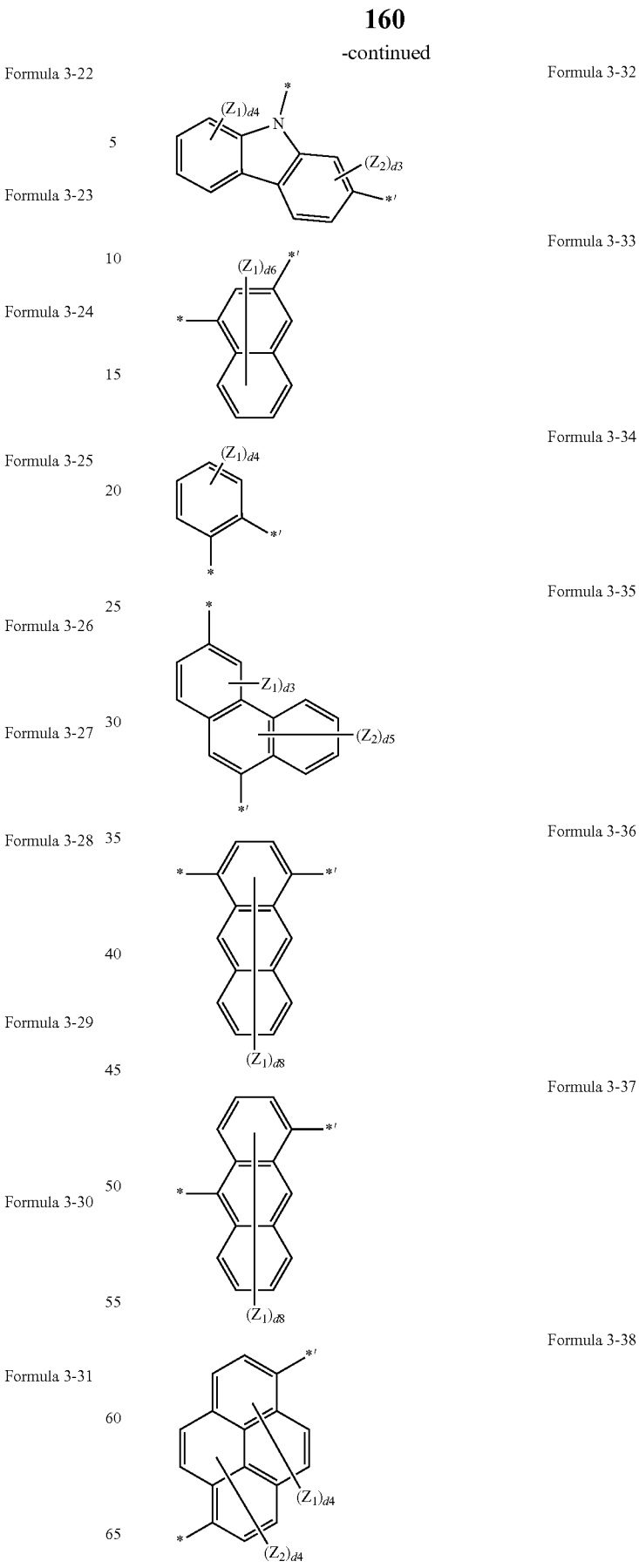

-continued

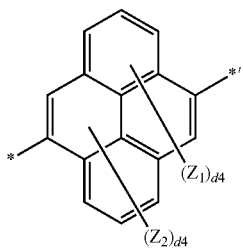
Formula 3-39

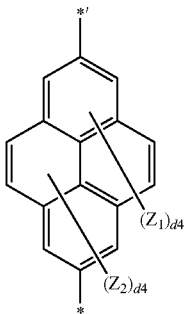
Formula 3-40

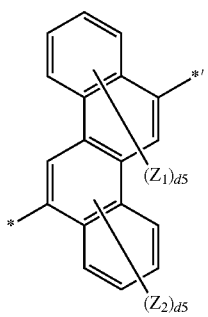
Formula 3-41

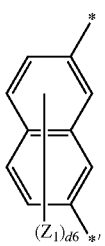
Formula 3-42

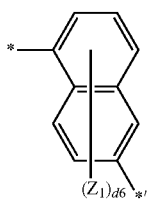
Formula 3-43

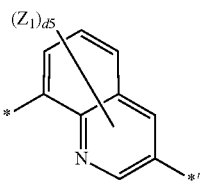
Formula 3-44

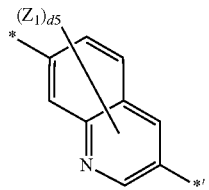
Formula 3-45

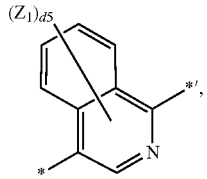
Formula 3-46 wherein, in Formulae 3-1 to 3-46, $Y_1$ is O, S, C($Z_3$)($Z_4$), N($Z_5$), or Si($Z_6$)($Z_7$), $Z_1$ to $Z_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenylcarbazolyl group, a phenanthridinyl group, an acridinyl group, a phenanthrolinyl group, a phenazinyl group, a triazinyl group, a dibenzofuranyl group, a dibenzothiophenyl group, —N($Q_{31}$)($Q_{32}$), —Si($Q_{31}$)($Q_{32}$)($Q_{33}$), and —B($Q_{31}$)($Q_{32}$), d2 is an integer from 0 to 2, wherein, when d2 is 2, two $Z_1$(s) are identical to or different from each other, d3 is an integer from 0 to 3, wherein, when d3 is 2 or more, two or more $Z_1$(s) and two or more $Z_2$(s) are identical to or different from each other, d4 is an integer from 0 to 4, wherein, when d4 is 2 or more, two or more $Z_1$(s) and two or more $Z_2$(s) are identical to or different from each other, d5 is an integer from 0 to 5, wherein, when d5 is 2 or more, two or more $Z_1$(s) and two or more $Z_2$(s) are identical to or different from each other, d6 is an integer from 0 to 6, wherein, when d6 is 2 or more, two or more $Z_1$(s) and two or more $Z_2$(s) are identical to or different from each other, d8 is an integer from 0 to 8, wherein, when d8 is 2 or more, two or more $Z_1$(s) are identical to or different from each other, $Q_{31}$ to $Q_{33}$ are each independently selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

* and *' each indicate a binding site to a neighboring atom.

5. The heterocyclic compound of claim 1, wherein:

$R_3$, $R_4$, $R_5$, $R_6$, $R_7$, $R_8$, $R_{10}$, $R_{20}$, $R_{30}$, $R_{40}$, $R_{50}$, and $R_{60}$ are each independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, a pyridoindolyl group, an indazolyl group, a purinyl group, a quinolinyl group, an isoquinolinyl group, a benzoquholinyl group, a phthalazinyl group, a naphthyndinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, a pyridoindolyl group, an indazolyl group, a purinyl group, a quinolinyl group, an isoquinolinyl group, a benzoquholinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)$_2$($C_1$), and —P(=O)($Q_1$)($Q_2$), and $Q_1$ to $Q_3$ and $Q_{31}$ to $Q_{33}$ are each independently selected from:

a $C_1$-$C_{20}$ alkyl group, a $C_1$-$C_{20}$ alkoxy group, a phenyl group, a biphenyl group, and a terphenyl group; and a phenyl group substituted with at least one selected from —F, —Cl, —Br, —I, a cyano group, a $C_1$-$C_{20}$ alkyl group, and a $C_1$-$C_{20}$ alkoxy group.

6. The heterocyclic compound of claim 1, wherein:

$R_4$, $R_5$, $R_7$, $R_8$, $R_{30}$, $R_{40}$, $R_{50}$, and $R_{60}$ are each independently selected from:

hydrogen, deuterium, —F, —Cl, —Br, —I, a methyl group, an ethyl group, an n-propyl group, an isopropyl group, an n-butyl group, a sec-butyl group, an isobutyl group, a tert-butyl group, an ethenyl group, a propenyl group, a butenyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group; and a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group, each substituted with at least one selected from deuterium, —F, —Cl, —Br, —I, a cyano group, a phenyl group, and a biphenyl group, $R_3$, $R_6$, $R_{10}$, and $R_{20}$ are each independently selected from groups represented by Formulae 5-1 to 5-32:

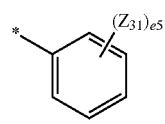

Formula 5-1

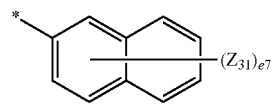

Formula 5-2

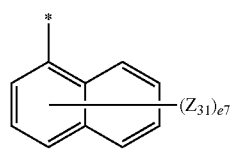

Formula 5-3

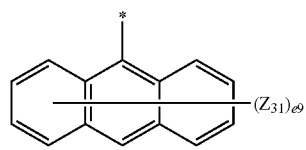

Formula 5-4

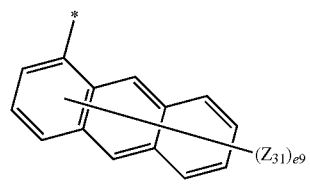

Formula 5-5

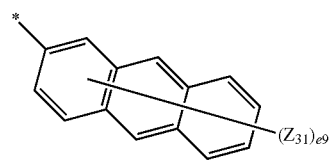

Formula 5-6

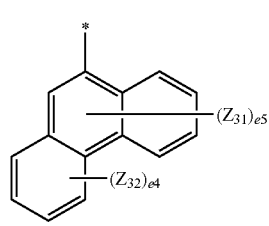

Formula 5-7

-continued

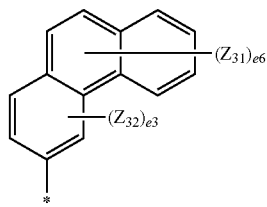

Formula 5-8

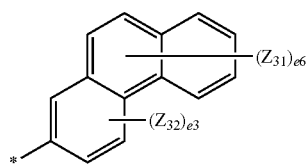

Formula 5-9

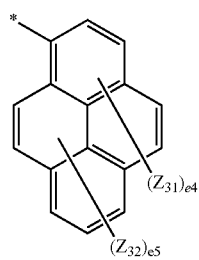

Formula 5-10

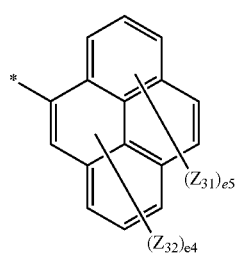

Formula 5-11

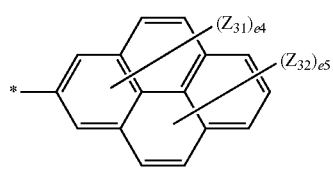

Formula 5-12

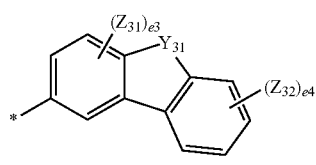

Formula 5-13

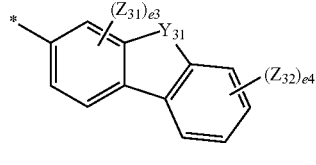

Formula 5-14

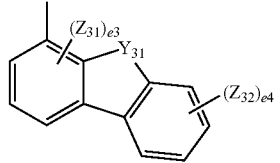

Formula 5-15

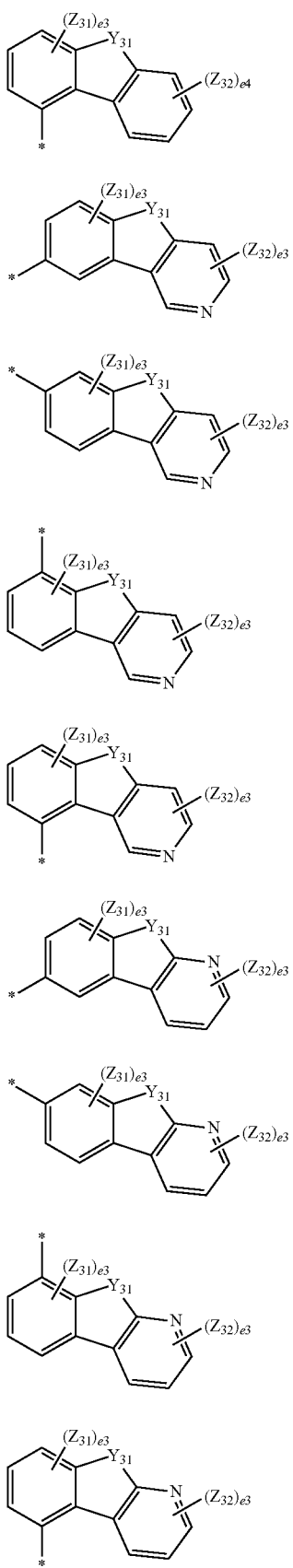

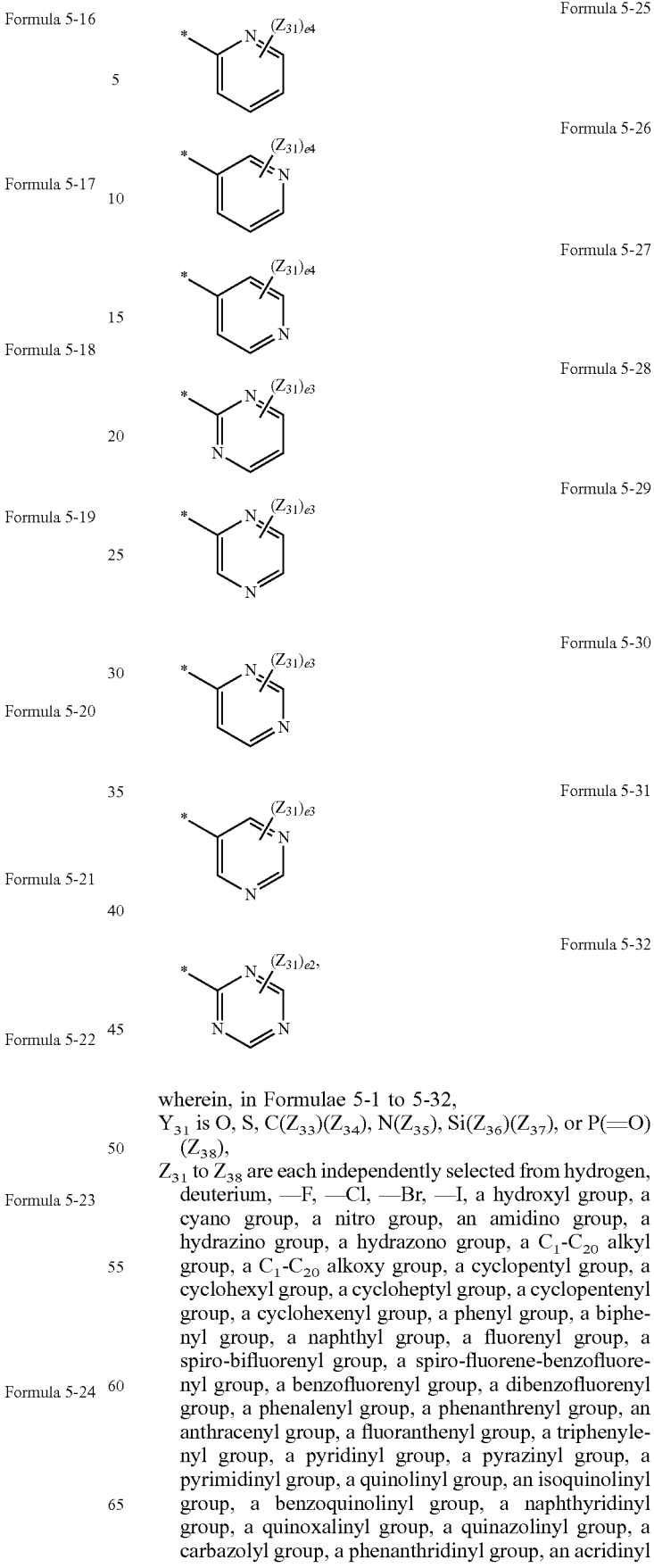

wherein, in Formulae 5-1 to 5-32, $Y_{31}$ is O, S, $C(Z_{33})(Z_{34})$, $N(Z_{35})$, $Si(Z_{36})(Z_{37})$, or $P(=O)(Z_{38})$, $Z_{31}$ to $Z_{38}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —Si(Q$_{31}$)(Q$_{32}$)(Q$_{33}$) and P(=O)(Q$_{31}$)(Q$_{32}$), Q$_1$ to Q$_3$ and Q$_{31}$ to Q$_{33}$ are each independently selected from a C$_1$-C$_{20}$ alkyl group, a C$_1$-C$_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, e2 is an integer from 0 to 2, wherein, when e2 is 2, two Z$_{31}$(S) are identical to or different from each other, e3 is an integer from 0 to 3, wherein, when e3 is 2 or more, two or more Z$_{31}$(s) and two or more Z$_{32}$(s) are identical to or different from each other, e4 is an integer from 0 to 4, wherein, when e4 is 2 or more, two or more Z$_{31}$(s) and two or more Z$_{32}$(s) are identical to or different from each other, e5 is an integer from 0 to 5, wherein, when e5 is 2 or more, two or more Z$_{31}$(s) and two or more Z$_{32}$(s) are identical to or different from each other, e6 is an integer from 0 to 6, wherein, when e6 is 2 or more, two or more Z$_{31}$(s) and two or more Z$_{32}$(s) are identical to or different from each other, e7 is an integer from 0 to 7, wherein, when e7 is 2 or more, two or more Z$_{31}$(s) are identical to or different from each other, e9 is an integer from 0 to 9, wherein, when e9 is 2 or more, two or more Z$_{31}$(s) are identical to or different from each other, and

* indicates a binding site to a neighboring atom.

7. The heterocyclic compound of claim 1, wherein:
the compound of Formula 1 is represented by one selected from Formulae 1-1 to 1-3:

Formula 1-1

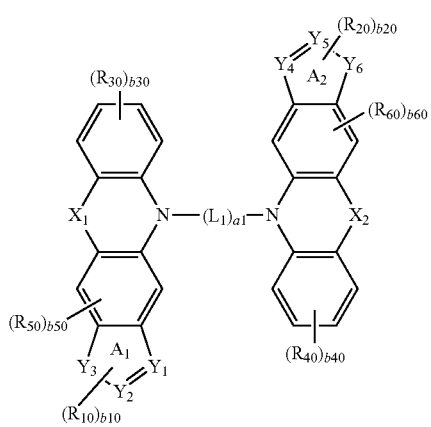

Formula 1-2

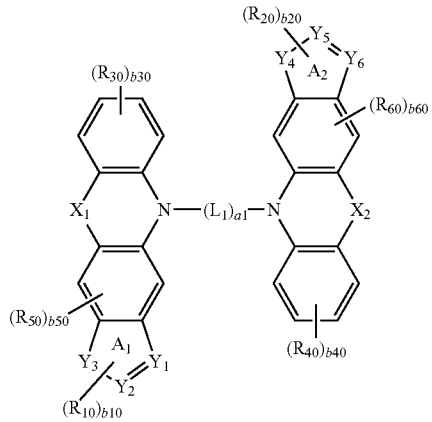

Formula 1-3

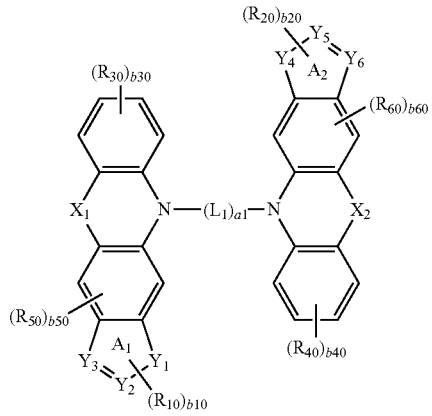

wherein, in Formulae 1-1 to 1-3,

X$_1$, X$_2$, A$_1$, A$_2$, R$_{10}$, R$_{20}$, R$_{30}$, R$_{40}$, R$_{50}$, a1, b10, b20, b30, b40, b50, and b60 are each independently the same as defined in claim 1, and Y$_1$, Y$_2$, Y$_3$, Y$_4$, Y$_5$, and Y$_6$ are each independently N connected by a single bond only, or are each independently N or C connected by a double bond.

8. The heterocyclic compound of claim 7, wherein:

L$_1$ is selected from:

a phenylene group, a naphthylene group, a fluorenylene group, an anthracenylene group, a pyridinylene group, a carbazolylene group, a dibenzofuranylene group, a dibenzothiophenylene group, a dibenzosilolylene group, and a pyridoindolylene group; and a phenylene group, a naphthylene group, a fluorenylene group, an anthracenylene group, a pyridinylene group, a carbazolylene group, a dibenzofuranylene group, a dibenzothiophenylene group, a dibenzosilolylene group, and a pyridoindolylene group, each substituted with at least one selected from deuterium, —F, —Cl, —Br, —I, a C$_1$-C$_{20}$ alkyl group, a C$_1$-C$_{20}$ alkoxy group, a phenyl group, a biphenyl group, a naphthyl group, a carbazolyl group, and a phenylcarbazolyl group.

9. The heterocyclic compound of claim 7, wherein:

$R_4$, $R_5$, $R_7$, $R_8$, $R_{30}$, $R_{40}$, $R_{50}$, and $R_{60}$ are each independently selected from hydrogen, deuterium, —F, —Cl, —Br, —I, a methyl group, an ethyl group, an n-propyl group, an isopropyl group, an n-butyl group, a sec-butyl group, an isobutyl group, a tert-butyl group, an ethenyl group, a propenyl group, a butenyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, and a naphthyl group, $R_3$, $R_6$, $R_{10}$, and $R_{20}$ are each independently selected from:

a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group; and a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, and a naphthyl group.

10. The heterocyclic compound of claim 7, wherein:

$L_1$ is selected from:

a phenylene group, a naphthylene group, an anthracenylene group, and a fluorenylene group; and a phenylene group, a naphthylene group, an anthracenylene group, and a fluorenylene group, each substituted with at least one selected from a phenyl group, a biphenyl group, a naphthyl group, a carbazolyl group, and a phenylcarbazolyl group, $R_4$, $R_5$, $R_7$, $R_8$, $R_{30}$, $R_{40}$, $R_{50}$, and $R_{60}$ are each independently selected from hydrogen, a methyl group, an ethyl group, an n-propyl group, an isopropyl group, a methoxy group, an ethoxy group, an n-propoxy group, an isopropoxy group, a phenyl group, a biphenyl group, and a naphthyl group, and $R_3$, $R_6$, $R_{10}$, and $R_{20}$ are each independently selected from:

a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group; and a phenyl group, a naphthyl group, a fluorenyl group, an anthracenyl group, a pyridinyl group, a carbazolyl group, a dibenzofuranyl group, a dibenzothiophenyl group, a dibenzosilolyl group, and a pyridoindolyl group, each substituted with at least one selected from a phenyl group, a biphenyl group, and a naphthyl group.

11. The heterocyclic compound of claim 1, wherein:

the compound of Formula 1 is selected from Compounds 1 to 33:

1

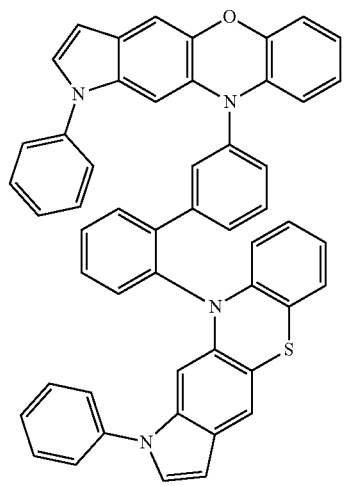

2

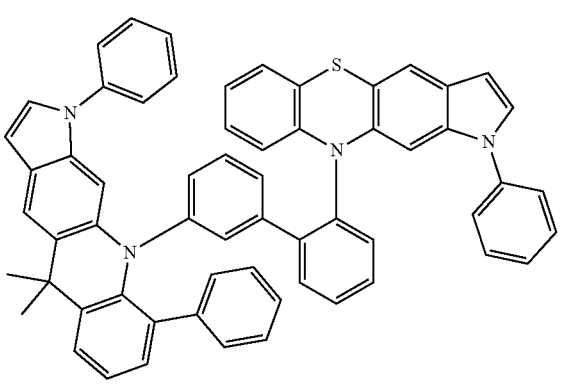

3

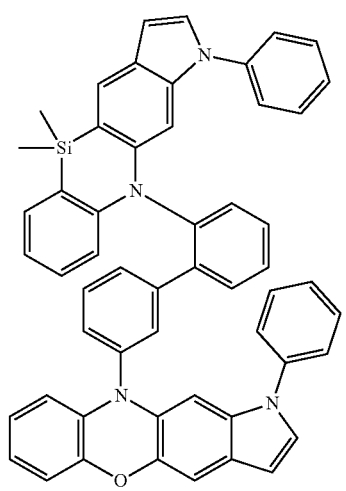

4
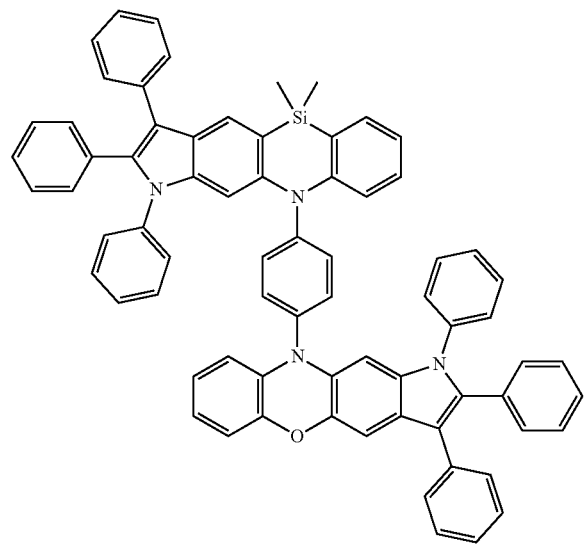
5
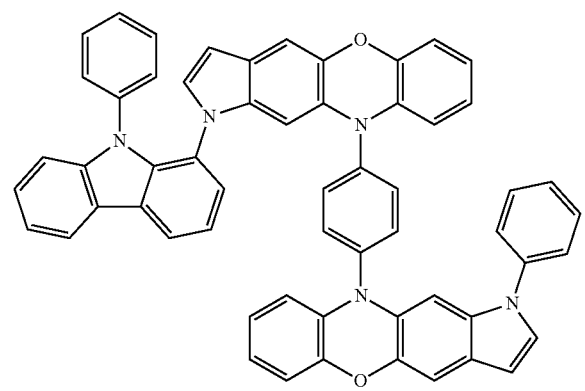
6
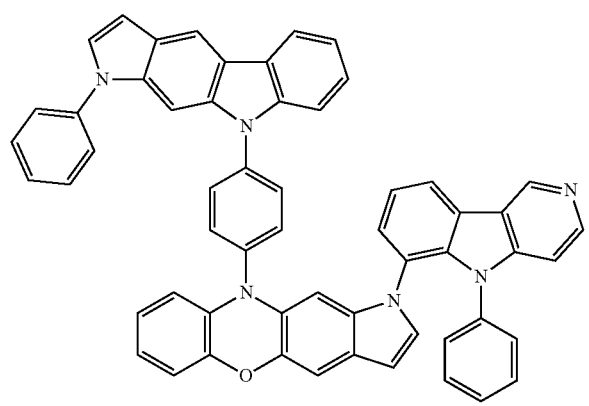
7
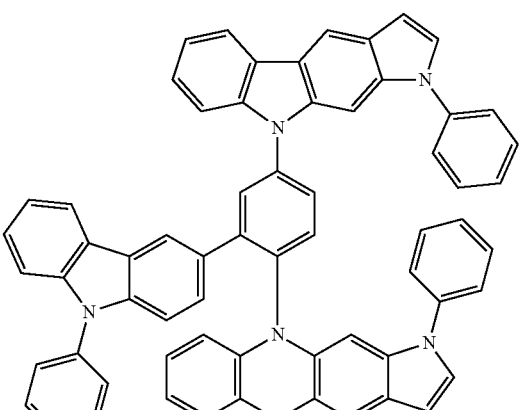
8
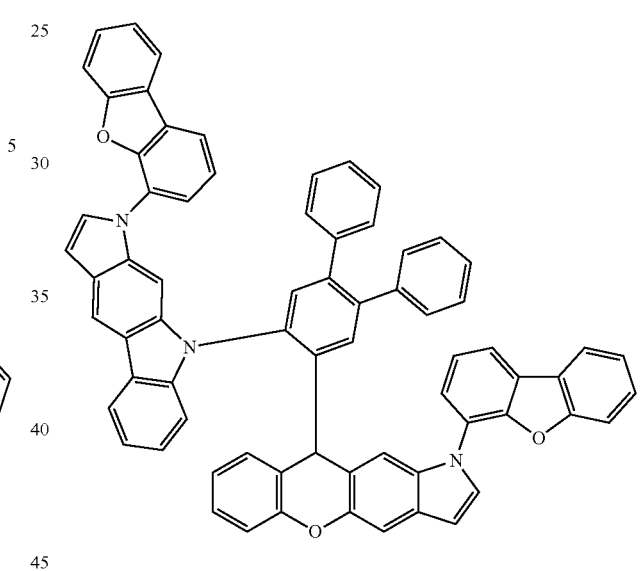
9
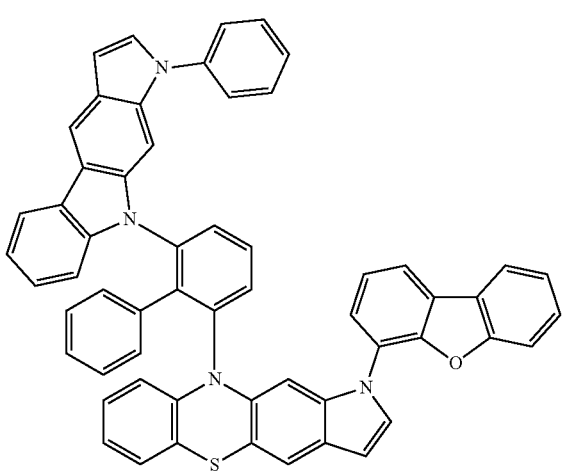

-continued
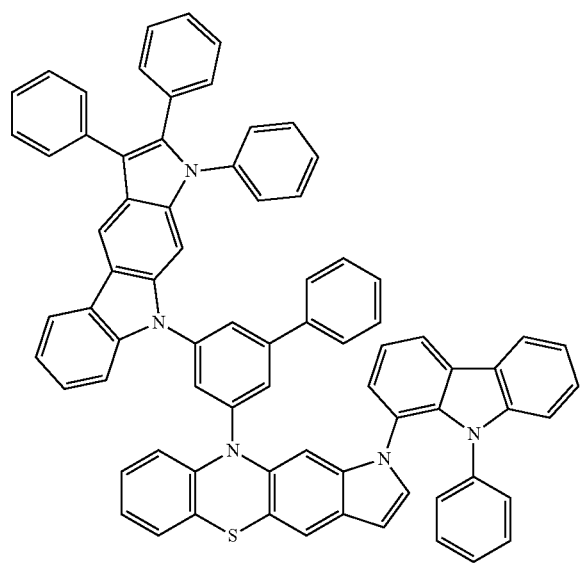
10
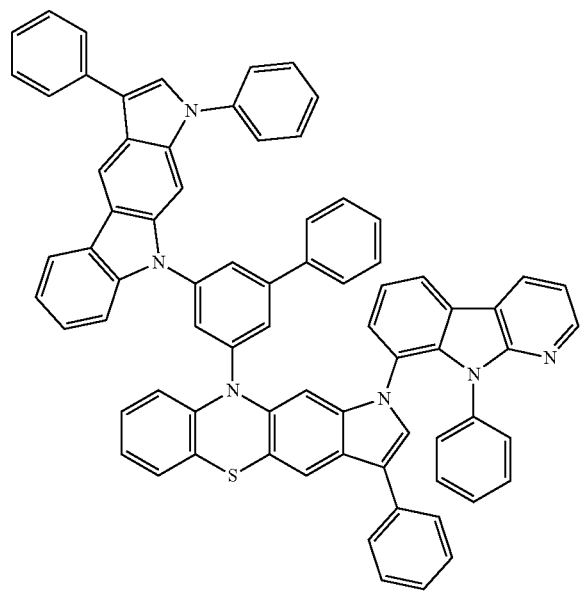
11
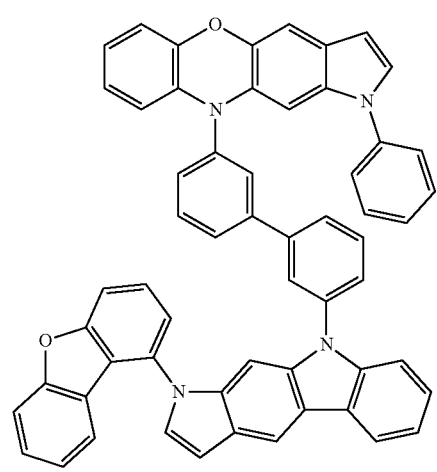
12
-continued
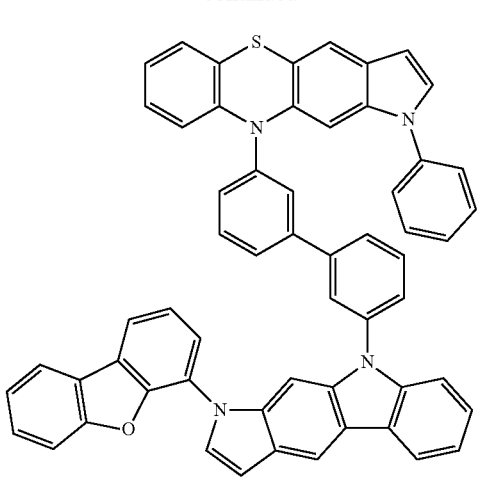
13
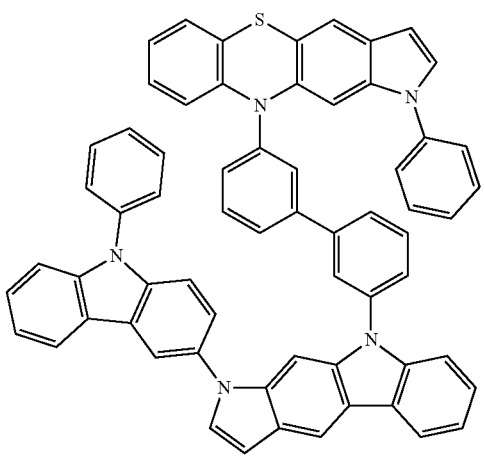
14
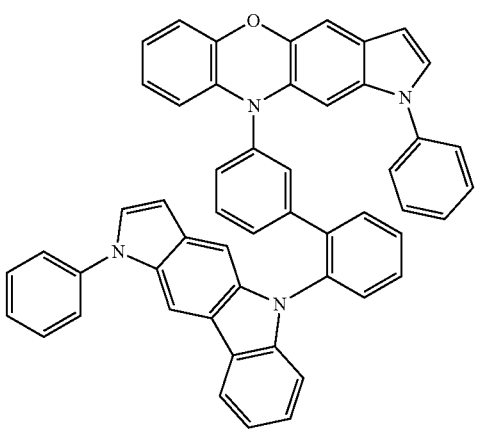
15

177
16
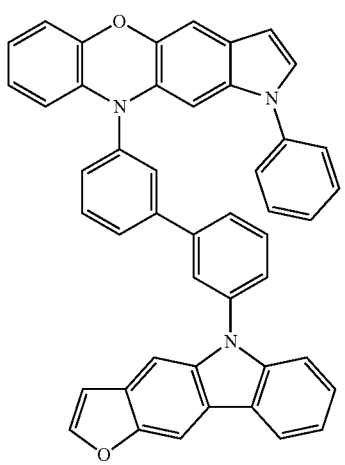
17
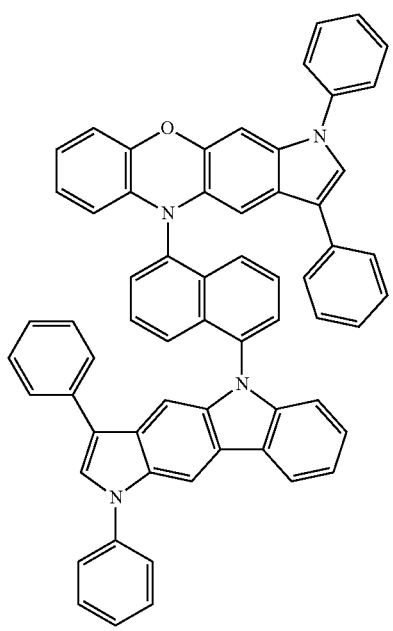
18
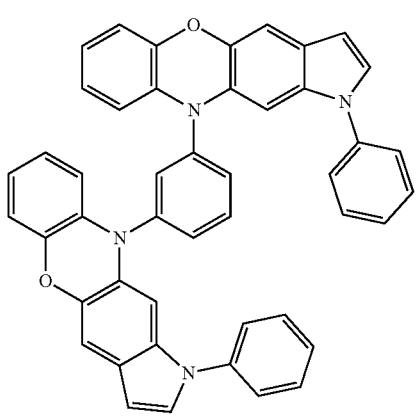
178
19
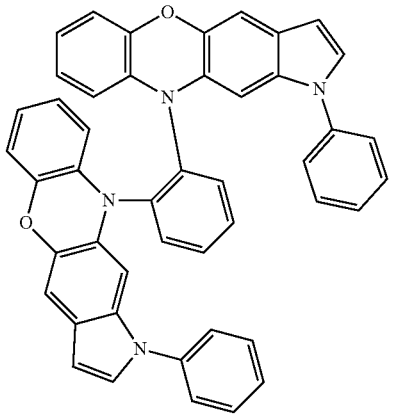
20
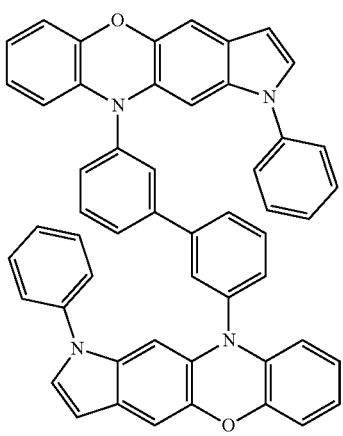
21
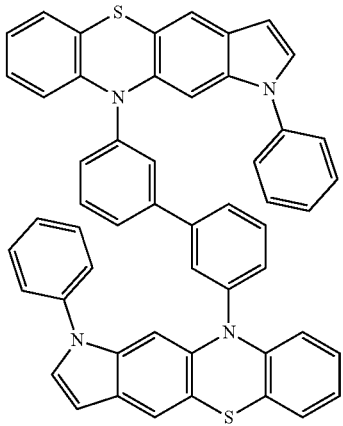

22
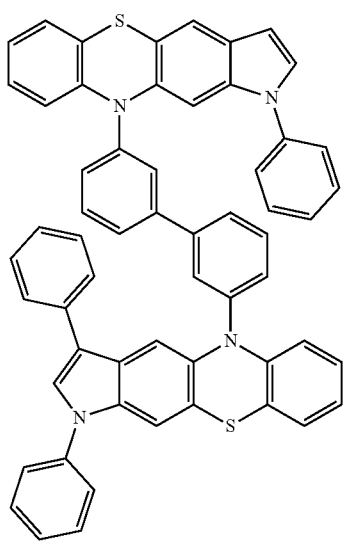
23
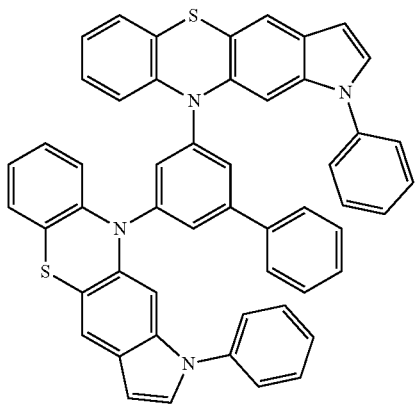
24
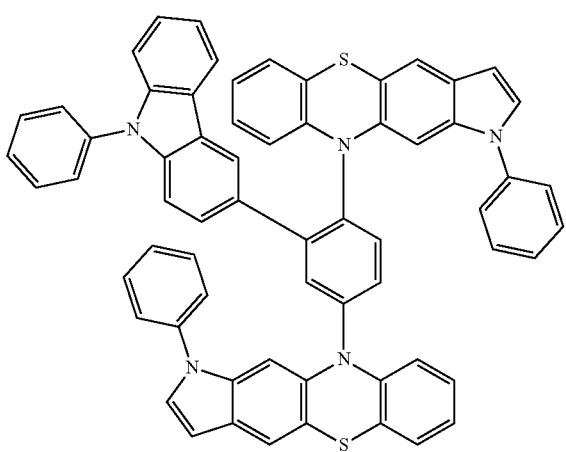
25
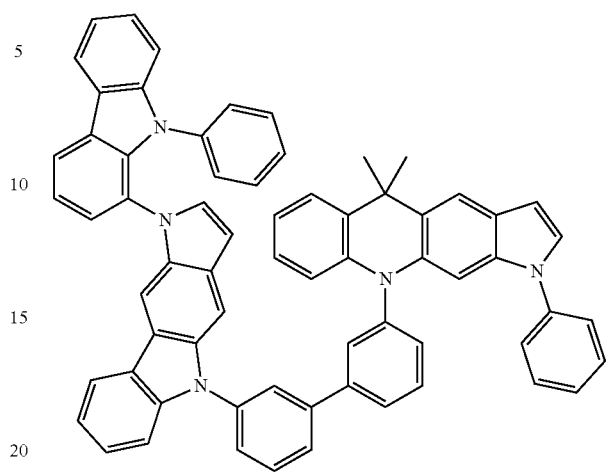
26
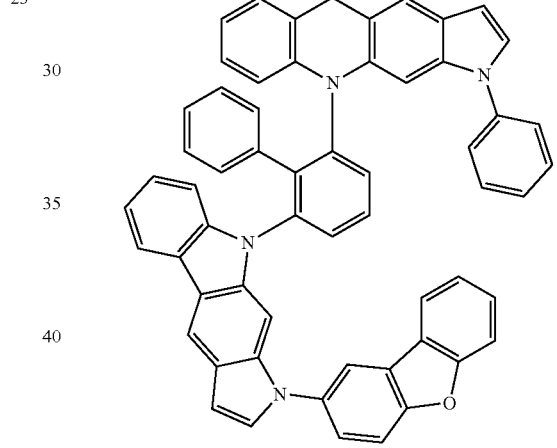
27
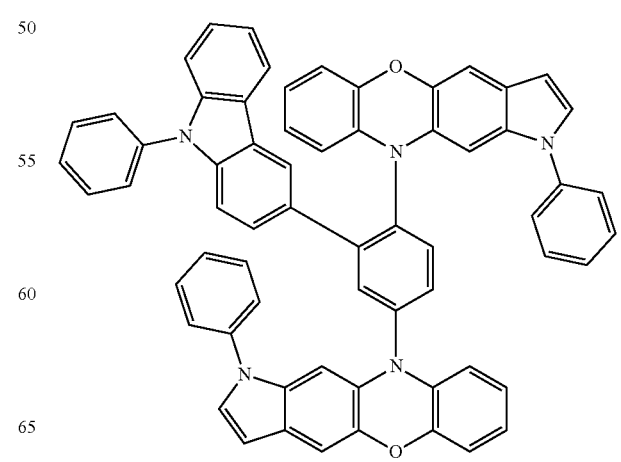

28
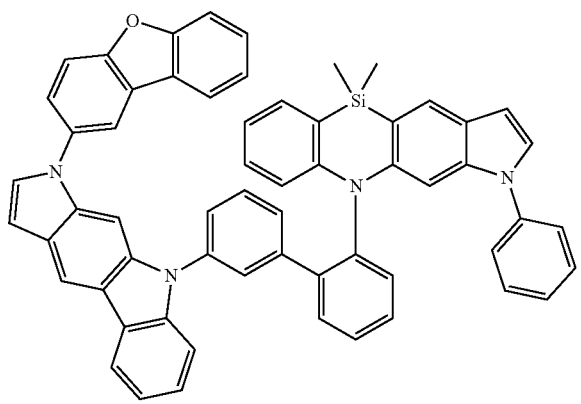
29
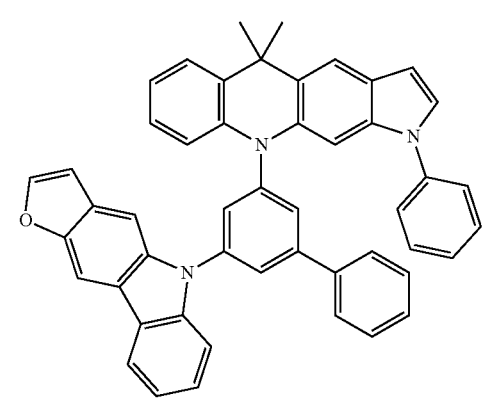
30
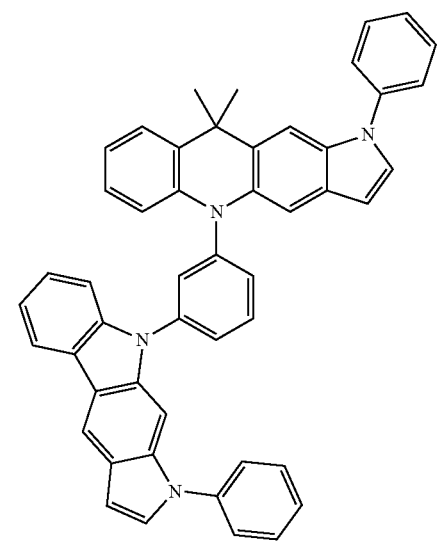
31
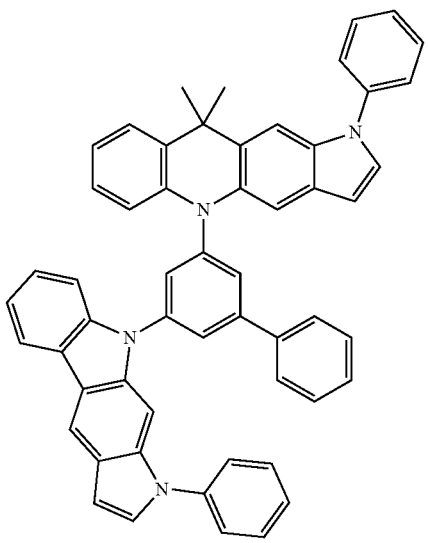
32
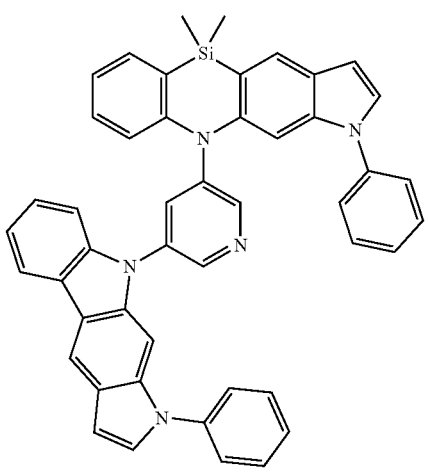
33
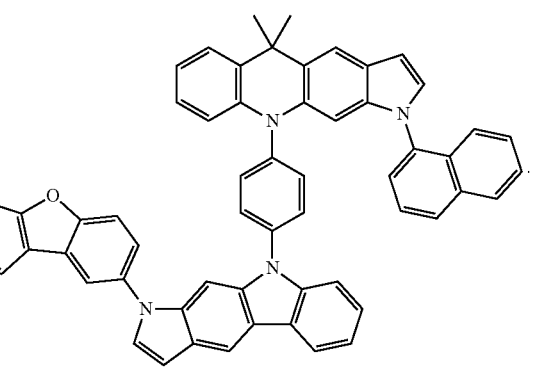
12. An organic light-emitting device comprising:
a first electrode;
a second electrode facing the first electrode; and
an organic layer between the first electrode and the second electrode and comprising an emission layer,
wherein the organic layer comprises at least one of the heterocyclic compound of claim 1.

13. The organic light-emitting device of claim 12, wherein:
the first electrode is an anode,
the second electrode is a cathode, and
the organic layer further comprises a hole transport region between the first electrode and the emission layer and an electron transport region between the emission layer and the second electrode.

14. The organic light-emitting device of claim 13, wherein:
the hole transport region comprises a hole injection layer, a hole transport layer, an emission auxiliary layer, an electron blocking layer, or any combination thereof.

15. The organic light-emitting device of claim 13, wherein:
the electron transport region comprises a hole blocking layer, an electron transport layer, an electron injection layer, or any combination thereof.

16. The organic light-emitting device of claim 13, wherein:
the electron transport region comprises a metal-containing material.

17. The organic light-emitting device of claim 12, wherein:
the emission layer comprises the at least one of the heterocyclic compound.

18. The organic light-emitting device of claim 12, wherein:
the emission layer comprises a host and a dopant, and
the host comprises the at least one of the heterocyclic compound.

19. The organic light-emitting device of claim 18, wherein:
the dopant comprises a phosphorescent dopant or a fluorescent dopant.

20. An electronic apparatus comprising:
the organic light-emitting device of claim 12; and
a thin-film transistor,
wherein the first electrode of the organic light-emitting device is in electrical contact with one of a source electrode and a drain electrode of the thin-film transistor.

* * * * *